US012479915B2

(12) United States Patent
Kamikawaji et al.

(10) Patent No.: US 12,479,915 B2
(45) Date of Patent: Nov. 25, 2025

(54) CYTOTOXICITY-INDUCING THERAPEUTIC AGENT

(71) Applicant: Chugai Seiyaku Kabushiki Kaisha, Tokyo (JP)

(72) Inventors: Shogo Kamikawaji, Kanagawa (JP); Yasuko Kinoshita, Kanagawa (JP); Shinya Ishii, Singapore (SG)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/310,829

(22) Filed: May 2, 2023

(65) Prior Publication Data

US 2024/0150465 A1 May 9, 2024

Related U.S. Application Data

(62) Division of application No. 16/957,837, filed as application No. PCT/JP2018/048409 on Dec. 28, 2018, now Pat. No. 11,667,713.

(30) Foreign Application Priority Data

Dec. 28, 2017 (JP) ................................ 2017-254279

(51) Int. Cl.
*A61P 35/00* (2006.01)
*C07K 16/28* (2006.01)

(52) U.S. Cl.
CPC .......... *C07K 16/2809* (2013.01); *A61P 35/00* (2018.01); *C07K 16/28* (2013.01); *C07K 2317/52* (2013.01); *C07K 2317/56* (2013.01)

(58) Field of Classification Search
CPC ................ C07K 16/2809; C07K 16/28; C07K 2317/52; C07K 2317/56; A61P 35/00
See application file for complete search history.

(56) References Cited

U.S. PATENT DOCUMENTS

| | | | |
|---|---|---|---|
| 9,127,071 | B2 | 9/2015 | Yoshida et al. |
| 9,834,606 | B2 | 12/2017 | Li et al. |
| 11,274,151 | B2 | 3/2022 | Naoi et al. |
| 2003/0180784 | A1 | 9/2003 | McCarthy et al. |
| 2005/0137130 | A1 | 6/2005 | Bodmer et al. |
| 2007/0141066 | A1 | 6/2007 | Phillips et al. |
| 2008/0220495 | A1 | 9/2008 | McCarthy et al. |
| 2012/0328624 | A1 | 12/2012 | Yoshida et al. |
| 2014/0112914 | A1 | 4/2014 | Nezu et al. |
| 2016/0244530 | A2 | 8/2016 | Yoshida et al. |
| 2017/0037130 | A1 | 2/2017 | Raum et al. |
| 2017/0306036 | A1 | 10/2017 | Vu et al. |
| 2017/0349668 | A1 | 12/2017 | Rattel et al. |
| 2018/0326058 | A1 | 11/2018 | Tsunenari et al. |
| 2021/0301016 | A1 | 9/2021 | Naoi et al. |
| 2021/0363250 | A1 | 11/2021 | Kamikawaji et al. |
| 2021/0380715 | A1 | 12/2021 | Yoshida et al. |
| 2022/0251201 | A1 | 8/2022 | Naoi et al. |
| 2024/0010725 | A1 | 1/2024 | Naoi et al. |
| 2024/0400721 | A1 | 12/2024 | Naoi et al. |

FOREIGN PATENT DOCUMENTS

| | | | |
|---|---|---|---|
| EP | 2 078 731 | A1 | 7/2009 |
| EP | 2817338 | B1 | 7/2017 |
| JP | H11299493 | A | 11/1999 |
| JP | 2008273973 | A | 11/2008 |
| JP | 2009523709 | A | 6/2009 |
| JP | 2016513094 | A | 5/2016 |
| JP | 2017526350 | A | 9/2017 |
| JP | 2018527908 | A | 9/2018 |
| JP | 2018188437 | A | 11/2018 |
| TW | 201708261 | A | 3/2017 |
| WO | WO9845434 | A1 | 10/1998 |
| WO | 00/47602 | | 8/2000 |
| WO | 01/12664 | A2 | 2/2001 |
| WO | 01/075067 | A3 | 10/2001 |
| WO | 02/14358 | A2 | 2/2002 |
| WO | 03/025138 | A2 | 3/2003 |
| WO | 04/030615 | A2 | 4/2004 |
| WO | 2004/053102 | A2 | 6/2004 |
| WO | 2005/077090 | A2 | 8/2005 |

(Continued)

OTHER PUBLICATIONS

MacCallum et al., Antibody-antigen Interactions: Contact Analysis and Binding Site Topography, 1996, Journal of Molecular Biology, 262: p. 732-745. (Year: 1996) (Year: 1996).*
Rudikoff et al, Single amino acid substitution altering antigen binding specificity, 1982, 79:1979-1983 (Year: 1982) (Year: 1982).*
Casset et al, A peptide mimetic of an anti-CD4 monoclonal antibody by rational design, 2003, 307: 198-205 (Year: 2003) (Year: 2003).*
Holm et al, Functional mapping and single chain construction of the anti-cytokeratin 8 monoclonal antibody TS1, 2007: 1075-1084 ( Year: 2007) (Year: 2007).*
Chen et al Selection and Analysis of an Optimized Anti-VEGF Antibody: Crystal Structure of an Affinity-matured Fab in Complex with Antigen, JMB, 293, pp. 865-881, 1999) (Year: 1999).*
U.S. Appl. No. 18/343,850, filed Jun. 29, 2023, Naoi et al., related application.
Campoli et al., "Immunotherapy of Malignant Disease with Tumor Antigen-Specific Monoclonal Antibodies", Clinical Cancer Research, vo. 16, No. 1, Jan. 1, 2010, pp. 11-20 (10 pages total).

(Continued)

*Primary Examiner* — Nelson B Moseley, II
*Assistant Examiner* — Dennis J Sullivan
(74) *Attorney, Agent, or Firm* — Nixon & Vanderhye P.C.

(57) ABSTRACT

The present inventors discovered novel multispecific antigen-binding molecules with excellent cellular cytotoxicity, which comprise a first domain comprising a first antigen variable region which binds to DLL3 and a second domain comprising a second antigen variable region which binds to T cell receptor complex. The present inventors prepared further bispecific antibodies, and assessed their T cell-dependent cell cytotoxicity (TDCC), and found that they also show strong TDCC activity. Since the molecules/antibodies of the present invention show a strong cytotoxicity against cells expressing DLL3, novel pharmaceutical compositions comprising the molecules/antibodies for treating or preventing various cancers associated with DLL3 can be provided.

31 Claims, 10 Drawing Sheets

Specification includes a Sequence Listing.

(56) References Cited

FOREIGN PATENT DOCUMENTS

| | | | |
|---|---|---|---|
| WO | 2007/080597 | A2 | 7/2007 |
| WO | 2007/111733 | A2 | 10/2007 |
| WO | 2008/047925 | A1 | 4/2008 |
| WO | 2009/124931 | A2 | 10/2009 |
| WO | 2011/093097 | A1 | 8/2011 |
| WO | WO2012073985 | A1 | 6/2012 |
| WO | 2013/125746 | A2 | 8/2013 |
| WO | WO2014125273 | A1 | 8/2014 |
| WO | 2015/127407 | A1 | 8/2015 |
| WO | WO2016016415 | A1 | 2/2016 |
| WO | WO2016016859 | A1 | 2/2016 |
| WO | WO2017010874 | A1 | 1/2017 |
| WO | 2017/021349 | A1 | 2/2017 |
| WO | WO2017086367 | A1 | 5/2017 |
| WO | WO2017201442 | A1 | 11/2017 |
| WO | WO2018204907 | A1 | 11/2018 |
| WO | WO2019111871 | A1 | 6/2019 |
| WO | WO2019131988 | A1 | 7/2019 |
| WO | WO2019234220 | A1 | 12/2019 |
| WO | WO2020067419 | A1 | 4/2020 |
| WO | WO2021200898 | A1 | 10/2021 |
| WO | WO2022084915 | A1 | 4/2022 |

OTHER PUBLICATIONS

Sigerz et al., "Hybrid antibodies can target sites for attack by T cells", Nature, vol. 314, No. 6012. Apr. 18, 1985, pp. 628-631 (2 pages total).

Mezzanzanica et al., "Human Ovarian Carcinoma Lysis By Cytotoxic T Cells Targeted By Bispecific Monoclonal Antibodies: Analysis of the Antibody Components", Int. J. Cancer, vol. 41, No. 4, pp. 609-615, 1988 (4 pages total).

Staerz et al., "Hybrid hybridoma producing a bispecific monoclonal antibody that can focus effector T-cell activity", Proc. Natl Acad. Sci. USA, vol. 83, vol. 5, pp. 1453-1457, Mar. 1986, Immunology (3 pages total).

Mack et al., "A small bispecific antibody construct expressed as a functional single-chain molecule with high tumor cell cytotoxicity", Proc. Natl. Acad. Sci. USA, vol. 92, pp. 7021-7025, Jul. 1995 (3 pages total).

Wolf et al., "BiTEs: bispecific constructs with unique anti-tumor activity", Drug Discov Today, vol. 10, No. 18, pp. 1237-1244, Sep. 2005 (8 pages total).

Dreier et al., "Extremely Potent, Rapid and Costimulation-Independent Cytotoxic T-Cell Response Against Lymphoma Cells Catalyzed by a Single-Chain Bispecific Antibody", Int. J. Cancer, Aug. 20, 2002, vol. 100, No. 6, pp. 690-697 (8 pages total).

Sebastian et al., "Treatment of non-small cell lung cancer with the trifuntional monocional antibody catumaxomab (anti-EpCAM x anti-CD3): phase I study" Cancer Immmunol Immunother, 2007, vol. 56, No. 10, pp. 1637-1644 (8 pages total).

Schlereth et al., "T-cell activation and B-cell depletion in chimpanzees treated with a bispecific anti-CD 19/anti-CD3 single-chain antibody construct", Cancer Immunol Immunother, 2006, vol. 55, No. 5, pp. 503-514 (12 pages total).

Amann et al., "Theraputic window of an EpCAM/CD3-specific BiTE antibody in mice is determined by a subpopulation of EpCAM-expressing lymphocytes that is absent in humans", Cancer Immunol Immunother, 2009, vol. 58, No. 1, pp. 95-109 (15 pages total).

Bulman et al., "Mutations in the human Delta homologue, DLL3, cause axial skeletal defects in spondylocostal dysostosis". Nature Genetics, Apr. 2000, vol. 24, No. 4, pp. 438-441(4 pages total).

Turnpenny et al., "Novel mutations in DLL3, a somitogenesis gene encoding ligand for the Notch signalling pathway, cause a consistent pattem of abnormal vertebral segmentation in spondylocostal dysostosis", J Med Genet., May 2003, vol. 40, No. 5, pp. 333-339 (7 pages total).

Phillips et al., "Molecular subclasses of high-grade glioma predict prognosis, delineate a pattern of disease progression, and resemble stages in neurogenesis", Cancer Cell, vol. 9, vol. 1, pp. 157-173, Mar. 2006 (17 pages total).

Mullendore et al., "Ligand-dependent Notch Signaling is Involved in Tumor Initiation and Tumor Maintenance in Pancreatic Cancer", Clin. Cancer Res., Apr. 2009, vol. 15, No. 7, pp. 2291-2301 (11 pages total).

Saunders et al., "A DLL3-targeted antib drug conjugate eradicates high-grade pulmonary neuroendocrine tumor-initiating cells in vivo," Science Translational Medicine, Aug. 26, 2015, vol. 7, Issue 302, pp. 1-13.

Declaration from Dr. William Decker, dated Dec. 2020, filed in the Defence of Oppositions Against European Patent No. 2,530,091.

Spirin, Alexander S., "Storage of Messenger RNA in Eukaryotes: Envelopment With Protein, Translational Barrier at 5' Side, or Conformational Masking by 3' Side?," Molecular Reproduction and Development, May 1994, vol. 3 Issue 1, pp. 107-117.

Ranjan et al., "Masking mRNA from translation in somatic cells," Genes and Development (1993) vol. 7, pp. 1725-1736.

Declaration from Professor Mark Gerstein, "Expert Opinion," dated Feb. 2020, submitted in opposition proceedings against European Patent No. 2,530,091.

Gad et al., "Nonclinical Use in Studies by Multiple Routes in Multiple Species," International Journal of Toxicology, Nov.-Dec. 2006, vol. 25, Issue 6, pp. 499-521.

Katoh et al., "Precision medicine for human cancers with Notch signaling dysregulation (Review)," International Journal of Molecular Medicine, Feb. 2020, vol. 45, Issue 2, pp. 279-297.

Espinoza et al. "Notch Inhibitors for Cancer Treatment," Pharmacology & Therapeutics, Aug. 2013, vol. 139, Issue 2, pp. 95-110.

Von Meerten et al. "Complement-Induced Cell Death by Rituximab Depends on CD20 Expression Level and Acts Complementary to Antibody-Dependent Cellular Cytotoxicity," Clinical Cancer Research, Jul. 1, 2006, vol. 12, Issue 13, pp. 4027-4035.

Gershoni et al., "Epitope Mapping—The First Step in Developing Epitope-Based Vaccines," Biodrugs, 2007, vol. 21, Issus 3, pp. 145-156.

Knowles et al., "Advances in Immuno-Positron Emission Tomography: Antibodies for Molecular Imaging in Oncology," Journal of Clinical Oncology, Nov. 1, 2012, vol. 30, No. 31, pp. 3884-3892.

Communication, dated Mar. 22, 2019, issued by European Patent Office in European Patent No. 2,990,420.

De La Lastra et al., "Epitope mapping of 10 monoclonal antibodies against the pig analogue of human membrane cofactor protein (MCP)," Imunology, Apr. 1999, vol. 96, No. 4, pp. 663-670.

Coullu et al., "Cooperation between Wnt and Notch signalling in human breast cancer," (2007) Breast Cancer Research, May 11, 2007, vol. 9: No. 3, (3 pages).

Guo et al., "Role of Notch and its oncogenic signaling crosstalk in breast cancer," Biochimica et Biophysica Acta (BBA)—Reviews on Cancer, Apr. 2011, vol. 1815, Issue 2, pp. 197-213.

Ercan et al., "Marrimary Development and Breast Cancer; The Role of Stem Cell," Current Molecular Medicine, Jun. 2011, vol. 11, No. 4, pp. 270-285.

Wang et al., "Epithelial-mesenchymal transition in breast cancer progression and metastasis," Chinese Journal of Cancer; Sep. 2011, vol. 30, No. 9,; pp. 603-611.

Information about the result of oral proceedings in European Patent Application No. 11736812.6, dated Mar. 4, 2021.

Communication, dated Jun. 10, 2020, issued by European Patent Office in European Application No. 18 156 974.0.

Communication, dated Oct. 10, 2019, issued by European Patent Office in European Application No. 11736812.6.

Weinzierl, et al., Notice of opposition filed against EP 2 530 091 B1 dated Jan. 2, 2019 (50 pages).

Unsin, Dr. Claudia E, Notice of opposition filed against EP 2 530 091 B1 dated Jan. 2, 2019 (16 pages).

Livingston et al., "Selection of GM2, fucosyl GM1, globo H and polysialic acid as targets on small cell lung Cancers for antibody mediated immuntherapy." Cancer Immunol. Immunother., 2005, 54: 1018-1025.

Chugai Selyaku Kabushiki Kaisha, "Sequence Alignments;" dated Mar. 6, 2020, submitted in counterpart European Patent Application No. 11736812.6, 2 pages.

Maler et al., "Correlation of mRNA and protein in complex biological samples," FEBS Letters, 2009, 583: 3966-3973.

(56) References Cited

OTHER PUBLICATIONS

Communication, dated Jun. 10, 2020, issued by the European Patent Office in counterpart European Patent Office a counterpart European Application No. 18 156 974 0-1111.
Chugai Seiyaku Kabushiki Kaisha, Final Walten Submission, dated Mar. 6, 2020, submitted in counterpart European Patent Application No. 11736812.6.
Communication, dated Oct. 10, 2019, from the European Patent Office in counterpart European Application No. 11736812.6.
Brendan D'Souza, et al. "Canonical and Non-Canonical Notch Ligands", Current Topics in Developmental Biology, 2010, vol. 92, pp. 73-129 (57 pages total).
Dov Greenbaum, et al., "Comparing protein abundance and mRNA expression levels on a genomic scale" Genome Biology, Aug. 29, 2003, vol. 4, issue 9, article 117, pp. 117.1-117.8 (8 pages total).
Communication, dated Jan. 30, 2019, issued by the European Patent Office in counterpart Application No. 11736812.6.
Communication, dated Jan. 9, 2019, issued by the European Patent Office in counterpart Application No. 11736812.6.
Communication, dated Jan. 8, 2019, issued by the European Patent Office in counterpart Application No. 11736812.6.
Communication, dated Jan. 15, 2019, issued by the European Patent Office in counterpart Application No. 11736812.6.
"Monoclonal Anti-human DLL3 Antibody", Product sheet for Human DLL3 Antibody, MAB4315, R&D Systems, Inc., 2007.
"Immunoglobulin G" Immunoglobulin G, Review InvivoGen, 2011.
Nimmerjahn, Falk et al., "Fcy Receptors Old Friends and New Family Members" Immunity, 2006, pp. 19-28, vol. 24, pp.
Stockwin, LH et al., "Antibodies as therapeutic agents: vive la renaissance!", Expert Opinion on Biological Therapy, 2003, vol. 3, No. 7, pp. 1139-1152.
Shields, Robert L. et al., "High Resolution Mapping of the Binding Site on Human IgG1 for FcyRI, FoyRII, FcyRIII, and FcRn Design of IgG1 Variants with Improved Binding to the FcyR", The Journal of Biological Chemistry, 2001, vol. 276, No. 9 pp. 6591-6604.
Zanetti, M et al., "The Antibodies," Harwood Academic Publishers, 2000, vol. 6 pp. 36-37.
Goding, James W. et al., "Moriocional Antibodies: Principles and Practice" Academic Press, 1996, Third Edition, pp. 134-135.
Carter, Paul et al., "Identification and validation of cell surface antigens for antibody in oncology", Endocrine-Related Cancer, 2004, vol. 11, pp. 659-687.
Carter, Paul J. et al., "Antibody-Drug Conjugates for Cancer Therapy", The Cancer Journal, 2008, vol. 14, No. 3, pp. 154-169.
Adams, Gregory P et al., "Monoclonal antibody therapy of cancer", Nature Biotechnology, 2005, vol. 23, No. 9, pp. 1147-1157.
Sun, Yu et al., "Antibody-drug conjugates as targeted cancer therapeutics", Acta Pharmaceutica Sinica, 2009, vol. 44, No. 9, pp. 943-952.
Chen, Jin et al., "Antibody-cytotoxic agent conjugates for cancer therapy", Expert Opinion on Drug Delivery, 2005, vol. 2, No. 5, pp. 873-890.
Grant, Stefan C. et al., "Targeting of small-cell lung cance using the anti-GD2 ganglioside monoclonal antibody 3F8; a pilot trial", European Journal of Nuclear Medicine, 1996; vol. 33, No. 2, pp. 145-149.
Dunwoodie, Sally L, "The role of Notch in patterning the human vertebral column", Current Opinion in Genetics & Development, 2009, vol. 19, pp. 329-337.
D'Souza, B. et al., "The many facets of Notch ligands", Oncogene, 2008, vol. 27, pp. 5148-5167.
Henke, R. Michael et al., "Ascl1 and Neurog2 Form Novel Complexes and Regulate Della-like3 (Dll3) Expression in the Neural Tube", Dev Biol., 2009, vol. 328, No. 2, pp. 529-540.
Ball, Douglas W., "Achaete—scute homolog-1 and Notch in lung neuroendocrine development and cancer", Cancer Letters, 2004, vol. 204, pp. 159-169.
Choi, Kuicheon, et al., "Distinct Biological Roles for the Notch Ligands Jagged-1 and Jagged-2", The Journal of Biological Chemistry, 2009, vol. 284, No. 26, pp. 17766-17774.
"Comougen Announces Discovery of Blood Based Biomarker for Diagnosis of Lung Cancer", Apr. 29, 2008 (2 pages), retrieved from https://www.cgen.com/mediacenter/compugen-announces-discover-of-blood-based-biomarker-for-diagnosis-of-lung-cancer.
Taneja, Tarvinder K., et al., "Markers of small cell lung cancer", World Journal of Surgical Oncology, 2004, vol. 2. No. 10, pp. 1-5.
Chung, Shan et al., "Characterization of in vitro antibody-dependent cell-mediated cytotoxicity activity of therapeutic antibodies—Impact of effector cells", Journal of Immunological Methods, 2014, vol. 407, pp. 63-75.
Weng, Wen-Kal et al., "Two Immunoglobulin G Fragment C Receptor Polymorphisms Independently Predict Response to Rituximab In Patients With Follicular Lymphphoma", Journal of Clinical Oncology, 2003, vol. 21, No. 21, pp. 3940-3947.
Ayyakannu Ayyanan et al., "Increased Wht signaling triggers oncogenic conversion of human breast epithelial cells by a Notch-dependent mechanism", Proceedings of the National Academy of Sciences of USA, 2006, pp. 3799-3804, vol. 103, No. 10.
Communication dated Mar. 24, 2015, issued by the Japanese Patent Office in counterpart Application No. 2011551775.
Communication for EP 11736812.6 dated Jun. 6, 2013, along with Supplementary European Report dated May 29, 2013.
Ena Ladi et al., "The divergent DSL ligand DII3 does not activate Notch signaling but cell autonomously attenuates signaling induced by other DSL ligands", The Journal of Cell Biology, 2005, pp. 983-992, vol. 170, No. 6.
Heidi S. Phillips et al., "Molecular subclasses of high-grade glioma predict prognosis, delineate a pattern of disease progression, and resemble stages in neurogenesis", Cancer Cell, 2006, pp. 157-173, vol. 9.
Insa Geffers et al., "Divergent functions and distinct localization of the Notch ligands DLL1 and DLL3 in vivo", The Journal of Cell 465-476, vol. 178, No. 3.
International Preliminary Report on Patentability for International Application No. PCT/JP2011/000485, dated Sep. 27, 2012.
International Search Report for PCTJP2011/000485 dated Mar. 1, 2011.
Jiang et al., "Achsete-Scute Complex Homologue 1 Regulates Tumor-Initiating Capacity in Human Small Cell Lung Cancer", Cancer Research, 69(3):845-854 (2009), Abstract No. XP002697824.
Kenya Shitara, "Potelligent Antibodies as Next Generation Therapeutic Antibodies", Yakugaku Zasshi, 2009, pp. 3-9, vol. 129, No. 1.
Michael E. Mullendore et al., "Ligand-dependent Notch Signaling Is Involved in Tumor Initiation and Tumor Maintenance In Pancreatic Cancer", Clin Cancer Res, 2009, pp. 2291-2301, vol. 15.
Michael E. Bluman et al., "Mutations in the human Della homologue, DLL3, cause axial skeletal detects in spondylocostal dysostosis", Nature Genetics 2000, pp. 438-441, vol. 24.
Millipore: "Anti-Delta3, clone 1E7.2", Internet citation, Abstract No. XP002697359, pp. 1-3 (Jul. 15, 2008).
P.D Turnpenny et al., "Novel mutations in DLL3, a somitogenesis gene encoding a ligand for the Notch signaling pathway, cause a consistent pattern of abnormal vertebral segmentation in spondylcostal dysostosis", J Med Genet, 2003, pp. 333-339, vol. 40.
R&D Systems: "Human DLLS Antibody", Monoclonal Mouse IgG2B Clone #378703, Catalog No. MAB4315, Internet Citation, Abstract No. XP002697358 (May 20, 2010).
De Pascalis et al. The Journal of Immunology (2002) 169, 3076-3084.
Lamminmakl et al. (JBC 2001, 276:36687-36694).
Padlan et al. (PNAS 1989, 86:5938-5942).
Song et al. (Biochem Biophys: Res Comm 268:390-394 (2000)).
Kumar et al. (J. Biol. Chem, 275:35129-35136 (2000)).
Smith-Gill et al. (J. Immunol. 139:4135-4144 (1987)).
Ward et al. Nature 341:544-546 (1989)).
Holm et al. (2007) Mol. Immunol. 44: 1075-1084).
Vajdos et al. (2002) J. Mol. Siol. 320, 415-428).
Casset et al. (2003) BBRC 307, 198-205).
MacCallum et al. (J. Mol. Biol. (1996) 262:732-745).
Rudikoff et al. (Proc Natl Acad Sci USA 1982 vol. 79 p. 1979-1983).
Baeuerle, P. A., et al., "BiTE: Teaching antibodies to engage T-cells for cancer therapy," Curr Opin Mol Ther., 11(1):22-30 (2009).

(56) References Cited

OTHER PUBLICATIONS

Bluemel, C., et al., "Epitope distance to the target cell membrane and antigen size determine the potency of T cell-mediated lysis by BiTE antibodies specific for a large melanoma surface antigen," Cancer Immunol Immunother., 59:1197-1209 (2010).
Communication of Notices of Oppositions in European Application No. 18156974.0/Patent No. 3342786 dated Apr. 13, 2022.
Curriculum Vitae of Professor Dr. William K. Decker, cited in the Grounds of Appeal in European Patent Application No. 11736812.6 on Sep. 17, 2021.
Decision Revoking European Patent No. 2530091 dated May 7, 2021.
Second Declaration of Professor Dr. William K. Decker dated Sep. 13, 2021, cited in the Grounds of Appeal in European Patent Application No. 11736812.6 on Sep. 17, 2021.
Dickopf, S., et al., "Format and geometries matter: Structure-based design defines the functionality of bispecific antibodies," Computational and Structural Biotechnology Journal, 18:1221-1227 (2020).
Final Office Action dated Oct. 3, 2014 in U.S. Appl. No. 13/575,861, filed Sep. 12, 2012, Yoshida et al.
Final Office Action dated Feb. 16, 2017 in U.S. Appl. No. 14/846,135, filed Sep. 4, 2015, Yoshida et al.
Edwards, B. M., et al., "The Remarkable Flexibility of the Human Antibody Repertoire; Isolation of Over One Thousand Different Antibodies to a Single Protein, BLyS," J Mol Biol., 334:103-118 (2003).
Goldenberg, D. M., et al., "Veltuzumab (humanized anti-CD20 monoclonal antibody): characterization, current clinical results, and future prospects," Leukemia & Lymphoma, 51(5):747-755 (2010), cited in the Grounds of Appeal in European Patent Application No. 11736812.6 on Sep. 17, 2021.
Ingle, G. S., et al., "High CD21 expression inhibits internalization of anti-CD19 antibodies and cytotoxicity of an anti-CD19-drug conjugate," British Journal of Haematology, 140:46-58 (2008), cited in the Grounds of Appeal in European Patent Application No. 11736812.6 on Sep. 17, 2021.
Kontermann, R. E., "Recombinant bispecific antibodies for cancer therapy," Acta Pharm Sininca, 26(1):1-9 (2005).
Lloyd, C., et al., "Modelling the human immune response: performance of a $10^{11}$ human antibody repertoire against a broad panel of therapeutically relevant antigens," Prot Eng Des Sel., 22(3):159-168 (2009).
Magro, G., et al., "Differential expression of mucins I-6 in papillary thyroid carcinoma: evidence for transformation-dependent post-translational modifications of MUCI in situ," J Pathol., 200:357-369 (2003), cited in the Grounds of Appeal in European Patent Application No. 11736812.6 on Sep. 17, 2021.
Minutes of the oral proceedings before the Examining Division in European Application No. 18156974.0 dated Apr. 16, 2021.
National Library of Medicine, COVID-19 Information, Cited In for PMID: 16501043, Mar. 1, 2022.
Notice of Opposition 1 in European Application No. 18156974.0/Patent No. 3342786 dated Mar. 16, 2022.
Notice of Opposition 2 in European Application No. 18156974.0/Patent No. 3342786 dated Mar. 21, 2022.
Office Action dated Jun. 5, 2014 in U.S. Appl. No. 13/575,861, filed Sep. 12, 2012, Yoshida et al.
Office Action dated Jun. 5, 2020 in U.S. Appl. No. 14/846,135, filed Sep. 4, 2015, Yoshida et al.
Office Action dated Aug. 19, 2019 in U.S. Appl. No. 14/846,135, filed Sep. 4, 2015, Yoshida et al.
Office Action dated Jan. 7, 2019 in U.S. Appl. No. 14/846,135, filed Sep. 4, 2015, Yoshida et al.
Office Action dated Jun. 11, 2018 in U.S. Appl. No. 14/846,135, filed Sep. 4, 2015, Yoshida et al.
Office Action dated Oct. 20, 2017 in U.S. Appl. No. 14/846,135, filed Sep. 4, 2015, Yoshida et al.
Owonikoko, T., et al., "Two Novel Immunotherapy Agents Targeting DLL3 in SCLC: Trials in Progress of AMG 757 and AMG 119," J Thorac Oncol., 13(10S):S351-S353 (2018).
Roda-Navarro and Alvarez-Vallina, L., "Understanding the Spatial Topology of Artificial Immunological Synapses Assembled in T Cell-Redirecting Strategies: A Major Issue in Cancer Immunotherapy," Front Cell Dev Biol., 7:370 (2020).
Schwarz, S., et al., "Twelve of fourteen surface epitopes of receptor-bound human chorionic gonadotropin (hCG) being antibody-inaccessible suggest an extensive involvement of the long extracellular domain of the hCG receptor," Mol Cell Endocrinology, 82:71-79 (1991).
Zhang, Y. and Pastan, I., "High Shed Antigen Levels within Tumors: An Additional Barrier to Immunoconjugate Therapy," Clin Cancer Res., 14(24):7981-7986 (2008), cited in the Grounds of Appeal in European Patent Application No. 11736812.6 on Sep. 17, 2021.
Japanese Office Action dated Dec. 6, 2022 in Japanese Patent Application No. 2020-536283.
U.S. Appl. No. 17/216,981, filed Mar. 30, 2021, Naoi et al., related application.
U.S. Appl. No. 17/670,917, filed Feb. 14, 2022, Naoi et al., related application.
U.S. Appl. No. 17/406,504, filed Aug. 19, 2021, Yoshida et al., related application.
U.S. Appl. No. 18/696,717, filed Mar. 28, 2024, Naoi et al., related application.
U.S. Appl. No. 18/654,675, filed May 3, 2024, Naoi et al., related application.
U.S. Appl. No. 18/696,717, filed Mar. 28, 2024, Naoi et al.
U.S. Appl. No. 18/654,675, filed May 3, 2024, Naoi et al.
Alberts, B., et al., "Molecular Biology of The Cell," Fifth Edition, Garland Science, 329-331, 415 (2008).
Banks, W. A., "Developing drugs that can cross the blood-brain barrier: applications to Alzheimer's disease," BMC Neuroscience, 9(Suppl 3):S2 (2008).
Chapman, G., et al., "Notch inhibition by the ligand Delta-Like 3 defines the mechanism of abnormal vertebral segmentation in spondylocostal dysostosis," Human Molecular Genetics, 20(5):905-916 (2011).
Chen, G., et al., "Discordant Protein and mRNA Expression in Lung Adenocarcinomas," Molecular & Cellular Proteomics, 1:304-313 (2002).
Clark, D., "Molecular Biology," Elsevier Inc., 63-34 (2005).
Compugen Ltd., Press Releases, "Compugen Announces Discovery of Blood Based Biomarker for Diagnosis of Lung Cancer," 2 pages (2008).
Daniel, V. C., et al., "Developmental signalling pathways in lung cancer," Respirology, 11:234-240 (2006).
Emuss, V., et al., "KSHV Manipulates Notch Signaling by DLL4 and JAG1 to Alter Cell Cycle Genes in Lymphatic Endothelia," PLoS Pathogens, 5(10):e1000616 (2009).
Expert Declaration of Professor Dr. Sven Roger Perner dated Mar. 1, 2023.
Haglund, K., et al., "Aberrant Receptor Signaling and Trafficking as Mechanisms in Oncogenesis," Critical Reviews™ in Oncogenesis, 13(1):39-74 (2007).
Hipp, S., et al., "A Bispecific DLL3/CD3 IgG-Like T-Cell Engaging Antibody Induces Antitumor Responses in Small Cell Lung Cancer," Clin Cancer Res., 26(19):5258-5268 (2020).
Letter from Opponent 1, Dr. André Guder, Response to Patentee's Observations to the Oppositions of European Patent No. 3342786 dated Mar. 2, 2023.
Luckey, M., "Membrane," Structural Biology with Biochemical and Biophysical Foundations, 90-94, 184-186 (2008).
Owonikoko, T., K., et al., "Updated results from a phase 1 study of AMG 757, a half-life extended bispecific T-cell engager (BiTE) immune-oncology therapy against delta-like ligand 3 (DLL3), in small cell lung cancer (SCLC)," Journal of Clinical Oncology, 39(15 supp):8510-8510 (2021).
Patel, M. M., et al., "Getting into the Brain," CNS Drugs, 23(1):35-58 (2009).
Preliminary Opinion/Summons to attend oral proceedings pursuant to Rule 115(1) EPC dated Jun. 5, 2023 in Opposition of European Patent No. 3342786.
Qiao, L. and Wong, B. C. Y., "Role of *Notch* signaling in colorectal cancer," Carcinogenesis, 30(12):1979-1986 (2009).

(56) References Cited

OTHER PUBLICATIONS

Sequence alignment of hypothetical proteins encoding transcripts from D1 to wildtype human DLL3, submitted in Opposition of European Patent No. 3342786 on Aug. 23, 2022.
Stryer, L., "Biochemistry," Third Edition, W. H. Freeman and Co., 91 (1988).
Voet, D. and Voet, J. G., "Biochemistry," John Wiley & Sons, Ltd., 852-853 (1990).
Xiao, M.-J., et al., "Notch signaling and neurogenesis in normal and stroke brain," Int J Physiol Pathophysiol Pharmcol., 1:192-202 (2009).
Chou, K.-C. and Elrod, D. W., "Prediction of Membrane Protein Types and Subcellular Locations," Proteins: Structure, Function, and Genetics, 34:137-153 (1999).
U.S. Appl. No. 18/978,252, filed Dec. 12, 2024, Naoi et al., related application.
Decision revoking European Patent (Art. 103(3)(b) EPC) dated Sep. 26, 2024, in European Patent No. EP3342786B1, published Jun. 23, 2021, 46 pages.
Declaration of Professor Duncan Burnaby Sparrow and Curriculum Vitae dated Feb. 9, 2024.
Declaration of Professor Julien Sage dated Apr. 18, 2024.

* cited by examiner

In vitro TDCC activity of chimeric anti-DLL3/CD3 bispecific antibodies in SK-MEL-30

In vitro TDCC activity of chimeric anti-DLL3/CD3 bispecific antibodies in SCLCs

Evaluation of the in vivo drug efficacy in SCLC xenograft models

Fig. 8

Antibody A

Antibody B

| Antibody B \ Antibody A | DL301-SG1 | DL306-SG1 | DL309-SG1 | DL312-SG1 | D30316AE02-SG1 | D30841AE05-SG1 |
|---|---|---|---|---|---|---|
| DL301-SG1 | -0.1 | 1.3 | 1.2 | 1.3 | 1.3 | 1.3 |
| DL306-SG1 | 1.1 | 0.0 | 0.9 | 1.2 | 1.5 | 0.0 |
| DL309-SG1 | 1.4 | 1.4 | -0.1 | 1.5 | 1.4 | 1.5 |
| DL312-SG1 | 1.0 | 1.4 | 1.1 | 0.2 | 1.4 | 1.4 |
| D30316AE02-SG1 | 2.3 | 2.9 | 2.1 | 2.3 | 0.6 | 2.8 |
| D30841AE05-SG1 | 0.9 | -0.1 | 0.8 | 1.1 | 1.3 | 0.0 |
| DLL3-14-SG1 | 1.2 | 1.4 | 1.0 | 1.5 | 1.4 | 1.4 |
| DLL3-22-SG1 | 1.2 | 1.3 | 0.9 | 1.3 | 1.3 | 1.3 |
| DLL3-4-SG1 | 1.2 | 1.3 | 1.0 | 1.3 | 1.3 | 1.3 |
| DLL3-6-SG1 | 1.2 | 1.3 | 1.0 | 1.3 | 1.3 | 1.3 |

CYTOTOXICITY-INDUCING THERAPEUTIC AGENT

CROSS-REFERENCE TO RELATED APPLICATIONS

This application is a divisional of U.S. patent application Ser. No. 16/957,837, 371(c) date Jun. 25, 2020, which is a U.S. National Phase of PCT Application No. PCT/JP2018/048409, filed Dec. 28, 2018, which claims the benefit of Japanese Patent Application No. 2017-254279, filed Dec. 28, 2017, each of which is incorporated herein by reference in its entirety.

REFERENCE TO SEQUENCE LISTING SUBMITTED ELECTRONICALLY

The content of the electronically submitted sequence listing (Name: 6663_0246 Sequence_Listing.xml; Size: 510,787 bytes; and Date of Creation: May 2, 2023) filed with the application is incorporated herein by reference in its entirety.

The present invention relates to multispecific antigen-binding molecules that comprise a first domain comprising a first antigen-binding domain binds to human DLL3 and a second domain comprising a second antigen-binding domain binds to T cell receptor complex, uses thereof, and such. The present invention also relates to novel monospecific antigen-binding molecules that comprise an antigen-binding domain binds to human DLL3, uses thereof, and such.

BACKGROUND ART

Cancer is one of the leading causes of death worldwide. With the exception of certain carcinomas, tumors are often inoperable when they are found. Conventional cancer treatments include radiation therapy, chemotherapy, and immunotherapy. These treatments are often not effective enough and eventually cancer recurrence or metastasis occurs after the treatment. Lack of tumor specificity is one of the factors that limit the maximum efficacy; therefore, more tumor-specific molecular targeted therapy has become an additional viable option in cancer treatment.

Antibodies are drawing attention as pharmaceuticals since they are highly stable in plasma and have few side effects. Among multiple therapeutic antibodies, some types of antibodies require effector cells to exert an anti-tumor response. Antibody dependent cell-mediated cytotoxicity (ADCC) is a cytotoxicity exhibited by effector cells against antibody-bound cells via binding of the Fc region of the antibody to Fc receptors present on NK cells and macrophages. To date, multiple therapeutic antibodies that can induce ADCC to exert anti-tumor efficacy have been developed as pharmaceuticals for treating cancer (NPL 1). Therapies targeting tumor-specific expressed antigens using conventional therapeutic antibodies show excellent anti-tumor activities, while administration of such antibodies could not always lead to satisfactory outcomes.

In addition to the antibodies that adopt ADCC by recruiting NK cells or macrophages as effector cells, T cell-recruiting antibodies (TR antibodies) that adopt cytotoxicity by recruiting T cells as effector cells have been known since the 1980s (NPL 2 to 4). A TR antibody is a bispecific antibody that recognizes and binds to any one of the subunits forming a T-cell receptor complex on T-cells, in particular the CD3 epsilon chain, and an antigen on cancer cells. Several TR antibodies are currently being developed. Catumaxomab, which is a TR antibody against EpCAM, has been approved in the EU for the treatment of malignant ascites. Furthermore, a type of TR antibody called "bispecific T-cell engager (BiTE)" has been recently found to exhibit a strong anti-tumor activity (NPL 5 and 6). Blinatumomab, which is a BiTE molecule against CD19, received FDA approval first in 2014. Blinatumomab has been proved to exhibit a much stronger cytotoxic activity against CD19/CD20-positive cancer cells in vitro compared with Rituximab, which induces antibody-dependent cell-mediated cytotoxicity (ADCC) and complement-dependent cytotoxicity (CDC) (NPL 7).

However, it is known that a trifunctional antibody binds to both a T-cell and a cell such as an NK cell or macrophage at the same time in a cancer antigen-independent manner, and as a result receptors expressed on the cells are cross-linked, and expression of various cytokines is induced in a cancer antigen-independent manner. Systemic administration of a trifunctional antibody is thought to cause cytokine storm-like side effects as a result of such induction of cytokine expression. In fact, it has been reported that, in the phase I clinical trial, a very low dose of 5 micrograms (micro g)/body was the maximum tolerance dose for systemic administration of catumaxomab to patients with non-small cell lung cancer, and that administration of a higher dose causes various severe side effects (NPL 8). When administered at such a low dose, catumaxomab can never reach the effective blood level. That is, the expected anti-tumor effect cannot be achieved by administrating catumaxomab at such a low dose.

Meanwhile, unlike catumaxomab, BiTE has no Fc gamma receptor-binding site, and therefore it does not cross-link the receptors expressed on T-cells and cells such as NK cells and macrophages in a cancer antigen-independent manner. Thus, it has been demonstrated that BiTE does not cause cancer antigen-independent cytokine induction which is observed when catumaxomab is administered. However, since BiTE is a modified low-molecular-weight antibody molecule without an Fc region, the problem is that its blood half-life after administration to a patient is significantly shorter than IgG-type antibodies conventionally used as therapeutic antibodies. In fact, the blood half-life of BiTE administered in vivo has been reported to be about several hours (NPL 9 and 10). In the clinical trials of blinatumomab, it is administered by continuous intravenous infusion using a minipump. This administration method is not only extremely inconvenient for patients but also has the potential risk of medical accidents due to device malfunction or the like. Thus, it cannot be said that such an administration method is desirable.

Delta-like 3 (DLL3) is a type I membrane protein belonging to Notch ligand family members. DLL3 is necessary for normal somite formation and patterning. Mutations in DLL3 cause rib defects or spondylolysis in autosomal recessive spondylocostal dysostosis patients (NPL 11 and 12). There exist previous studies reporting the amplification of the DLL3 gene on chromosome and increased expression of this gene in pancreatic cancer cell lines (NPL 13) and increased DLL3 expression in some glioma cases (NPL 14). In addition, DLL3 has been proposed previously in methods to diagnose and treat glioma, in addition to SCLC, using an ADCC enhanced antibody, antibody-drug conjugate (ADC), and T cell-engaging bispecific molecule using BiTE-Fc format (PTL 1, 2 and 3).

CITATION LIST

Patent Literature

[PTL 1] WO 2011/093097
[PTL 2] WO 2013/126746
[PTL 3] WO 2017/021349

Non-Patent Literature

[NPL 1] Clin Cancer Res. 2010 Jan. 1; 16(1):11-20.
[NPL 2] Nature. 1985 Apr. 18-24; 314(6012):628-31.
[NPL 3] Int J Cancer. 1988 Apr. 15; 41(4):609-15.
[NPL 4] Proc Natl Acad Sci USA. 1986 March; 83(5):1453-7.
[NPL 5] Proc Natl Acad Sci USA. 1995 Jul. 18; 92(15): 7021-5.
[NPL 6] Drug Discov Today. 2005 Sep. 15; 10(18):1237-44.
[NPL 7] Int J Cancer. 2002 Aug. 20; 100(6):690-7.
[NPL 8] Cancer Immunol Immunother (2007) 56 (10), 1637-44.
[NPL 9] Cancer Immunol Immunother. (2006) 55 (5), 503-14.
[NPL 10] Cancer Immunol Immunother. (2009) 58 (1), 95-109.
[NPL 11] Bulman, M. P. et al. (2000) Nat Genet 24, 438-441.
[NPL 12] Turnpenny, P. D. et al. (2003) J Med Genet 40, 333-339.
[NPL 13] Phillips, H. S. (2006) Cancer Cell 9, 157-173.
[NPL 14] Mulledndore, M. E. (2009) Clin Cancer Res 15, 2291-2301.

SUMMARY OF INVENTION

Technical Problem

An objective of the present invention is to provide multispecific antigen-binding molecules that enable cancer treatment by having T cells close to DLL3-expressing cells and using the cytotoxicity of T cells against DLL3-expressing cancer cells, methods for producing the multispecific antigen-binding molecules, and therapeutic agents comprising such a multispecific antigen-binding molecule as an active ingredient for inducing cellular cytotoxicity. Another objective of the present invention is to provide pharmaceutical compositions for use in treating or preventing various cancers, which comprise one of the above-mentioned antigen-binding molecules as an active ingredient, and therapeutic methods using the pharmaceutical compositions. Another objective of the present invention is to provide novel monospecific antigen-binding molecules having human DLL3-binding activity, therapeutic agents comprising such a monospecific antigen-binding molecule as an active ingredient, and therapeutic methods using such a therapeutic agent.

Solution to Problem

The inventors found that multispecific antigen-binding molecules that comprise a first domain comprising a first antigen-binding domain binds to human DLL3, and a second domain comprising a second antigen-binding domain binds to T-cell receptor complex can damage cells expressing DLL3, and exert a superior cytotoxic/antitumor activity. The present invention provides the multispecific antigen-binding molecules and pharmaceutical compositions that can treat various cancers, especially those associated with DLL3 such as DLL3-positive tumors, by comprising the antigen-binding molecule as an active ingredient. The present invention also provides novel monospecific antigen-binding molecules that comprise an antigen-binding domain binds to human DLL3, and pharmaceutical compositions comprising such antigen-binding molecules.

More specifically, the present invention provides the following:

[2] A multispecific antigen-binding molecule that comprises:
(1) a first domain comprising a first antigen-binding domain binds to human DLL3, and
(2) a second domain comprising a second antigen-binding domain binds to T-cell receptor complex,
wherein the first antigen-binding domain of (1) binds to an epitope within the region defined in SEQ ID NO: 7 in human DLL3.

[2] A multispecific antigen-binding molecule that comprises:
(1) a first domain comprising a first antigen-binding domain binds to human DLL3, and
(2) a second domain comprising a second antigen-binding domain binds to T-cell receptor complex,
wherein the first antigen-binding domain of (1) comprises any one of (a1) to (a12) below:
(a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;
(a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;
(a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;
(a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;
(a5) an antibody variable fragment comprising the HVR-H1 sequence of SEQ ID NO: 51, the HVR-H2 sequence of SEQ ID NO: 52, the HVR-H3 sequence of SEQ ID NO: 53, the HVR-L1 sequence of SEQ ID NO: 54, the HVR-L2 sequence of SEQ ID NO: 55, and the HVR-L3 sequence of SEQ ID NO: 56;
(a6) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a7) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a8) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;

(a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;

(a10) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;

(a11) an antibody variable fragment that binds to the same epitope of any of the antibody variable fragment selected from (a1) to (a10);

(a12) an antibody variable fragment that competes with the binding of any of the antibody variable fragment selected from (a1) to (a10).

[3] A multispecific antigen-binding molecule that comprises:

(1) a first domain comprising a first antigen-binding domain binds to human DLL3, and (2) a second domain comprising a second antigen-binding domain binds to T-cell receptor complex, wherein the first antigen-binding domain of (1) comprises any one of (b1) to (b21) below:

(b1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(b2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(b3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(b4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(b5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(b6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(b7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(b8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(b9) an antibody variable fragment comprising the HVR-H1 sequence identical to the amino acid sequences of the HVR-H1 region comprised in SEQ ID NO: 85, the HVR-H2 sequence identical to the amino acid sequences of the HVR-H2 region comprised in SEQ ID NO: 85, the HVR-H3 sequence identical to the amino acid sequences of the HVR-H3 region comprised in SEQ ID NO: 85, the HVR-L1 sequence identical to the amino acid sequences of the HVR-L1 region comprised in SEQ ID NO: 93, the HVR-L2 sequence identical to the amino acid sequences of the HVR-L2 region comprised in SEQ ID NO: 93, and the HVR-L3 sequence identical to the amino acid sequences of the HVR-L3 region comprised in SEQ ID NO: 93;

(b10) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b11) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b12) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b13) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b15) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(b16) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b17) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b18) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b19) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b20) an antibody variable fragment that binds to the same epitope of any one of the antibody variable fragment selected from (b1) to (b19);

(b21) an antibody variable fragment that competes with the binding of any one of the antibody variable fragment selected from (b1) to (b19).

[4] A multispecific antigen-binding molecule that comprises:

(1) a first domain comprising a first antigen-binding domain binds to human DLL3, and (2) a second domain comprising a second antigen-binding domain binds to T-cell receptor complex, wherein the first antigen-binding domain of (1) comprises any one of the combinations of heavy chain variable region and light chain variable region selected from the following (c1) to (c22):

(c1) heavy chain variable region having the amino acid sequence of SEQ ID NO: 15 and light chain variable region having the amino acid sequence of SEQ ID NO: 16;

(c2) heavy chain variable region having the amino acid sequence of SEQ ID NO: 25 and light chain variable region having the amino acid sequence of SEQ ID NO: 26;

(c3) heavy chain variable region having the amino acid sequence of SEQ ID NO: 19 and light chain variable region having the amino acid sequence of SEQ ID NO: 20;

(c4) heavy chain variable region having the amino acid sequence of SEQ ID NO: 23 and light chain variable region having the amino acid sequence of SEQ ID NO: 24;

(c5) heavy chain variable region having the amino acid sequence of SEQ ID NO: 11 and light chain variable region having the amino acid sequence of SEQ ID NO: 12;

(c6) heavy chain variable region having the amino acid sequence of SEQ ID NO: 13 and light chain variable region having the amino acid sequence of SEQ ID NO: 14;

(c7) heavy chain variable region having the amino acid sequence of SEQ ID NO: 17 and light chain variable region having the amino acid sequence of SEQ ID NO: 18;

(c8) heavy chain variable region having the amino acid sequence of SEQ ID NO: 21 and light chain variable region having the amino acid sequence of SEQ ID NO: 22;

(c9) heavy chain variable region having the amino acid sequence of SEQ ID NO: 85 and light chain variable region having the amino acid sequence of SEQ ID NO: 93;

(c10) heavy chain variable region having the amino acid sequence of SEQ ID NO: 63 and light chain variable region having the amino acid sequence of SEQ ID NO: 72;

(c11) heavy chain variable region having the amino acid sequence of SEQ ID NO: 64 and light chain variable region having the amino acid sequence of SEQ ID NO: 72;

(c12) heavy chain variable region having the amino acid sequence of SEQ ID NO: 65 and light chain variable region having the amino acid sequence of SEQ ID NO: 72;

(c13) heavy chain variable region having the amino acid sequence of SEQ ID NO: 66 and light chain variable region having the amino acid sequence of SEQ ID NO: 73;

(c14) heavy chain variable region having the amino acid sequence of SEQ ID NO: 67 and light chain variable region having the amino acid sequence of SEQ ID NO: 73;

(c15) heavy chain variable region having the amino acid sequence of SEQ ID NO: 67 and light chain variable region having the amino acid sequence of SEQ ID NO: 74;

(c16) heavy chain variable region having the amino acid sequence of SEQ ID NO: 68 and light chain variable region having the amino acid sequence of SEQ ID NO: 72;

(c17) heavy chain variable region having the amino acid sequence of SEQ ID NO: 69 and light chain variable region having the amino acid sequence of SEQ ID NO: 73;

(c18) heavy chain variable region having the amino acid sequence of SEQ ID NO: 70 and light chain variable region having the amino acid sequence of SEQ ID NO: 73;

(c19) heavy chain variable region having the amino acid sequence of SEQ ID NO: 71 and light chain variable region having the amino acid sequence of SEQ ID NO: 73;

(c20) a heavy chain variable region that has an identity more than 80% of any one of the heavy chain variable region of (c1) to (c19), and a light chain variable region that has an identity more than 80% to any one of the light chain variable region of (c1) to (c19);

(c21) a heavy chain variable region that has an identity more than 90% of any one of the heavy chain variable region of (c1) to (c19), and a light chain variable region that has an identity more than 90% to any one of the light chain variable region of (c1) to (c19);

(c22) a heavy chain variable region that has an identity more than 95% of any one of the heavy chain variable region of (c1) to (c19), and a light chain variable region that has an identity more than 95% to any one of the light chain variable region of (c1) to (c19).

[5] The multispecific antigen-binding molecule of any one of [1] to [4], wherein the multispecific antigen-binding molecule has cytotoxic activity.

[6] The multispecific antigen-binding molecule of [5], wherein the cytotoxic activity is T-cell-dependent cytotoxic activity.

[7] The multispecific antigen-binding molecule of any one of [1] to [6], wherein the second antigen-binding domain in (2) binds to CD3 epsilon chain.

[8] The multispecific antigen-binding molecule of any one of [1] to [6], wherein the second antigen-binding domain in (2) binds to T-cell receptor.

[9] The multispecific antigen-binding molecule of any one of [1] to [8], wherein the second antigen-binding domain in (2) comprises any one of (d1) to (d12) below:

(d1) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 57 respectively, and the HVR-L1, HVR-L2 and HVR-L3 sequences identical to the amino acid sequences of the HVR-L1, HVR-L2 and HVR-L3 regions comprised in SEQ ID NO: 58 respectively;

(d2) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 98 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d3) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 99 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d4) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 100 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d5) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 101 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d6) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 102 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d7) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 298 respectively, and the HVR-L1, HVR-L2 and HVR-L3 sequences identical to the amino acid sequences of the HVR-L1, HVR-L2 and HVR-L3 regions comprised in SEQ ID NO: 299 respectively;

(d8) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 300 respectively, and the HVR-L1, HVR-L2 and HVR-L3 sequences identical to the amino acid sequences of the HVR-L1, HVR-L2 and HVR-L3 regions comprised in SEQ ID NO: 301 respectively;

(d9) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 302 respectively, and the HVR-L1, HVR-L2 and HVR-L3 sequences identical to the amino acid sequences of the HVR-L1, HVR-L2 and HVR-L3 regions comprised in SEQ ID NO: 303 respectively;

(d10) an antibody variable fragment comprising the HVR-H1, HVR-H2 and HVR-H3 sequences identical to the amino acid sequences of the HVR-H1, HVR-H2 and HVR-H3 regions comprised in any one selected from SEQ ID NO: 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388 and 390, and the HVR-L1, HVR-L2 and HVR-L3 sequences identical to the amino acid sequences of the HVR-L1, HVR-L2 and HVR-L3 regions comprised in any one selected from SEQ ID NO: 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389 and 391;

(d11) an antibody variable fragment that binds to the same epitope of any one of the antibody variable fragment selected from (d1) to (d10);

(d12) an antibody variable fragment that competes with the binding of any one of the antibody variable fragment selected from (d1) to (d10).

[10] The multispecific antigen-binding molecule of any one of [1] to [8], wherein the second antigen-binding domain in (2) comprises any one of (e1) to (e12) below:

(e1) heavy chain variable region having the amino acid sequence of SEQ ID NO: 57 and light chain variable region having the amino acid sequence of SEQ ID NO: 58;

(e2) heavy chain variable region having the amino acid sequence of SEQ ID NO: 98 and light chain variable region having the amino acid sequence of SEQ ID NO: 103;

(e3) heavy chain variable region having the amino acid sequence of SEQ ID NO: 99 and light chain variable region having the amino acid sequence of SEQ ID NO: 103;

(e4) heavy chain variable region having the amino acid sequence of SEQ ID NO: 100 and light chain variable region having the amino acid sequence of SEQ ID NO: 103;

(e5) heavy chain variable region having the amino acid sequence of SEQ ID NO: 101 and light chain variable region having the amino acid sequence of SEQ ID NO: 103;

(e6) heavy chain variable region having the amino acid sequence of SEQ ID NO: 102 and light chain variable region having the amino acid sequence of SEQ ID NO: 103;

(e7) heavy chain variable region having the amino acid sequence of SEQ ID NO: 300 and light chain variable region having the amino acid sequence of SEQ ID NO: 301;

(e8) heavy chain variable region having the amino acid sequence of SEQ ID NO: 302 and light chain variable region having the amino acid sequence of SEQ ID NO: 303;

(e9) heavy chain variable region and light chain variable region having any one of the amino acid sequence combination in Table 2A;

(e10) a heavy chain variable region that has an identity more than 80% of any one of the heavy chain variable region of (e1) to (e9), and a light chain variable region that has an identity more than 80% to any one of the light chain variable region of (e1) to (e9);

(e11) a heavy chain variable region that has an identity more than 90% of any one of the heavy chain variable region of (e1) to (e9), and a light chain variable region that has an identity more than 90% to any one of the light chain variable region of (e1) to (e9);

(e12) a heavy chain variable region that has an identity more than 95% of any one of the heavy chain variable region of (e1) to (e9), and a light chain variable region that has an identity more than 95% to any one of the light chain variable region of (e1) to (e9).

[11] The multispecific antigen-binding molecule of any one of [1] to [8], wherein the second antigen-binding domain in (2) comprises any one of (j1) to (j5) below:

(j1) an antibody variable fragment comprising the HVR-H1 sequence of SEQ ID NO: 136, the HVR-H2 sequence of SEQ ID NO: 137, the HVR-H3 sequence of SEQ ID NO: 138, the HVR-L1 sequence of SEQ ID NO: 139, the HVR-L2 sequence of SEQ ID NO: 140, and the HVR-L3 sequence of SEQ ID NO: 141;

(j2) an antibody variable fragment comprising the HVR-H1 sequence of SEQ ID NO: 142, the HVR-H2 sequence of SEQ ID NO: 143, the HVR-H3 sequence of SEQ ID NO: 144, the HVR-L1 sequence of SEQ ID NO: 145, the HVR-L2 sequence of SEQ ID NO: 146, and the HVR-L3 sequence of SEQ ID NO: 147;

(j3) an antibody variable fragment comprising the HVR sequences selected from any of the combinations in Table 2B;

(j4) an antibody variable fragment that binds to the same epitope of any of the antibody variable fragment selected from (j1) to (j3);

(j5) an antibody variable fragment that competes with the binding of any of the antibody variable fragment selected from (j1) to (j3).

[12] The multispecific antigen binding molecule of any one of [1] to [111], wherein the first antigen-binding domain or the second antigen-binding domain is an antibody variable fragment, or both of the first and second antigen-binding domains are antibody variable fragments.

[13] The multispecific antigen binding molecule of [12], wherein the antibody variable fragment is a Fab.

[14] The multispecific antigen binding molecule of any one of [1] to [13], wherein the multispecific antigen binding molecule further comprises:

(3) a third domain comprising an Fc region with reduced binding activity towards an Fc gamma receptor.

[15] A multispecific antigen-binding molecule that comprises:

(1) a first domain comprising a first antigen-binding domain binds to human DLL3, (2) a second domain comprising a second antigen-binding domain binds to T-cell receptor complex, and (3) a third domain comprising an Fc region with reduced binding activity towards an Fc gamma receptor.

[16] The multispecific antigen binding molecule of [15], wherein the first antigen-binding domain or the second antigen-binding domain is an antibody variable fragment, or both of the first and second antigen-binding domains are antibody variable fragments.

[17] The multispecific antigen binding molecule of [16], wherein the antibody variable fragment is a Fab.

[18] The multispecific antigen-binding molecule of any one of [14] to [17], wherein the Fc region of is an Fc region with an amino acid mutation at any of the Fc region-constituting amino acids of SEQ ID NOs: 112 to 115 (IgG1 to IgG4).

[19] The multispecific antigen-binding molecule of [18], wherein the Fc region is an Fc region with mutation of at least one amino acid selected from the following amino acid positions specified by EU numbering:

position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

[20] The multispecific antigen-binding molecule of any one of [1] to [19], wherein the multispecific antigen-binding molecule is a bispecific antibody.

[21] The bispecific antibody of [20], wherein the antibody is a monoclonal antibody.

[22] A pharmaceutical composition comprising the multispecific antigen-binding molecule of any one of [1] to [19] or the bispecific antibody of [20] or [21], and a pharmaceutically acceptable carrier.

[23] The pharmaceutical composition of [22], which induces T-cell-dependent cytotoxicity.

[24] A pharmaceutical composition for use in treating or preventing cancer, which comprises the multispecific antigen-binding molecule of any one of [1] to [19] or the bispecific antibody of [20] or [21].

[25] A method for treating or preventing cancer, which comprises administering the antigen-binding molecule of any one of [1] to [19] or the bispecific antibody of [20] or [21] to a patient in need thereof.

[26] Use of the antigen-binding molecule of any one of [1] to [19] or the bispecific antibody of [20] or [21] in the manufacture of a pharmaceutical composition for treating or preventing cancer.

[27] Use of the antigen-binding molecule of any one of [1] to [19] or the bispecific antibody of [20] or [21] for treating or preventing cancer.

[28] The method of [25], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[29] The use of [26] or [27], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[30] The pharmaceutical composition of [24], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[31] An antigen-binding molecule that binds to an epitope within the region defined in SEQ ID NO: 7 in human DLL3.

[32] An antigen-binding molecule that comprises an antigen-binding domain comprising any one of (f1) to (f11) below:

(f1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;

(f3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;

(f4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;

(f5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;

(f8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;

(f9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;

(f10) an antibody variable fragment that binds to the same epitope of any of the antibody variable fragment selected from (f1) to (f9);

(f11) an antibody variable fragment that competes with the binding of any of the antibody variable fragment selected from (f1) to (f9).

[33] An antigen-binding molecule that comprises an antigen-binding domain comprising any one of (g1) to (g20) below:

(g1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(g2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(g3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(g4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(g5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(g6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(g7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(g8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(g9) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g10) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g11) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g12) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g13) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(g15) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g16) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g17) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g18) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g19) an antibody variable fragment that binds to the same epitope of any one of the antibody variable fragment selected from (g1) to (g18);

(g20) an antibody variable fragment that competes with the binding of any one of the antibody variable fragment selected from (g1) to (g18).

[34] An antigen-binding molecule that comprises an antigen-binding domain comprises any one of (h1) to (h21) below:

(h1) heavy chain variable region having the amino acid sequence of SEQ ID NO: 15 and light chain variable region having the amino acid sequence of SEQ ID NO: 16;

(h2) heavy chain variable region having the amino acid sequence of SEQ ID NO: 25 and light chain variable region having the amino acid sequence of SEQ ID NO: 26;

(h3) heavy chain variable region having the amino acid sequence of SEQ ID NO: 19 and light chain variable region having the amino acid sequence of SEQ ID NO: 20;

(h4) heavy chain variable region having the amino acid sequence of SEQ ID NO: 23 and light chain variable region having the amino acid sequence of SEQ ID NO: 24;

(h5) heavy chain variable region having the amino acid sequence of SEQ ID NO: 11 and light chain variable region having the amino acid sequence of SEQ ID NO: 12;

(h6) heavy chain variable region having the amino acid sequence of SEQ ID NO: 13 and light chain variable region having the amino acid sequence of SEQ ID NO: 14;

(h7) heavy chain variable region having the amino acid sequence of SEQ ID NO: 17 and light chain variable region having the amino acid sequence of SEQ ID NO: 18;

(h8) heavy chain variable region having the amino acid sequence of SEQ ID NO: 21 and light chain variable region having the amino acid sequence of SEQ ID NO: 22;

(h9) heavy chain variable region having the amino acid sequence of SEQ ID NO: 63 and light chain variable region having the amino acid sequence of SEQ ID NO: 72;

(h10) heavy chain variable region having the amino acid sequence of SEQ ID NO: 64 and light chain variable region having the amino acid sequence of SEQ ID NO: 72;

(h11) heavy chain variable region having the amino acid sequence of SEQ ID NO: 65 and light chain variable region having the amino acid sequence of SEQ ID NO: 72;

(h12) heavy chain variable region having the amino acid sequence of SEQ ID NO: 66 and light chain variable region having the amino acid sequence of SEQ ID NO: 73;

(h13) heavy chain variable region having the amino acid sequence of SEQ ID NO: 67 and light chain variable region having the amino acid sequence of SEQ ID NO: 73;

(h14) heavy chain variable region having the amino acid sequence of SEQ ID NO: 67 and light chain variable region having the amino acid sequence of SEQ ID NO: 74;

(h15) heavy chain variable region having the amino acid sequence of SEQ ID NO: 68 and light chain variable region having the amino acid sequence of SEQ ID NO: 72;

(h16) heavy chain variable region having the amino acid sequence of SEQ ID NO: 69 and light chain variable region having the amino acid sequence of SEQ ID NO: 73;

(h17) heavy chain variable region having the amino acid sequence of SEQ ID NO: 70 and light chain variable region having the amino acid sequence of SEQ ID NO: 73;

(h18) heavy chain variable region having the amino acid sequence of SEQ ID NO: 71 and light chain variable region having the amino acid sequence of SEQ ID NO: 73;

(h19) a heavy chain variable region that has an identity more than 80% of any one of the heavy chain variable region of (h1) to (h18); and a light chain variable region that has an identity more than 80% to any one of the light chain variable region of (h1) to (h18);

(h20) a heavy chain variable region that has an identity more than 90% of any one of the heavy chain variable region of (h1) to (h18); and a light chain variable region that has an identity more than 90% to any one of the light chain variable region of (h1) to (h18);

(h21) a heavy chain variable region that has an identity more than 95% of any one of the heavy chain variable region of (h1) to (h18); and a light chain variable region that has an identity more than 95% to any one of the light chain variable region of (h1) to (h18).

[35] The antigen-binding molecule of any one of [31] to [34], wherein the antigen-binding molecule has cellular cytotoxic activity.

[36] The antigen-binding molecule of [35], wherein the cytotoxic activity is antibody dependent cellular cytotoxicity or complement dependent cytotoxicity.

[37] The antigen-binding molecule of any one of [31] to [36], wherein the antigen-binding molecule has internalization activity.

[38] The antigen-binding molecule of any one of [31] to [37], wherein the antigen-binding molecule is conjugated to a toxic compound.

[39] The antigen binding molecule of any one of [31] to [38], wherein the antigen-binding domain is an antibody variable fragment.

[40] The antigen binding molecule of [39], wherein the antibody variable fragment is a Fab.

[41] The antigen-binding molecule of any one of [31] to [40], wherein the antigen-binding molecule is an antibody.

[42] The antigen-binding molecule of [41], wherein the antigen-binding molecule is a monoclonal antibody.

[43] An antibody-drug-conjugate compound that comprises the antibody of [42].

[44] A pharmaceutical composition comprising the antigen-binding molecule of any one of [31] to [40] or the antibody of [41] or [42], and a pharmaceutically acceptable carrier.

[45] A pharmaceutical composition for use in treating or preventing cancer, which comprises the antigen-binding molecule of any one of [31] to [40] or the antibody of [41] or [42].

[46] A method for treating or preventing cancer, which comprises administering the antigen-binding molecule of any one of [31] to [40] or the antibody of [41] or [42] to a patient in need thereof.

[47] Use of the antigen-binding molecule of any one of [31] to [40] or the antibody of [41] or [42] in the manufacture of a pharmaceutical composition for treating or preventing cancer.

[48] Use of the antigen-binding molecule of any one of [31] to [40] or the antibody of [41] or [42] for treating or preventing cancer.

[49] The method of [46], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[50] The use of [47] or [48], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[51] The pharmaceutical composition of [45], wherein the cancer is lung cancer (including small cell lung cancer), breast cancer, cervical cancer, colon cancer, colorectal cancer, endometrial cancer, head and neck cancer, liver cancer, ovarian cancer, pancreatic cancer, prostate cancer, skin cancer, gastric cancer, testis cancer, thyroid cancer, adrenal cancer, renal cancer, bladder cancer, uterine cancer, esophageal cancer, urothelial cancer, brain cancer, lymphoma, carcinoma or sarcoma.

[52] A kit comprising the antigen-binding molecule of any one of [1] to [19] or the bispecific antibody of [20] or [21], and instructions for use.

[53] A kit comprising the antigen-binding molecule of any one of [31] to [40] or the antibody of [41] or [42], and instructions for use.

Advantageous Effects of Invention

The present invention provides multispecific antigen-binding molecules that enable cancer treatment by having T-cells close to DLL3-expressing cells and using the cytotoxicity of T-cells against the DLL3-expressing cancer cells, methods for producing the multispecific antigen-binding molecules, and therapeutic agents containing such a multispecific antigen-binding molecule as an active ingredient for inducing cellular cytotoxicity, as a new approach of cancer treatment. Multispecific antigen-binding molecules of the present invention have strong anti-tumor activity, inducing cellular cytotoxicity, and can target and damage DLL3-expressing cells, thus enable treatment and prevention of various cancers. The present invention also provides novel monospecific antigen-binding molecules having human DLL3-binding activity, therapeutic agents comprising such a monospecific antigen-binding molecule as an active ingredient, and therapeutic methods using such a therapeutic agent.

BRIEF DESCRIPTION OF DRAWINGS

FIG. 8 shows competition ratio of Antibody B to Antibody A.

DESCRIPTION OF EMBODIMENTS

Figure 1:
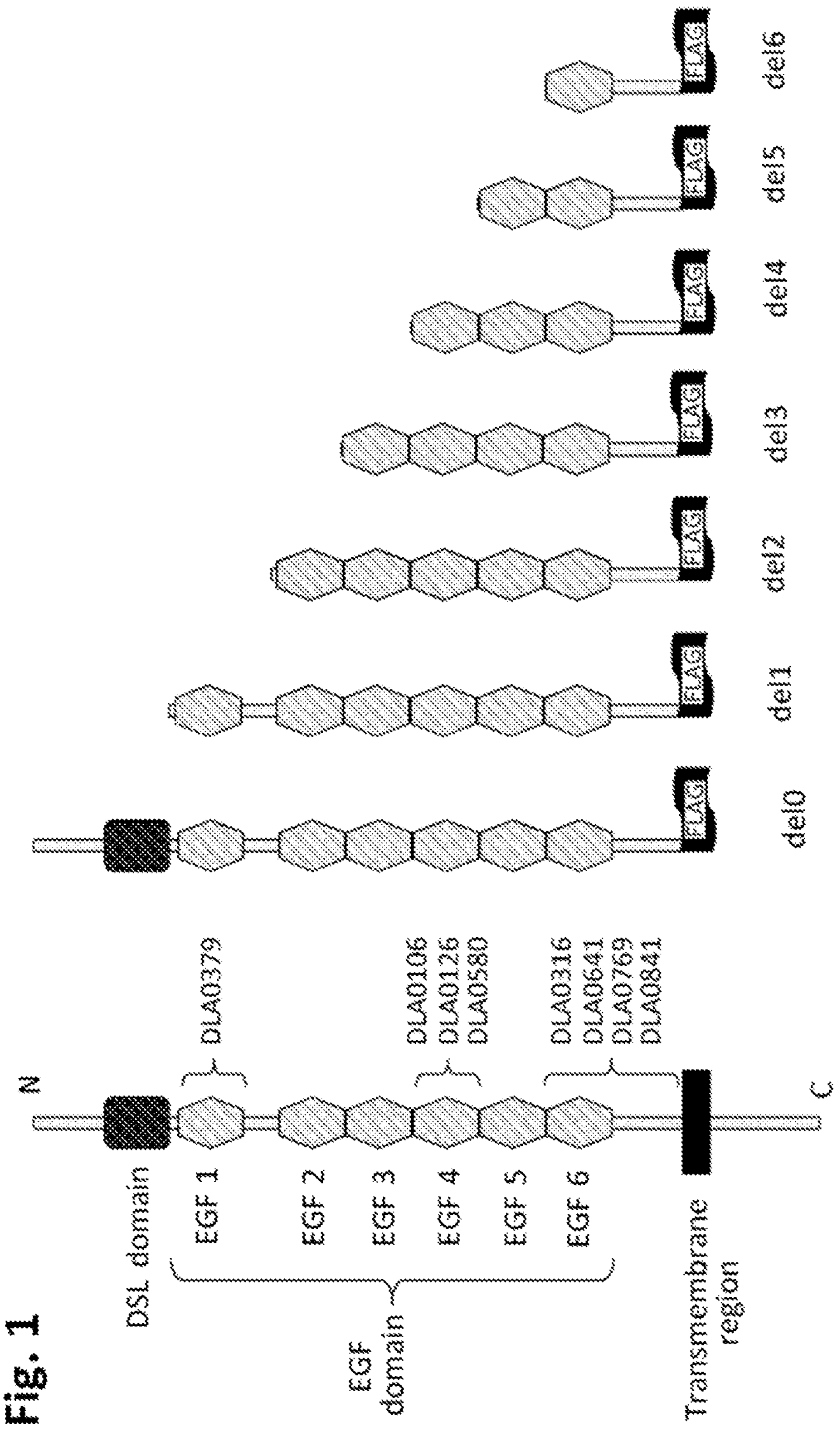
FIG. 1 is a schematic drawing showing the structures of the full-length human DLL3 and human DLL3 ECD fragment proteins prepared in Example 1. The epitope recognized by each of the anti-DLL3 antibodies selected in Example 3 is also shown. The EGF domain has six regions, EGF1 to EGF6 from the N-terminal side to the C-terminal side.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The definitions and detailed description below are provided to facilitate understanding of the present invention illustrated herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Amino Acids

Herein, amino acids are described by one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alteration in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to non-natural amino acids (Annu Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has a non-natural amino acid bound to a complementary amber suppressor tRNA of one of the stop codons, the UAG codon (amber codon).

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid alterations: amino acid(s) at (a) position 33, (b) position 55, (c) position 96, (d) positions 33 and 55, (e) positions 33 and 96, (f) positions 55 and 96, and (g) positions 33, 55, and 96.

Furthermore, herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Antigen-Binding Molecule

The term "antigen-binding molecules", as used herein, refers to any molecule that comprises an antigen-binding domain, and may further refers to molecules such as a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such.

A favorable example of an antigen-binding molecule of the present invention is an antigen-binding molecule that comprises a plurality of antigen-binding domains. In certain embodiments, the antigen-binding molecule of the present invention is an antigen-binding molecule that comprises two antigen-binding domains with different antigen-binding specificities. In certain embodiments, the antigen-binding molecule of the present invention is an antigen-binding molecule that comprises two antigen-binding domains with different antigen-binding specificities, and an FcRn-binding domain contained in an antibody Fc region. As a method for extending the blood half-life of a protein administered to a living body, the method of adding an FcRn-binding domain of an antibody to the protein of interest and utilizing the function of FcRn-mediated recycling is well known.

Another favorable example of an antigen-binding molecule of the present invention is an antigen-binding molecule that comprises only one type of antigen-binding domains. In certain embodiments, the antigen-binding molecule of the present invention is an antigen-binding molecule that comprises two antigen-binding domains with the same antigen-binding specificity. In certain embodiments, the antigen-binding molecule of the present invention is an antigen-binding molecule that comprises two antigen-binding domains with the same antigen-binding specificity, and an Fc region.

Antigen-Binding Domain

The term "antigen-binding domain", as used herein, refers to an antibody portion which comprises a region that specifically binds and is complementary to the whole or a portion of an antigen. When the molecular weight of an antigen is large, an antibody can only bind to a particular portion of the antigen. The particular portion is called "epitope". An antigen-binding domain can be provided from one or more antibody variable domains. Preferably, the antigen-binding domains contain both the antibody light chain variable region (VL) and antibody heavy chain variable region (VH). Such preferable antigen-binding domains include, for example, "single-chain Fv (scFv)", "single-chain antibody", "Fv", "single-chain Fv2 (scFv2)", "Fab", and "F (ab')2".

The antigen-binding domains of antigen-binding molecules of the present invention may bind to the same epitope. The epitope can be present in a protein comprising the amino acid sequence of SEQ ID NO: 9 or 111. Alternatively, the antigen-binding domains of multispecific antigen-binding molecules of the present invention may individually bind to different epitopes. The epitope can be present in a protein comprising the amino acid sequence of SEQ ID NO: 9 or 111.

The antigen-binding domain of an antigen-binding molecule of the present invention "binds to DLL3 or T cell receptor complex". That is, DLL3 and a T cell receptor complex are preferable antigens of interest. As used herein, the phrase "binds to an antigen" refers to the binding activity of an antigen-binding domain, antibody, antigen-binding molecule, antibody variable fragment, or such (hereinafter, "antigen-binding domain or such") to bind to an antigen of interest at a level of specific binding higher than the level of non-specific or background binding. In other words, such an antigen-binding domain or such "binds to the antigen specifically/significantly" towards the antigen of interest. The specificity can be measured by any methods for detecting affinity or binding activity as mentioned herein or known in the art. The above-mentioned level of specific binding may be high enough to be recognized by a skilled person as being significant. For example, when a skilled person can detect or observe any significant or relatively strong signals or values of binding between the antigen-binding domain or such and the antigen of interest in a suitable binding assay, it can be said that the antigen-binding domain or such "binds to the antigen specifically/significantly" towards the antigen of interest. Sometimes, the phrase "binds to an antigen" has substantially the same meaning as the phrase "binds to an antigen specifically/significantly" in the art.

DLL3

The term "DLL3", as used herein, refers to any native DLL3 (Delta-like 3) from any vertebrate source, including mammals such as primates (e.g. humans) and rodents (e.g., mice and rats), unless otherwise indicated. The term encompasses "full-length" unprocessed DLL3 as well as any form of DLL3 that results from processing in the cell. The term also encompasses naturally occurring variants of DLL3, e.g., splice variants or allelic variants. The amino acid sequence of an exemplary human DLL3 is known as NCBI Reference Sequence (RefSeq) NM_016941.3, and the amino acid sequence of an exemplary cynomolgus DLL3 is known as NCBI Reference Sequence XP_005589253.1, and the amino acid sequence of an exemplary mouse DLL3 is known as NCBI Reference Sequence NM_007866.2. The amino acid sequence of cynomolgus DLL3 used in the working examples is shown in SEQ ID NO: 8.

The human DLL3 protein comprises a transmembrane (TM) region and an intracellular domain on the C-terminal side, and a DSL (Notch) domain on the N-terminal side (see, e.g., FIG. 1). In addition, DLL3 has an EGF domain comprising six regions, EGF1 to EGF6 from the N-terminal side to the C-terminal side. In some embodiments, the antigen-binding molecules or antibodies of the present invention bind to an epitope within the extracellular domain (ECD), i.e., the domain from the N-terminus to immediately before the TM region, but not to the TM region or the C-terminal intracellular domain. The molecules/antibodies of the present invention may bind to an epitope within any of the above-mentioned domains/regions within the ECD. In preferred embodiments, the molecules/antibodies of the present invention bind to an epitope within the region from EGF6 to immediately before the TM region. More specifically, the molecules/antibodies of the present invention may bind to an epitope within the regions defined in SEQ ID NO: 7 in human DLL3. In some embodiments, the molecules/antibodies of the present invention bind to the EGF1, EGF2, EGF3, EGF4, EGF5, or EGF6 region or a region from EGF6 to immediately before the TM region of human DLL3, or an epitope within the EGF1, EGF2, EGF3, EGF4, EGF5, or EGF6 region or a region from EGF6 to immediately before the TM region of human DLL3.

In human DLL3, the above-mentioned domains/regions have the following amino acid residues (see, e.g., www uniprot_org_uniprot/Q9NYJ7 or WO2013/126746):

Extracellular domain (ECD): amino acid residues at positions 1 to 492;

DSL domain: amino acid residues at positions 176 to 215;

EGF domain: amino acid residues at positions 216 to 465;

EGF1 region: amino acid residues at positions 216 to 249;

EGF2 region: amino acid residues at positions 274 to 310;

EGF3 region: amino acid residues at positions 312 to 351;

EGF4 region: amino acid residues at positions 353 to 389;

EGF5 region: amino acid residues at positions 391 to 427;

EGF6 region: amino acid residues at positions 429 to 465;

The region from EGF6 to immediately before the TM region: amino acid residues at positions 429 to 492;

TM region: amino acid residues at positions 493 to 513; and

C-terminal intracellular domain: amino acid residues at positions 516 to 618 (or 516 to 587 in some isoforms). The amino acid positions mentioned above also refers to the amino acid positions in the amino acid sequence shown in SEQ ID NO: 9.

Thus, the antigen-binding molecules or antibodies of the present invention may bind to an above-mentioned region/domain having the amino acid residues at the above-mentioned positions in human DLL3. That is, the antigen-binding molecules or antibodies of the present invention may bind to an epitope within the above-mentioned region/domain having the amino acid residues at the above-mentioned positions in human DLL3.

In some embodiments, due to their specificity, the antigen-binding molecules/antibodies of the present invention do not specifically bind to an above-mentioned region/domain of human DLL3, or an epitope within an above-mentioned region/domain of human DLL3. In some embodiments, the molecules/antibodies of the present invention do not specifically bind to an above-mentioned region/domain having the amino acid residues at the above-mentioned positions in human DLL3. In some embodiments, the molecules/antibodies of the present invention do not specifically bind to an epitope within the above-mentioned region/domain having the amino acid residues at the above-mentioned positions in human DLL3. In this context, the "specifically" may be reworded as "substantially".

The phrase "specifically bind to", as used herein, refers to activity of an antigen-binding molecule/antibody to bind to an antigen/region/domain/epitope of interest at a level of binding that includes specific binding. The phrase "not specifically bind to", as used herein, refers to activity of an antigen-binding molecule/antibody to bind to an antigen/region/domain/epitope of no interest at a level of binding that includes non-specific or background binding but does not include specific binding. The specificity can be measured by any methods mentioned in this specification or known in the art, e.g., epitope mapping or competition assay described herein. The above-mentioned level of non-specific or background binding may be zero, or may not be zero but near zero, or may be very low enough to be technically neglected by those skilled in the art. For example, when a skilled person cannot detect or observe any significant or relatively strong signal for binding between the molecule/antibody and the antigen/region/domain/epitope of no interest in a suitable binding assay, it can be said that the molecule/antibody does "not specifically bind to" the antigen/region/domain/epitope of no interest. Sometimes, the phrase "not specifically bind to" has substantially the same meaning as the phrase "not bind to" in the art.

The DLL3 protein used in the present invention may be a DLL3 protein having the sequence described above or may be a modified protein having a sequence derived from the sequence described above by the modification of one or more amino acids. Examples of the modified protein having a sequence derived from the sequence described above by the modification of one or more amino acids can include polypeptides having 70% or more, preferably 80% or more, more preferably 90% or more, even more preferably 95% or more identity with to the amino acid sequence described above. Alternatively, partial peptides of these DLL3 proteins may be used.

The DLL3 protein used in the present invention is not limited by its origin and is preferably a human or cynomolgus DLL3 protein.

In some embodiments, for the DLL3 protein, DLL3 ECD fragment proteins (or ECD variants) may be used. Depending on the site of truncation, the fragments/variants may comprise, from the N-terminal side to the C-terminal side, the DSL domain to EGF6, EGF1 to EGF6, EGF2 to EGF6, EGF3 to EGF6, EGF4 to EGF6, EGF5 and EGF6, or EGF6. The fragments/variants may further comprise a region spanning from immediately after the EGF6 region to immediately before the TM region. A Flag tag may be attached to the C terminus of the fragments/variants using a technique well-known in the art.

Affinity

"Affinity" refers to the strength of the sum total of noncovalent interactions between a single binding site of a molecule (e.g., an antigen-binding molecule or antibody) and its binding partner (e.g., an antigen). Unless indicated otherwise, as used herein, "binding affinity" refers to intrinsic binding affinity which reflects a 1:1 interaction between members of a binding pair (e.g., antigen-binding molecule and antigen, or antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

Methods to Determine Affinity

In certain embodiments, the antigen-binding domain of an antigen-binding molecule or antibody provided herein has a dissociation constant (Kd) of 1 micro M or less, 120 nM or less, 100 nM or less, 80 nM or less, 70 nM or less, 50 nM or less, 40 nM or less, 30 nM or less, 20 nM or less, 10 nM or less, 2 nM or less, 1 nM or less, 0.1 nM or less, 0.01 nM or less, or 0.001 nM or less (e.g., $10^{-8}$ M or less, $10^{-8}$ M to $10^{-13}$ M, $10^{-9}$ M to $10^{-13}$ M) for its antigen. In certain embodiments, the Kd value of the first antigen-binding domain of the antibody/antigen-binding molecule for DLL3 falls within the range of 1-40, 1-50, 1-70, 1-80, 30-50, 30-70, 30-80, 40-70, 40-80, or 60-80 nM.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc

#269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro L/well of scintillant (MICROSCINT-20™. Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, NJ) is performed at 25 degrees C. with immobilized antigen CM5 chips at approximately 10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (approximately 0.2 micro M) before injection at a flow rate of 5 micro L/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro L/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Methods for measuring the affinity of the antigen-binding domain of an antibody are described above, and one skilled in art can carry out affinity measurement for other antigen-binding domains.

Antibody

The term "antibody" herein is used in the broadest sense and encompasses various antibody structures, including but not limited to monoclonal antibodies, polyclonal antibodies, monospecific antibodies, multispecific antibodies (e.g., bispecific antibodies), and antibody fragments so long as they exhibit the desired antigen-binding activity.

In an aspect, the present invention provides a multispecific antigen-binding molecule or antibody.

In some embodiments, the multispecific antigen-binding molecule comprises:

(1) a first domain comprising a first antigen-binding domain binds to human DLL3, and (2) a second domain comprising a second antigen-binding domain binds to T-cell receptor complex, wherein the first antigen-binding domain of (1) binds to an epitope within the region defined in SEQ ID NO: 7 in human DLL3.

In some embodiments, in the multispecific antigen-binding molecule, the first antigen-binding domain of (1) is any one of (a1) to (a12) below:

(a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;

(a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;

(a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;

(a5) an antibody variable fragment comprising the HVR-H1 sequence of SEQ ID NO: 51, the HVR-H2 sequence of SEQ ID NO: 52, the HVR-H3 sequence of SEQ ID NO: 53, the HVR-L1 sequence of SEQ ID NO: 54, the HVR-L2 sequence of SEQ ID NO: 55, and the HVR-L3 sequence of SEQ ID NO: 56;

(a6) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a7) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a8) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;

(a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;

(a10) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;

(a11) an antibody variable fragment that binds to the same epitope of any of the antibody variable fragment selected from (a1) to (a10);

(a12) an antibody variable fragment that competes with the binding of any of the antibody variable fragment selected from (a1) to (a10).

In some embodiments, in the multispecific antigen-binding molecule, the first antigen-binding domain of (1) is any one of (b1) to (b21) below:

(b1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(b2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(b3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(b4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(b5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(b6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(b7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(b8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(b9) an antibody variable fragment comprising the HVR-H1 sequence identical to the amino acid sequences of the HVR-H1 region comprised in SEQ ID NO: 85, the HVR-H2 sequence identical to the amino acid sequences of the HVR-H2 region comprised in SEQ ID NO: 85, the HVR-H3 sequence identical to the amino acid sequences of the HVR-H3 region comprised in SEQ ID NO: 85, the HVR-L1 sequence identical to the amino acid sequences of the HVR-L1 region comprised in SEQ ID NO: 93, the HVR-L2 sequence identical to the amino acid sequences of the HVR-L2 region comprised in SEQ ID NO: 93, and the HVR-L3 sequence identical to the amino acid sequences of the HVR-L3 region comprised in SEQ ID NO: 93;

(b10) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b11) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b12) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b13) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b15) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(b16) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b17) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b18) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b19) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b20) an antibody variable fragment that binds to the same epitope of any one of the antibody variable fragment selected from (b1) to (b19);

(b21) an antibody variable fragment that competes with the binding of any one of the antibody variable fragment selected from (b1) to (b19).

In some embodiments, in the multispecific antigen-binding molecule, the first antigen-binding domain of (1) comprises any one of the combinations of heavy chain variable region and light chain variable region selected from the following (c1) to (c22):

(c1) heavy chain variable region having the amino acid sequence of SEQ ID NO: 15 and light chain variable region having the amino acid sequence of SEQ ID NO: 16;

(c2) heavy chain variable region having the amino acid sequence of SEQ ID NO: 25 and light chain variable region having the amino acid sequence of SEQ ID NO: 26;

(c3) heavy chain variable region having the amino acid sequence of SEQ ID NO: 19 and light chain variable region having the amino acid sequence of SEQ ID NO: 20;

(c4) heavy chain variable region having the amino acid sequence of SEQ ID NO: 23 and light chain variable region having the amino acid sequence of SEQ ID NO: 24;

(c5) heavy chain variable region having the amino acid sequence of SEQ ID NO: 11 and light chain variable region having the amino acid sequence of SEQ ID NO: 12;

(c6) heavy chain variable region having the amino acid sequence of SEQ ID NO: 13 and light chain variable region having the amino acid sequence of SEQ ID NO: 14;

(c7) heavy chain variable region having the amino acid sequence of SEQ ID NO: 17 and light chain variable region having the amino acid sequence of SEQ ID NO: 18;

(c8) heavy chain variable region having the amino acid sequence of SEQ ID NO: 21 and light chain variable region having the amino acid sequence of SEQ ID NO: 22;

(c9) heavy chain variable region having the amino acid sequence of SEQ ID NO: 85 and light chain variable region having the amino acid sequence of SEQ ID NO: 93;

(c10) heavy chain variable region having the amino acid sequence of SEQ ID NO: 63 and light chain variable region having the amino acid sequence of SEQ ID NO: 72;

(c11) heavy chain variable region having the amino acid sequence of SEQ ID NO: 64 and light chain variable region having the amino acid sequence of SEQ ID NO: 72;

(c12) heavy chain variable region having the amino acid sequence of SEQ ID NO: 65 and light chain variable region having the amino acid sequence of SEQ ID NO: 72;

(c13) heavy chain variable region having the amino acid sequence of SEQ ID NO: 66 and light chain variable region having the amino acid sequence of SEQ ID NO: 73;

(c14) heavy chain variable region having the amino acid sequence of SEQ ID NO: 67 and light chain variable region having the amino acid sequence of SEQ ID NO: 73;

(c15) heavy chain variable region having the amino acid sequence of SEQ ID NO: 67 and light chain variable region having the amino acid sequence of SEQ ID NO: 74;

(c16) heavy chain variable region having the amino acid sequence of SEQ ID NO: 68 and light chain variable region having the amino acid sequence of SEQ ID NO: 72;

(c17) heavy chain variable region having the amino acid sequence of SEQ ID NO: 69 and light chain variable region having the amino acid sequence of SEQ ID NO: 73;

(c18) heavy chain variable region having the amino acid sequence of SEQ ID NO: 70 and light chain variable region having the amino acid sequence of SEQ ID NO: 73;

(c19) heavy chain variable region having the amino acid sequence of SEQ ID NO: 71 and light chain variable region having the amino acid sequence of SEQ ID NO: 73;

(c20) a heavy chain variable region that has an identity more than 80% of any one of the heavy chain variable region of (c1) to (c19), and a light chain variable region that has an identity more than 80% to any one of the light chain variable region of (c1) to (c19);

(c21) a heavy chain variable region that has an identity more than 90% of any one of the heavy chain variable region of (c1) to (c19), and a light chain variable region that has an identity more than 90% to any one of the light chain variable region of (c1) to (c19);

(c22) a heavy chain variable region that has an identity more than 95% of any one of the heavy chain variable region of (c1) to (c19), and a light chain variable region that has an identity more than 95% to any one of the light chain variable region of (c1) to (c19).

In some embodiments, the multispecific antigen-binding molecule has cytotoxic activity. More specifically, the cytotoxic activity is T-cell-dependent cytotoxic activity (T-cell-dependent cellular cytotoxicity (TDCC)).

In some embodiments, in the multispecific antigen-binding molecule, the second antigen-binding domain in (2) binds to CD3. More specifically, in some embodiments, in the multispecific antigen-binding molecule, the second antigen-binding domain in (2) binds to CD3 epsilon chain.

In some embodiments, in the multispecific antigen-binding molecule, the second antigen-binding domain in (2) binds to T-cell receptor.

In some embodiments, in the multispecific antigen-binding molecule, the second antigen-binding domain in (2) is any one of (d1) to (d12) below:

(d1) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 57 respectively, and the HVR-L1, HVR-L2 and HVR-L3 sequences identical to the amino acid sequences of the HVR-L1, HVR-L2 and HVR-L3 regions comprised in SEQ ID NO: 58 respectively;

(d2) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 98 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d3) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 99 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d4) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 100 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d5) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 101 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d6) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 102 respectively, and the HVR-L1, HVR-L2 and HVR-L3 sequences identical to the amino acid sequences of the HVR-L1, HVR-L2 and HVR-L3 regions comprised in SEQ ID NO: 103 respectively;

(d7) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 298 respectively, and the HVR-L1, HVR-L2 and HVR-L3 sequences identical to the amino acid sequences of the HVR-L1, HVR-L2 and HVR-L3 regions comprised in SEQ ID NO: 299 respectively;

(d8) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 300 respectively, and the HVR-L1, HVR-L2 and HVR-L3 sequences identical to the amino acid sequences of the HVR-L1, HVR-L2 and HVR-L3 regions comprised in SEQ ID NO: 301 respectively;

(d9) an antibody variable fragment comprising the HVR-H1, HVR-H2 and HVR-H3 sequences identical to the amino acid sequences of the HVR-H1, HVR-H2 and HVR-H3 regions comprised in SEQ ID NO: 302 respectively, and the HVR-L1, HVR-L2 and HVR-L3 sequences identical to the amino acid sequences of the HVR-L1, HVR-L2 and HVR-L3 regions comprised in SEQ ID NO: 303 respectively;

(d10) an antibody variable fragment comprising the HVR-H1, HVR-H2 and HVR-H3 sequences identical to the amino acid sequences of the HVR-H1, HVR-H2 and HVR-H3 regions comprised in any one selected from SEQ ID NO: 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388 and 390, and the HVR-L1, HVR-L2 and HVR-L3 sequences identical to the amino acid sequences of the HVR-L1, HVR-L2 and HVR-L3 regions comprised in any one selected from SEQ ID NO: 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389 and 391;

(d11) an antibody variable fragment that binds to the same epitope of any one of the antibody variable fragment selected from (d1) to (d10);

(d12) an antibody variable fragment that competes with the binding of any one of the antibody variable fragment selected from (d1) to (d10).

In some embodiments, in the multispecific antigen-binding molecule, the second antigen-binding domain in (2) is any one of (e1) to (e12) below:

(e1) heavy chain variable region having the amino acid sequence of SEQ ID NO: 57 and light chain variable region having the amino acid sequence of SEQ ID NO: 58;

(e2) heavy chain variable region having the amino acid sequence of SEQ ID NO: 98 and light chain variable region having the amino acid sequence of SEQ ID NO: 103;

(e3) heavy chain variable region having the amino acid sequence of SEQ ID NO: 99 and light chain variable region having the amino acid sequence of SEQ ID NO: 103;

(e4) heavy chain variable region having the amino acid sequence of SEQ ID NO: 100 and light chain variable region having the amino acid sequence of SEQ ID NO: 103;

(e5) heavy chain variable region having the amino acid sequence of SEQ ID NO: 101 and light chain variable region having the amino acid sequence of SEQ ID NO: 103;

(e6) heavy chain variable region having the amino acid sequence of SEQ ID NO: 102 and light chain variable region having the amino acid sequence of SEQ ID NO: 103;

(e7) heavy chain variable region having the amino acid sequence of SEQ ID NO: 300 and light chain variable region having the amino acid sequence of SEQ ID NO: 301;

(e8) heavy chain variable region having the amino acid sequence of SEQ ID NO: 302 and light chain variable region having the amino acid sequence of SEQ ID NO: 303;

(e9) heavy chain variable region and light chain variable region having any one of the amino acid sequence combination in Table 2A;

(e10) a heavy chain variable region that has an identity more than 80% of any one of the heavy chain variable region of (e1) to (e9), and a light chain variable region that has an identity more than 80% to any one of the light chain variable region of (e1) to (e9);

(e11) a heavy chain variable region that has an identity more than 90% of any one of the heavy chain variable region of (e1) to (e9), and a light chain variable region that has an identity more than 90% to any one of the light chain variable region of (e1) to (e9);

(e12) a heavy chain variable region that has an identity more than 95% of any one of the heavy chain variable region of (e1) to (e9), and a light chain variable region that has an identity more than 95% to any one of the light chain variable region of (e1) to (e9).

In some embodiments, in the multispecific antigen-binding molecule, the second antigen-binding domain in (2) is any one of (1) to (j5) below:

(1) an antibody variable fragment comprising the HVR-H1 sequence of SEQ ID NO: 136, the HVR-H2 sequence of SEQ ID NO: 137, the HVR-H3 sequence of SEQ ID NO: 138, the HVR-L1 sequence of SEQ ID NO: 139, the HVR-L2 sequence of SEQ ID NO: 140, and the HVR-L3 sequence of SEQ ID NO: 141;

(j2) an antibody variable fragment comprising the HVR-H1 sequence of SEQ ID NO: 142, the HVR-H2 sequence of SEQ ID NO: 143, the HVR-H3 sequence of SEQ ID NO: 144, the HVR-L1 sequence of SEQ ID NO: 145, the HVR-L2 sequence of SEQ ID NO: 146, and the HVR-L3 sequence of SEQ ID NO: 147;

(j3) an antibody variable fragment comprising the HVR sequences selected from any of the combinations in Table 2B;

(j4) an antibody variable fragment that binds to the same epitope of any of the antibody variable fragment selected from (j1) to (j3);

(j5) an antibody variable fragment that competes with the binding of any of the antibody variable fragment selected from (j1) to (j3).

In some embodiments, the multispecific antigen binding molecule further comprises:

(3) a third domain comprising an Fc region with reduced binding activity towards an Fc gamma receptor.

In some embodiments, the present invention provides a multispecific antigen-binding molecule that comprises:

(1) a first domain comprising a first antigen-binding domain binds to human DLL3

(2) a second domain comprising a second antigen-binding domain binds to T-cell receptor complex, and (3) a third domain comprising an Fc region with reduced binding activity towards an Fc gamma receptor.

In some embodiments, in the multispecific antigen-binding molecule, the Fc region of is an Fc region with an amino acid mutation at any of the Fc region-constituting amino acids of SEQ ID NOs: 112 to 115 (IgG1 to IgG4).

In some embodiments, in the multispecific antigen-binding molecule, the Fc region is an Fc region with mutation of at least one amino acid selected from the following amino acid positions specified by EU numbering: position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

In some embodiments, the multispecific antigen-binding molecule is a bispecific antibody.

In some embodiments, the bispecific antibody is a monoclonal antibody.

In preferred embodiments, the above-mentioned multispecific antigen-binding molecule/bispecific antibody/monoclonal antibody has T cell-dependent cellular cytotoxicity (TDCC) activity against cells expressing DLL3.

In another aspect, the present invention provides an antigen-binding molecule that binds to an epitope within the region defined in SEQ ID NO: 7 in human DLL3.

In some embodiments, the antigen-binding molecule comprises an antigen-binding domain comprising any one of (f1) to (f11) below:

(f1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;

(f3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;

(f4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;

(f5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(f7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;

(f8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38;

(f9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81;

(f10) an antibody variable fragment that binds to the same epitope of any of the antibody variable fragment selected from (f1) to (f9);

(f11) an antibody variable fragment that competes with the binding of any of the antibody variable fragment selected from (f1) to (f9).

In some embodiments, the antigen-binding molecule comprises an antigen-binding domain comprising any one of (g1) to (g20) below:

(g1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(g2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(g3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(g4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(g5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(g6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(g7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(g8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(g9) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g10) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g11) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(g12) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g13) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(g15) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g16) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g17) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g18) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(g19) an antibody variable fragment that binds to the same epitope of any one of the antibody variable fragment selected from (g1) to (g18);

(g20) an antibody variable fragment that competes with the binding of any one of the antibody variable fragment selected from (g1) to (g18).

In some embodiments, the antigen-binding molecule comprises an antigen-binding domain comprising any one of (h1) to (h21) below:

(h1) heavy chain variable region having the amino acid sequence of SEQ ID NO: 15 and light chain variable region having the amino acid sequence of SEQ ID NO: 16;

(h2) heavy chain variable region having the amino acid sequence of SEQ ID NO: 25 and light chain variable region having the amino acid sequence of SEQ ID NO: 26;

(h3) heavy chain variable region having the amino acid sequence of SEQ ID NO: 19 and light chain variable region having the amino acid sequence of SEQ ID NO: 20;

(h4) heavy chain variable region having the amino acid sequence of SEQ ID NO: 23 and light chain variable region having the amino acid sequence of SEQ ID NO: 24;

(h5) heavy chain variable region having the amino acid sequence of SEQ ID NO: 11 and light chain variable region having the amino acid sequence of SEQ ID NO: 12;

(h6) heavy chain variable region having the amino acid sequence of SEQ ID NO: 13 and light chain variable region having the amino acid sequence of SEQ ID NO: 14;

(h7) heavy chain variable region having the amino acid sequence of SEQ ID NO: 17 and light chain variable region having the amino acid sequence of SEQ ID NO: 18;

(h8) heavy chain variable region having the amino acid sequence of SEQ ID NO: 21 and light chain variable region having the amino acid sequence of SEQ ID NO: 22;

(h9) heavy chain variable region having the amino acid sequence of SEQ ID NO: 63 and light chain variable region having the amino acid sequence of SEQ ID NO: 72;

(h10) heavy chain variable region having the amino acid sequence of SEQ ID NO: 64 and light chain variable region having the amino acid sequence of SEQ ID NO: 72;

(h11) heavy chain variable region having the amino acid sequence of SEQ ID NO: 65 and light chain variable region having the amino acid sequence of SEQ ID NO: 72;

(h12) heavy chain variable region having the amino acid sequence of SEQ ID NO: 66 and light chain variable region having the amino acid sequence of SEQ ID NO: 73;

(h13) heavy chain variable region having the amino acid sequence of SEQ ID NO: 67 and light chain variable region having the amino acid sequence of SEQ ID NO: 73;

(h14) heavy chain variable region having the amino acid sequence of SEQ ID NO: 67 and light chain variable region having the amino acid sequence of SEQ ID NO: 74;

(h15) heavy chain variable region having the amino acid sequence of SEQ ID NO: 68 and light chain variable region having the amino acid sequence of SEQ ID NO: 72;

(h16) heavy chain variable region having the amino acid sequence of SEQ ID NO: 69 and light chain variable region having the amino acid sequence of SEQ ID NO: 73;

(h17) heavy chain variable region having the amino acid sequence of SEQ ID NO: 70 and light chain variable region having the amino acid sequence of SEQ ID NO: 73;

(h18) heavy chain variable region having the amino acid sequence of SEQ ID NO: 71 and light chain variable region having the amino acid sequence of SEQ ID NO: 73;

(h19) a heavy chain variable region that has an identity more than 80% of any one of the heavy chain variable region of (h1) to (h18); and a light chain variable region that has an identity more than 80% to any one of the light chain variable region of (h1) to (h18);

(h20) a heavy chain variable region that has an identity more than 90% of any one of the heavy chain variable region of (h1) to (h18); and a light chain variable region that has an identity more than 90% to any one of the light chain variable region of (h1) to (h18);

(h21) a heavy chain variable region that has an identity more than 95% of any one of the heavy chain variable region of (h1) to (h18); and a light chain variable region that has an identity more than 95% to any one of the light chain variable region of (h1) to (h18).

In some embodiments, the antigen-binding molecule has cellular cytotoxic activity.

In some embodiments, in the antigen-binding molecule, the cytotoxic activity is antibody dependent cellular cytotoxicity or complement dependent cytotoxicity.

In some embodiments, the antigen-binding molecule has internalization activity.

In some embodiments, the antigen-binding molecule is conjugated to a toxic compound.

In some embodiments, the antigen-binding molecule is an antibody.

In some embodiments, the antigen-binding molecule is a monoclonal antibody.

In some embodiments, the present invention provides an antibody-drug-conjugate compound that comprises the antibody.

Class of Antibody

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively. In preferred embodiments, the antibody of the present invention is an IgG-type antibody.

Framework

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

Human Consensus Framework

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

HVR

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

Variable Region

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

Chimeric Antibody

The term "chimeric" antibody refers to an antibody in which a portion of the heavy and/or light chain is derived from a particular source or species, while the remainder of the heavy and/or light chain is derived from a different source or species. Similarly, the term "chimeric antibody variable domain" refers to an antibody variable region in which a portion of the heavy and/or light chain variable region is derived from a particular source or species, while the remainder of the heavy and/or light chain variable region is derived from a different source or species.

Humanized Antibody

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. A "humanized antibody variable region" refers to the variable region of a humanized antibody.

Human Antibody

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. A "human antibody variable region" refers to the variable region of a human antibody.

Methods for Producing an Antibody with Desired Binding Activity

Methods for producing an antibody with desired binding activity are known to those skilled in the art. Below is an example that describes a method for producing an antibody (anti-DLL3 antibody) that binds to DLL3 mentioned above. Antibodies that bind to a T-cell receptor complex and so on can also be produced as described below.

Anti-DLL3 antibodies can be obtained as polyclonal or monoclonal antibodies using known methods. The anti-DLL3 antibodies preferably produced are monoclonal antibodies derived from mammals. Such mammal-derived monoclonal antibodies include antibodies produced by hybridomas or host cells transformed with an expression vector carrying an antibody gene by genetic engineering techniques.

Monoclonal antibody-producing hybridomas can be produced using known techniques, for example, as described below. Specifically, mammals are immunized by conventional immunization methods using a DLL3 protein as a sensitizing antigen. Resulting immune cells are fused with known parental cells by conventional cell fusion methods. Then, hybridomas producing an anti-DLL3 antibody can be selected by screening for monoclonal antibody-producing cells using conventional screening methods.

Specifically, monoclonal antibodies are prepared as mentioned below. First, the DLL3 gene whose nucleotide sequence is disclosed in NCBI Reference Sequence NM_016941.3 or XP_005589253.1 can be expressed to produce the DLL3 protein which will be used as a sensitizing antigen for antibody preparation. Alternatively, a polynucleotide encoding the extracellular domain (ECD) of DLL3 can be expressed to produce an DLL3 ECD-containing protein. That is, a gene sequence encoding full-length DLL3 or DLL3 ECD is inserted into a known expression vector, and appropriate host cells are transformed with this vector. The desired full-length DLL3 or DLL3 ECD protein is purified from the host cells or their culture supernatants by known methods. Alternatively, it is possible to use a purified natural DLL3 protein as a sensitizing antigen.

The purified full-length DLL3 or DLL3 ECD protein can be used as a sensitizing antigen for use in immunization of mammals. Partial peptides of full-length DLL3 or DLL3

ECD can also be used as sensitizing antigens. In this case, the partial peptides may also be obtained by chemical synthesis from the DLL3 amino acid sequence. Furthermore, they may also be obtained by incorporating a portion of the DLL3 gene into an expression vector and expressing it. Moreover, they may also be obtained by degrading the DLL3 protein using proteases, but the region and size of the DLL3 peptide used as the partial peptide are not particularly limited to a special embodiment. As the preferred region, any sequence from the amino acid sequence may be selected. The number of amino acids constituting a peptide to be used as the sensitizing antigen is at least five or more, or preferably for example, six or more, or seven or more. More specifically, peptides consisting of 8 to 50 residues or preferably 10 to 30 residues may be used as the sensitizing antigen.

For sensitizing antigen, alternatively it is possible to use a fusion protein prepared by fusing a desired partial polypeptide or peptide of the full-length DLL3 or DLL3 ECD protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing DLL3 to be used as a sensitizing antigen, and immunization methods using DLL3 are also described in the Examples of this specification later.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as DLL3; and there is no need to purify the antigen for immunization.

In order to prepare a monoclonal antibody of the present invention using DNA immunization, first, a DNA expressing a DLL3 protein is administered to an animal to be immunized. The DLL3-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized DLL3 can also be produced by the methods described in WO 2011/093097.

After immunizing a mammal as described above, an increase in the titer of a DLL3-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immunocyte. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978)81, 1-7);

NS-1 (C. Eur. J. Immunol. (1976)6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37 degrees C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, a DLL3-binding monoclonal antibody can bind to DLL3 expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, DLL3-expressing cells are first prepared. Cells preferably used for screening are mammalian cells in which DLL3 is forcedly expressed. As control, the activity of an antibody to bind to cell-surface DLL3 can be selectively detected using non-transformed mammalian cells as host cells. Specifically, hybridomas producing an anti-DLL3 monoclonal antibody can be isolated by selecting hybridomas that produce an antibody which binds to cells forced to express DLL3, but not to host cells.

Alternatively, the activity of an antibody to bind to immobilized DLL3-expressing cells can be assessed based on the principle of ELISA. For example, DLL3-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

Preferably, the present invention provides nucleic acids that encode a multispecific antigen-binding molecule or a monospecific antigen-binding molecule of the present invention. The present invention also provides a vector into which the nucleic acid encoding the multispecific antigen-binding molecule or the monospecific antigen-binding molecule is introduced, i.e., a vector comprising the nucleic acid. Furthermore, the present invention provides a cell comprising the nucleic acid or the vector. The present invention also provides a method for producing the multispecific antigen-binding molecule or the monospecific antigen-binding molecule by culturing the cell. The present invention further provides multispecific antigen-binding molecules or monospecific antigen-binding molecules produced by the method.

For example, a cDNA encoding the variable region (V region) of an anti-DLL3 antibody is prepared from hybridoma cells expressing the anti-DLL3 antibody. For this purpose, total RNA is first extracted from hybridomas. Methods used for extracting mRNAs from cells include, for example:

- the guanidine ultracentrifugation method (Biochemistry (1979) 18(24), 5294-5299), and
- the AGPC method (Anal. Biochem. (1987) 162(1), 156-159).

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into *E. coli* or such. After colony selection, the desired recombinant vector can be prepared from the colony-forming *E. coli*. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding gamma1, gamma2a, gamma2b, and gamma3 heavy chains and kappa and lambda light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the DLL3-binding activity of a reshaped immunoglobulin as an indicator. For example, when the objective is to isolate an antibody against DLL3, it is more preferred that the binding of the antibody to DLL3 is specific. A DLL3-binding antibody can be screened, for example, by the following steps:

(1) contacting a DLL3-expressing cell with an antibody comprising the V region encoded by a cDNA isolated from a hybridoma;
(2) detecting the binding of the antibody to the DLL3-expressing cell; and
(3) selecting an antibody that binds to the DLL3-expressing cell.

Methods for detecting the binding of an antibody to DLL3-expressing cells are known. Specifically, the binding of an antibody to DLL3-expressing cells can be detected by the above-described techniques such as FACS. Immobilized samples of DLL3-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having a desired binding activity.

After isolation of the cDNA encoding the V region of the anti-DLL3 antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-DLL3 antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-DLL3 monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-DLL3 antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 94/11523).

There are various known host cell/expression vector combinations for antibody preparation by introducing isolated antibody genes into appropriate hosts. All of these expression systems are applicable to isolation of domains including antibody variable regions of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, or such;

(2) amphibian cells: *Xenopus* oocytes, or such; and (3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat beta casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

Methods for Producing a Humanized Antibody

When an antigen-binding molecule described herein is administered to human, a domain derived from a genetically recombinant antibody that has been artificially modified to reduce the heterologous antigenicity against human and such, can be appropriately used as the domain of the antigen-binding molecule including an antibody variable region. Such genetically recombinant antibodies include, for example, humanized antibodies. These modified antibodies are appropriately produced by known methods. Furthermore, generally, the binding specificity of a certain antibody can be introduced into another antibody by CDR grafting.

Specifically, humanized antibodies prepared by grafting the CDR (or "HVR" as defined herein) of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856)

Methods for Producing a Human Antibody

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing a scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

Vector

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Host Cell

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Epitope

"Epitope" means an antigenic determinant in an antigen, and refers to an antigen site to which the antigen-binding domain of an antigen-binding molecule or antibody disclosed herein binds. Thus, for example, the epitope can be defined according to its structure. Alternatively, the epitope may be defined according to the antigen-binding activity of an antigen-binding molecule or antibody that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antigen-binding domain recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antigen-binding domain. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Examples of a method for assessing the epitope binding by a test antigen-binding molecule or antibody containing an anti-DLL3 antigen-binding domain are described below. According to the examples below, methods for assessing the epitope binding by a test antigen-binding molecule or antibody containing an antigen-binding domain for an antigen other than DLL3, can also be appropriately conducted.

For example, whether a test antigen-binding molecule or antibody containing an anti-DLL3 antigen-binding domain recognizes a linear epitope in the DLL3 molecule can be confirmed for example as mentioned below. A linear peptide comprising an amino acid sequence forming the extracellular domain of DLL3 is synthesized for the above purpose. The peptide can be synthesized chemically, or obtained by genetic engineering techniques using a region encoding the amino acid sequence corresponding to the extracellular domain in a DLL3 cDNA. Then, a test antigen-binding molecule or antibody containing an anti-DLL3 antigen-binding domain is assessed for its binding activity towards a linear peptide comprising the amino acid sequence forming the extracellular domain. For example, an immobilized linear peptide can be used as an antigen by ELISA to evaluate the binding activity of the polypeptide complex towards the peptide. Alternatively, the binding activity towards a linear peptide can be assessed based on the level that the linear peptide inhibits the binding of the antigen-binding molecule or antibody to DLL3-expressing cells. These tests can demonstrate the binding activity of the antigen-binding molecule or antibody towards the linear peptide.

Whether a test antigen-binding molecule or antibody containing an anti-DLL3 antigen-binding domain recognizes a conformational epitope can be assessed as follows. DLL3-expressing cells are prepared for the above purpose. A test antigen-binding molecule or antibody containing an anti-DLL3 antigen-binding domain can be determined to recognize a conformational epitope when it strongly binds to DLL3-expressing cells upon contact, but does not substantially bind to an immobilized linear peptide comprising an amino acid sequence forming the extracellular domain of DLL3. Herein, "not substantially bind" means that the binding activity is 80% or less, generally 50% or less, preferably 30% or less, and particularly preferably 15% or less compared to the binding activity towards cells expressing DLL3.

Methods for assaying the binding activity of a test antigen-binding molecule or antibody containing an anti-DLL3 antigen-binding domain towards DLL3-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using DLL3-expressing cells as antigen.

In the ELISA format, the binding activity of a test antigen-binding molecule or antibody containing an anti-DLL3 antigen-binding domain towards DLL3-expressing cells can be assessed quantitatively by comparing the levels of signal generated by enzymatic reaction. Specifically, a test polypeptide complex is added to an ELISA plate onto which DLL3-expressing cells are immobilized. Then, the test antigen-binding molecule or antibody bound to the cells is detected using an enzyme-labeled antibody that recognizes the test antigen-binding molecule or antibody. Alternatively, when FACS is used, a dilution series of a test antigen-binding molecule or antibody is prepared, and the antibody binding titer for DLL3-expressing cells can be determined to compare the binding activity of the test antigen-binding molecule or antibody towards DLL3-expressing cells.

The binding of a test antigen-binding molecule or antibody towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter)

Preferable methods for assaying the binding activity of a test antigen-binding molecule or antibody containing an anti-DLL3 antigen-binding domain towards an antigen include, for example, the following method. First, DLL3-expressing cells are reacted with a test antigen-binding molecule or antibody, and then this is stained with an FITC-labeled secondary antibody that recognizes the antigen-binding molecule or antibody. The test antigen-binding molecule or antibody is appropriately diluted with a suitable buffer to prepare the antigen-binding molecule or antibody at a desired concentration. For example, the antigen-binding molecule or antibody can be used at a concentration within the range of 10 micro g/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule or antibody, which is represented by the quantity of the test antigen-binding molecule or antibody bound, can be determined by measuring the Geometric Mean value.

Whether a test antigen-binding molecule or antibody containing an anti-DLL3 antigen-binding domain shares a common epitope with another antigen-binding molecule or antibody can be assessed based on the competition between the two antigen-binding molecules or antibodies for the same epitope. The competition between the antigen-binding molecules or antibodies can be detected by cross-blocking assay or the like. For example, the competitive ELISA assay is a preferred cross-blocking assay.

Specifically, in cross-blocking assay, the DLL3 protein immobilized to the wells of a microtiter plate is pre-incubated in the presence or absence of a candidate competitor antigen-binding molecule or antibody, and then a test antigen-binding molecule or antibody is added thereto. The quantity of test antigen-binding molecule or antibody bound to the DLL3 protein in the wells is indirectly correlated with the binding ability of a candidate competitor antigen-binding molecule or antibody that competes for the binding to the same epitope. That is, the greater the affinity of the competitor antigen-binding molecule or antibody for the same epitope, the lower the binding activity of the test antigen-binding molecule or antibody towards the DLL3 protein-coated wells.

The quantity of the test antigen-binding molecule or antibody bound to the wells via the DLL3 protein can be readily determined by labeling the antigen-binding molecule or antibody in advance. For example, a biotin-labeled antigen-binding molecule or antibody is measured using an avidin/peroxidase conjugate and appropriate substrate. In particular, cross-blocking assay that uses enzyme labels such as peroxidase is called "competitive ELISA assay". The antigen-binding molecule or antibody can also be labeled with other labeling substances that enable detection or measurement. Specifically, radiolabels, fluorescent labels, and such are known.

When the candidate competitor antigen-binding molecule or antibody can block the binding by a test antigen-binding molecule or antibody containing an anti-DLL3 antigen-binding domain by at least 20%, preferably at least 20 to 50%, and more preferably at least 50% compared to the binding activity in a control experiment conducted in the absence of the competitor antigen-binding molecule or antibody, the test antigen-binding molecule or antibody is determined to substantially bind to the same epitope bound by the competitor antigen-binding molecule or antibody, or compete for the binding to the same epitope.

When the structure of an epitope bound by a test antigen-binding molecule or antibody containing an anti-DLL3 antigen-binding domain has already been identified, whether the test and control antigen-binding molecules or antibodies share a common epitope can be assessed by comparing the binding activities of the two antigen-binding molecules or antibodies towards a peptide prepared by introducing amino acid mutations into the peptide forming the epitope.

To measure the above binding activities, for example, the binding activities of test and control antigen-binding molecules or antibodies towards a linear peptide into which a mutation is introduced are compared in the above ELISA format. Besides the ELISA methods, the binding activity towards the mutant peptide bound to a column can be determined by flowing test and control antigen-binding molecules or antibodies in the column, and then quantifying the antigen-binding molecule or antibody eluted in the elution solution. Methods for adsorbing a mutant peptide to a column, for example, in the form of a GST fusion peptide, are known.

Alternatively, when the identified epitope is a conformational epitope, whether test and control antigen-binding molecules or antibodies share a common epitope can be assessed by the following method. First, DLL3-expressing cells and cells expressing DLL3 with a mutation introduced into the epitope are prepared. The test and control antigen-binding molecules or antibodies are added to a cell suspension prepared by suspending these cells in an appropriate buffer such as PBS. Then, the cell suspensions are appropriately washed with a buffer, and an FITC-labeled antibody that recognizes the test and control antigen-binding molecules or antibodies is added thereto. The fluorescence intensity and number of cells stained with the labeled antibody are determined using FACSCalibur (BD). The test and control antigen-binding molecules or antibodies are appropriately diluted using a suitable buffer, and used at desired concentrations. For example, they may be used at a concentration within the range of 10 micro g/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules or antibodies, which are represented by the quantity of labeled antibody bound, can be determined by measuring the Geometric Mean value.

In the above method, whether an antigen-binding molecule or antibody does "not substantially bind to cells expressing mutant DLL3 (or a DLL3 variant)" can be assessed, for example, by the following method. First, the test and control antigen-binding molecules or antibodies bound to cells expressing mutant DLL3 are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the antigen-binding molecule or antibody, the comparison value (delta Geo-Mean) can be calculated according to the following formula to determine the ratio of increase in fluorescence intensity as a result of the binding by the antigen-binding molecule or antibody.

delta Geo-Mean=Geo-Mean(in the presence of the antigen-binding molecule or antibody)/Geo-Mean(in the absence of the antigen-binding molecule or antibody)

The Geometric Mean comparison value (delta Geo-Mean value for the mutant DLL3 molecule) determined by the above analysis, which reflects the quantity of a test antigen-binding molecule or antibody bound to cells expressing mutant DLL3, is compared to the delta Geo-Mean comparison value that reflects the quantity of the test antigen-binding molecule or antibody bound to DLL3-expressing cells. In this case, the concentrations of the test antigen-binding molecule or antibody used to determine the delta Geo-Mean comparison values for DLL3-expressing cells and cells expressing mutant DLL3 are particularly preferably adjusted to be equal or substantially equal. An antigen-binding molecule or antibody that has been confirmed to recognize an epitope in DLL3 is used as a control antigen-binding molecule or antibody.

If the delta Geo-Mean comparison value of a test antigen-binding molecule or antibody for cells expressing mutant DLL3 is smaller than the delta Geo-Mean comparison value of the test antigen-binding molecule or antibody for DLL3-expressing cells by at least 80%, preferably 50%, more preferably 30%, and particularly preferably 15%, then the test antigen-binding molecule or antibody "does not substantially bind to cells expressing mutant DLL3 (or a DLL3 variant)". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules or antibodies can be determined to be the same.

Antibody that Binds to the Same Epitope

An antigen-binding molecule or an antibody comprising an antigen-binding domain that "binds to the same epitope" as a reference antibody refers to an antigen-binding molecule or an antibody that blocks binding of the reference antibody to its antigen in a competition assay by 50% or more, and conversely, the reference antibody blocks binding of the antigen-binding molecule or the antibody to its antigen in a competition assay by 50% or more. An exemplary competition assay such as cross-blocking assay is provided above.

Specificity

"Specific" means that a molecule that binds specifically to one or more binding partners does not show any significant binding to molecules other than the partners. Furthermore, "specific" is also used when an antigen-binding domain is specific to a particular epitope of multiple epitopes contained in an antigen. When an epitope bound by an antigen-binding domain is contained in multiple different antigens, an antigen-binding molecule containing the antigen-binding domain can bind to various antigens that have the epitope.

Antibody Fragment

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and monospecific or multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

Variable Fragment (Fv)

Herein, the term "variable fragment (Fv)" refers to the minimum unit of an antibody-derived antigen-binding domain that is composed of a pair of the antibody light chain variable region (VL) and antibody heavy chain variable region (VH). In 1988, Skerra and Pluckthun found that homogeneous and active antibodies can be prepared from the *E. coli* periplasm fraction by inserting an antibody gene downstream of a bacterial signal sequence and inducing expression of the gene in *E. coli* (Science (1988) 240(4855), 1038-1041). In the Fv prepared from the periplasm fraction, VH associates with VL in a manner so as to bind to an antigen. Herein, the term "antibody variable fragment" refers to any fragment that comprises at least one antibody light chain variable region (VL) and at least one antibody heavy chain variable region (VH).

scFv, Single-Chain Antibody, and Sc(Fv)2

Herein, the terms "scFv", "single-chain antibody", and "sc(Fv)2" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)2 is a single-chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)2 preferably includes, for example, a bispecific sc(Fv)2 that recognizes two epitopes present in a single antigen as disclosed in the Journal of Immunology (1994) 152(11), 5368-5374. sc(Fv)2 can be produced by methods known to those skilled in the art. For example, sc(Fv)2 can be produced by linking scFv by a linker such as a peptide linker.

Herein, the form of an antigen-binding domain forming an sc(Fv)2 include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Examples of the form are listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)2 is also described in detail in WO 2006/132352. According to these descriptions, those skilled in the art can appropriately prepare desired sc(Fv)2 to produce the polypeptide complexes disclosed herein.

Furthermore, the antigen-binding molecules or antibodies of the present invention may be conjugated with a carrier polymer such as PEG or an organic compound such as an anticancer agent. Alternatively, a sugar chain addition sequence is preferably inserted into the antigen-binding molecules or antibodies such that the sugar chain produces a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)2 contains three peptide linkers, their length may be all the same or different.

For example, such peptide linkers include:

```
Ser

Gly Ser

Gly Gly Ser

Ser Gly Gly

                                    (SEQ ID NO: 116)
Gly Gly Gly Ser

                                    (SEQ ID NO: 117)
Ser Gly Gly Gly

                                    (SEQ ID NO: 118)
Gly Gly Gly Gly Ser

                                    (SEQ ID NO: 119)
Ser Gly Gly Gly Gly

                                    (SEQ ID NO: 120)
Gly Gly Gly Gly Gly Ser
```

-continued

```
                                    (SEQ ID NO: 121)
Ser Gly Gly Gly Gly Gly

                                    (SEQ ID NO: 122)
Gly Gly Gly Gly Gly Gly Ser

                                    (SEQ ID NO: 123)
Ser Gly Gly Gly Gly Gly Gly

(Gly Gly Gly Gly Ser (SEQ ID NO: 118))n

(Ser Gly Gly Gly Gly (SEQ ID NO: 119))n
```

where n is an integer of 1 or larger. The length or sequences of peptide linkers can be selected accordingly by those skilled in the art depending on the purpose.

Synthetic linkers (chemical crosslinking agents) are routinely used to crosslink peptides, and examples include:

N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES), and
bis[2-(sulfosuccinimidoxycarbonyloxy)ethyl] sulfone (sulfo-BSOCOES). These crosslinking agents are commercially available.

In general, three linkers are required to link four antibody variable regions together. The linkers to be used may be of the same type or different types.

Fab, F(ab')2, and Fab'

"Fab" consists of a single light chain, and a CH1 domain and variable region from a single heavy chain. The heavy chain of Fab molecule cannot form disulfide bonds with another heavy chain molecule.

"F(ab')2" or "Fab" is produced by treating an immunoglobulin (monoclonal antibody) with a protease such as pepsin and papain, and refers to an antibody fragment generated by digesting an immunoglobulin (monoclonal antibody) near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CH gamma 1 (gamma 1 region in an H-chain constant region) via a disulfide bond at their C-terminal regions. Each of these two homologous antibody fragments is called Fab'.

"F(ab')2" consists of two light chains and two heavy chains comprising the constant region of a CH1 domain and a portion of CH2 domains so that disulfide bonds are formed between the two heavy chains. The F(ab')2 disclosed herein can be preferably produced as follows. A whole monoclonal antibody or such comprising a desired antigen-binding domain is partially digested with a protease such as pepsin; and Fc fragments are removed by adsorption onto a Protein A column. The protease is not particularly limited, as long as it can cleave the whole antibody in a selective manner to produce F(ab')2 under an appropriate setup enzyme reaction condition such as pH. Such proteases include, for example, pepsin and ficin.

Fc Region

The term "Fc region" or "Fc domain" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991.

Native Sequence Fc Region

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

Variant Fc Region

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

Fc Receptor

The term "Fc receptor" or "FcR" refers to a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and plasma half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with increased or decreased binding to FcRs. See also, e.g., Shields et al. J. Biol. Chem. 9(2):6591-6604 (2001).

Fc Gamma Receptor

Fc gamma receptor refers to a receptor capable of binding to the Fc domain of monoclonal IgG1, IgG2, IgG3, or IgG4 antibodies, and includes all members belonging to the family of proteins substantially encoded by an Fc gamma receptor gene. In human, the family includes Fc gamma RI (CD64) including isoforms Fc gamma RIa, Fc gamma RIb and Fc gamma RIc; Fc gamma RII (CD32) including isoforms Fc gamma RIIa (including allotype H131 and R131), Fc gamma RIIb (including Fc gamma RIIb-1 and Fc gamma RIIb-2), and Fc gamma RIIc; and Fe gamma RIII (CD16) including isoform Fc gamma RIIIa (including allotype V158 and F158) and Fc gamma RIIIb (including allotype Fc gamma RIIIb-NA1 and Fe gamma RIIIb-NA2); as well as all unidentified human Fc gamma receptors, Fe gamma receptor isoforms, and allotypes thereof. However, Fc gamma receptor is not limited to these examples. Without being limited thereto, Fc gamma receptor includes those derived from humans, mice, rats, rabbits, and monkeys. Fc gamma receptor may be derived from any organisms. Mouse Fc gamma receptor includes, without being limited to, Fc gamma RI (CD64), Fc gamma RII (CD32), Fc gamma RIII (CD16), and Fc gamma RIII-2 (CD16-2), as well as all unidentified mouse Fe gamma receptors, Fc gamma receptor isoforms, and allotypes thereof. Such preferred Fc gamma receptors include, for example, human Fc gamma RI (CD64), Fc gamma RIIA (CD32), Fc gamma RIIB (CD32), Fc gamma RIIIA (CD16), and/or Fc gamma RIIIB (CD16). The polynucleotide sequence and amino acid sequence of Fc gamma RI are shown in NCBI Reference Sequence NM_000566.3 (SEQ ID NO: 124) and NP_000557.1 (SEQ ID NO: 125), respectively; the polynucleotide sequence and amino acid sequence of Fc gamma RIIA are shown in BC020823.1 (SEQ ID NO: 126) and AAH20823.1 (SEQ ID NO: 127), respectively; the polynucleotide sequence and amino acid sequence of Fc gamma RIIB are shown in BC146678.1 (SEQ ID NO: 128) and AAI46679.1 (SEQ ID NO: 129), respectively; the polynucleotide sequence and amino acid sequence of Fe gamma RIIIA are shown in BC033678.1 (SEQ ID NO: 130) and AAH33678.1 (SEQ ID NO: 131), respectively; and the polynucleotide sequence and amino acid sequence of Fc gamma RIIIB are shown in BC128562.1 (SEQ ID NO: 132) and AAI28563.1 (SEQ ID NO: 133), respectively (RefSeq accession numbers). Whether an Fc gamma receptor has binding activity to the Fc domain of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, Fc gamma receptor, Fc alpha receptor, Fc beta receptor, FcRn, C1q, and C3, mannan-binding lectin, mannose receptor, *Staphylococcus* Protein A, *Staphylococcus* Protein G, and viral Fc gamma receptors. The Fc ligands also include Fc receptor homologs (FcRH) (Davis et al., (2002) Immunological Reviews 190, 123-136), which are a family of Fc receptors homologous to Fc gamma receptor. The Fc ligands also include unidentified molecules that bind to Fc.

Fc Gamma Receptor-Binding Activity

The impaired binding activity of Fc domain to any of the Fc gamma receptors Fc gamma RI, Fc gamma RIIA, Fc gamma RIIB, Fc gamma RIIIA, and/or Fe gamma RIIIB can be assessed by using the above-described FACS and ELISA formats as well as ALPHA screen (Amplified Luminescent Proximity Homogeneous Assay) and surface plasmon resonance (SPR)-based BIACORE method (Proc. Natl. Acad. Sci. USA (2006) 103(11), 4005-4010). In some embodiments, an antigen-binding molecule or antibody of the present invention comprises a domain comprising an Fc region with reduced binding activity towards an Fc gamma receptor.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule or antibody is immobilized to the donor beads and glutathione S-transferase (GST)-tagged Fc gamma receptor is immobilized to the acceptor beads. In the absence of an antigen-binding molecule or antibody comprising a competitive mutant Fc domain, Fc gamma receptor interacts with an antigen-binding molecule or antibody comprising a wild-type Fc domain, inducing a signal of 520 to 620 nm as a result. The antigen-binding molecule or antibody having a non-tagged mutant Fc domain competes with the antigen-binding molecule or antibody comprising a wild-type Fc domain for the interaction with Fc gamma receptor. The relative binding affinity can be determined by quantifying the reduction of fluorescence as a result of competition. Methods for biotinylating the antigen-binding molecules or antibodies such as antibodies using Sulfo-NHS-biotin or the like are known. Appropriate methods for adding the GST tag to an Fc gamma receptor include methods that involve fusing polypeptides encoding Fc gamma receptor and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE methods. Examples of such inhibition assay are described in Proc. Natl. Acad. Sci. USA (2006) 103(11), 4005-4010.

Functional Fc Region

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein. In some embodiments, an antigen-binding molecule or antibody of the present invention comprises a domain comprising a functional Fc region with effector functions.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Human Effector Cells

"Human effector cells" refer to leukocytes that express one or more FcRs and perform effector functions. In certain embodiments, the cells express at least Fc gamma RIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

Fc Region with a Reduced Fc Gamma Receptor-Binding Activity

Herein, "a reduced Fc gamma receptor-binding activity" means, for example, that based on the above-described analysis method the competitive activity of a test antigen-binding molecule or antibody is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control antigen-binding molecule or antibody.

Antigen-binding molecules or antibodies comprising the Fc domain of a monoclonal IgG1, IgG2, IgG3, or IgG4 antibody can be appropriately used as control antigen-binding molecules or antibodies. The Fc domain structures are shown in SEQ ID NOs: 112 (A is added to the N terminus of RefSeq accession number AAC82527.1), 113 (A is added to the N terminus of RefSeq accession number AAB59393.1), 114 (A is added to the N terminus of RefSeq accession number CAA27268.1), and 115 (A is added to the N terminus of RefSeq accession number AAB59394.1). Furthermore, when an antigen-binding molecule or antibody comprising an Fc domain mutant of an antibody of a particular isotype is used as a test substance, the effect of the mutation of the mutant on the Fc gamma receptor-binding activity is assessed using as a control an antigen-binding molecule or antibody comprising an Fc domain of the same isotype. As described above, antigen-binding molecules or antibodies comprising an Fc domain mutant whose Fc gamma receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1(1), 47-54); C226S, C229S, E233P, L234V, and L235A (Blood (2007) 109, 1185-1192).

Specifically, the preferred antigen-binding molecules or antibodies include those comprising an Fc domain with a mutation (such as substitution) of at least one amino acid selected from the following amino acid positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering), in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

The preferred antigen-binding molecules or antibodies include, for example, those comprising an Fc domain which has any one of the substitutions shown below, whose positions are specified according to EU numbering (each number represents the position of an amino acid residue in the EU numbering; and the one-letter amino acid symbol before the number represents the amino acid residue before substitution, while the one-letter amino acid symbol after the number represents the amino acid residue after the substitution) in the amino acids forming the Fc domain of IgG1 antibody:

(a) L234F, L235E, P331S;
(b) C226S, C229S, P238S;
(c) C226S, C229S; or
(d) C226S, C229S, E233P, L234V, L235A;

as well as those having an Fc domain which has a deletion of the amino acid sequence at positions 231 to 238.

Furthermore, the preferred antigen-binding molecules or antibodies also include those comprising an Fc domain that has any one of the substitutions shown below, whose positions are specified according to EU numbering in the amino acids forming the Fc domain of an IgG2 antibody:

(e) H268Q, V309L, A330S, and P331S;
(f) V234A;
(g) G237A;
(h) V234A and G237A;
(i) A235E and G237A; or
(j) V234A, A235E, and G237A.

Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG3 antibody:

(k) F241A;
(l) D265A; or
(m) V264A.

Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG4 antibody:

(n) L235A, G237A, and E318A;
(o) L235E; or
(p) F234A and L235A.

Each number represents the position of an amino acid residue in EU numbering; and the one-letter amino acid symbol before the number represents the amino acid residue before substitution, while the one-letter amino acid symbol after the number represents the amino acid residue after the substitution.

The other preferred antigen-binding molecules or antibodies include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

The preferred antigen-binding molecules or antibodies also include, for example, those comprising an Fc domain in which any one or more of the amino acids at positions 234, 235, and 297 (EU numbering) in the amino acids forming the Fc domain of an IgG1 antibody is substituted with other amino acids. The type of amino acid after substitution is not particularly limited; however, the antigen-binding molecules or antibodies comprising an Fc domain in which any one or more of the amino acids at positions 234, 235, and 297 are substituted with alanine are particularly preferred.

The preferred antigen-binding molecules or antibodies also include, for example, those comprising an Fc domain in which an amino acid at position 265 (EU numbering) in the amino acids forming the Fc domain of an IgG1 antibody is substituted with another amino acid. The type of amino acid after substitution is not particularly limited; however, antigen-binding molecules or antibodies comprising an Fc domain in which an amino acid at position 265 is substituted with alanine are particularly preferred.

Antigen-Binding Domains Binds to DLL3

The phrase "an antigen-binding domain binds to DLL3" or "an anti-DLL3 antigen-binding domain" as used herein refers to an antigen-binding domain that specifically binds to the above-mentioned DLL3 protein, or the whole or a portion of a partial peptide of the DLL3 protein.

In certain embodiments, the antigen-binding domain binds to DLL3 is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to DLL3 is a domain comprising an antibody variable fragment. Domains comprising an antibody variable fragment may be provided from variable domains of one or a plurality of antibodies.

In certain embodiments, the antigen-binding domain binds to DLL3 comprises the heavy-chain variable region and light-chain variable region of an anti-DLL3 antibody. In certain embodiments, the antigen-binding domain binds to DLL3 is a domain comprising a Fab structure.

Preferably, the anti-DLL3 antigen-binding domain comprises a Heavy chain variable region of any one of SEQ ID NOs: 15, 25, and 63 to 71, and a Light chain variable region of any one of SEQ ID NOs: 16, 26, and 72 to 74.

In some embodiments, the anti-DLL3 antigen-binding domain binds specifically to the extracellular domain of DLL3. In some embodiments, the anti-DLL3 antigen-binding domain binds specifically to an epitope within the extracellular domain of DLL3. In some embodiments, the anti-DLL3 antigen-binding domain binds to the DLL3 protein expressed on the surface of eukaryotic cells. In some embodiments, the anti-DLL3 antigen-binding domain binds to the DLL3 protein expressed on the surface of cancer cells.

In specific embodiments, the antigen-binding domain binds to DLL3 comprises any one of the antibody variable/constant region sequences shown in Tables 1A and 1B below.

Table 1A shows SEQ ID NOs of the generated anti-DLL3 antibodies.

TABLE 1A

| Antibody name | Variable region Heavy chain | Variable region Light chain | Constant region Heavy chain | Constant region Light chain |
|---|---|---|---|---|
| DLA0316-SG1 | 15 | 16 | 60 | 10 |
| D30316AE01-SG1 | 63 | 72 | 60 | 62 |
| D30316AE02-SG1 | 64 | 72 | 60 | 62 |
| D30316AE03-SG1 | 65 | 72 | 60 | 62 |
| DLA0841-SG1 | 25 | 26 | 60 | 10 |
| D30841AE05-SG1 | 66 | 73 | 60 | 62 |
| D30841AE08-SG1 | 67 | 73 | 60 | 62 |
| D30841AE11-SG1 | 67 | 74 | 60 | 62 |
| D30841AE12-SG1 | 68 | 73 | 60 | 62 |
| D30841AE13-SG1 | 69 | 73 | 60 | 62 |
| D30841AE14-SG1 | 70 | 73 | 60 | 62 |
| D30841AE15-SG1 | 71 | 73 | 60 | 62 |

Table 1B shows SEQ ID NOs of the HVR (CDR) sequences of the generated anti-DLL3 antibodies.

TABLE 1B

| Antibody name | Hyper variable region (HVR) HCDR1 | HCDR2 | HCDR3 | LCDR1 | LCDR2 | LCDR3 |
|---|---|---|---|---|---|---|
| DLA0316-SG1 | 27 | 28 | 29 | 30 | 31 | 32 |
| D30316AE01-SG1 | 27 | 28 | 29 | 30 | 31 | 32 |
| D30316AE02-SG1 | 27 | 75 | 29 | 30 | 31 | 32 |
| D30316AE03-SG1 | 27 | 76 | 29 | 30 | 31 | 32 |
| DLA0841-SG1 | 33 | 34 | 35 | 36 | 37 | 38 |
| D30841AE05-SG1 | 77 | 78 | 79 | 36 | 37 | 38 |
| D30841AE08-SG1 | 77 | 78 | 80 | 36 | 37 | 38 |
| D30841AE11-SG1 | 77 | 78 | 80 | 36 | 37 | 81 |
| D30841AE12-SG1 | 77 | 78 | 80 | 36 | 37 | 38 |
| D30841AE13-SG1 | 77 | 78 | 80 | 36 | 37 | 38 |
| D30841AE14-SG1 | 77 | 78 | 80 | 36 | 37 | 38 |
| D30841AE15-SG1 | 77 | 78 | 80 | 36 | 37 | 38 |

In specific embodiments, the antigen-binding domain binds to DLL3 is a domain that comprises an antibody variable fragment that competes for binding to DLL3 with any one of the antibody variable regions shown in Table 1A, or competes for binding to DLL3 with any antibody variable fragment that comprises the HVR sequence identical with the HVR regions of the antibody variable regions shown in Table 1A, or competes for binding to DLL3 with any antibody variable fragment that comprises the HVR sequence identical with the ones shown in Table 1B. In specific embodiments, the antigen-binding domain binds to DLL3 is a domain that comprises an antibody variable fragment that binds to the same epitope within DLL3 as any one of the antibody variable regions shown in Table 1A, or binds to the same epitope within DLL3 as any antibody variable fragment that comprises the HVR sequence identical with the HVR regions of the antibody variable regions shown in Table 1A, or binds to the same epitope within DLL3 as any antibody variable fragment that comprises the HVR sequence identical with the ones shown in Table 1B.

Alternatively, the antigen-binding domain binds to DLL3 comprises an antibody variable fragment that competes for binding to DLL3 with any one of the above-mentioned antibody variable fragments. Alternatively, the antigen-binding domain binds to DLL3 comprises an antibody variable fragment that binds to the same epitope to which any one of the above-mentioned antibody variable fragments binds on DLL3.

Antigen-Binding Domains Bind to T Cell Receptor Complex

The phrase "an antigen-binding domain binds to T cell receptor complex" or "an anti-T cell receptor complex antigen-binding domain" as used herein refers to an antigen-binding domain that specifically binds to the whole or a portion of a partial peptide of a T cell receptor complex. The T cell receptor complex may be a T cell receptor itself, or an adaptor molecule constituting a T cell receptor complex along with a T cell receptor. CD3 is suitable as an adaptor molecule.

In certain embodiments, the antigen-binding domain binds to T cell receptor complex is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to T cell receptor complex is a domain comprising an antibody variable fragment. Domains comprising an antibody variable fragment may be provided from variable domains of one or a plurality of antibodies.

In certain embodiments, the antigen-binding domain binds to T cell receptor complex comprises the heavy-chain variable region and light-chain variable region of an anti-T cell receptor complex antibody. In certain embodiments, the antigen-binding domain binds to T cell receptor complex-binding activity is a domain comprising a Fab structure.

Antigen-Binding Domains Bind to T Cell Receptor

The phrase "an antigen-binding domain binds to T cell receptor" or "an anti-T cell receptor antigen-binding domain" as used herein refers to an antigen-binding domain that specifically binds to the whole or a portion of a partial peptide of a T cell receptor. The portion of a T cell receptor to which the antigen-binding domain binds may be a variable region of the T cell receptor or a constant region of the T cell receptor; however, an epitope present in the constant region is preferred. Examples of the constant region sequence include the T cell receptor alpha chain of RefSeq Accession No. CAA26636.1 (SEQ ID NO: 104), the T cell receptor beta chain of RefSeq Accession No. C25777 (SEQ ID NO: 105), the T cell receptor gamma 1 chain of RefSeq Accession No. A26659 (SEQ ID NO: 106), the T cell receptor gamma 2 chain of RefSeq Accession No. AAB63312.1 (SEQ ID NO: 107), and the T cell receptor delta chain of RefSeq Accession No. AAA61033.1 (SEQ ID NO: 108).

In certain embodiments, the antigen-binding domain binds to T cell receptor is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to T cell receptor is a domain comprising an antibody variable fragment. Domains comprising an antibody variable fragment may be provided from variable domains of one or a plurality of antibodies.

In certain embodiments, the antigen-binding domain binds to T cell receptor comprises the heavy-chain variable region and light-chain variable region of an anti-T cell receptor antibody. In certain embodiments, the antigen-binding domain binds to T cell receptor is a domain comprising a Fab structure.

Antigen-Binding Domains Bind to CD3

The phrase "an antigen-binding domain binds to CD3" or "an anti-CD3 antigen-binding domain" as used herein refers to an antigen-binding domain that specifically binds to the whole or a portion of a partial peptide of CD3. The antigen-binding domain binds to CD3 may be any epitope-binding domain as long as the epitope exists in the gamma-chain, delta-chain, or epsilon-chain sequence that constitutes human CD3. Regarding the structure of the gamma chain, delta chain, or epsilon chain constituting CD3, their polynucleotide sequences are disclosed in RefSeq Accession NOs. NM_000073.2, NM_000732.4 and NM_000733.3, and their polypeptide sequences are shown in NP_000064.1 (SEQ ID NO: 109), NP_000723.1 (SEQ ID NO: 110), and NP_000724.1 (SEQ ID NO: 111) (RefSeq accession numbers). In some embodiments, an antigen-binding molecule or antibody of the present invention comprises a domain comprising an antigen variable region that binds to CD3 epsilon chain.

In certain embodiments, the antigen-binding domain binds to CD3 is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc. In specific embodiments, the antigen-binding domain binds to CD3 is a domain comprising an antibody variable fragment. Domains comprising an antibody variable fragment may be provided from variable domains of one or a plurality of antibodies.

In certain embodiments, the antigen-binding domain binds to CD3 comprises the heavy-chain variable region and light-chain variable region of an anti-CD3 antibody. In certain embodiments, the antigen-binding domain binds to CD3 is a domain comprising a Fab structure.

The anti-CD3 antigen-binding domains of the present invention may bind to any epitope, as long as the epitope is located within the gamma chain, delta chain, or epsilon chain sequence forming human CD3. In the present invention, preferred anti-CD3 antigen-binding domains include those comprising a CD3 antibody light-chain variable region (VL) and a CD3 antibody heavy-chain variable region (VH), which bind to an epitope in the extracellular domain of the epsilon chain of a human CD3 complex. Such preferred anti-CD3 antigen-binding domains include those comprising a CD3 antibody light-chain variable region (VL) and a CD3 antibody heavy-chain variable region (VH) of the OKT3 antibody (Proc. Natl. Acad. Sci. USA (1980) 77, 4914-4917) or various known CD3 antibodies such as an antibody with the light-chain variable region (VL) of NCBI Accession No. AAB24132 and the heavy-chain variable region (VH) of NCBI Accession No. AAB24133 (Int. J. Cancer Suppl. 7, 45-50 (1992)). Furthermore, such appropriate anti-CD3 antigen-binding domains include those derived from a CD3 antibody with desired characteristics, which are obtained by immunizing a desired animal with the gamma chain, delta chain, or epsilon chain forming human CD3 by the above-described methods. Appropriate anti-CD3 antibodies from which an anti-CD3 antigen-binding domain is derived include human antibodies and antibodies appropriately humanized as described above.

Preferably, the anti-CD3 antigen-binding domain comprises a Heavy chain variable region of any one of the heavy chain variable region shown in Table 2B, and a Light chain variable region of any one of the light chain variable region shown in Table 2B.

In some embodiments, the anti-CD3 antigen-binding domain havi binds specifically to CD3 epsilon chain. In some embodiments, the anti-CD3 antigen-binding domain binds specifically to an epitope within CD3 epsilon chain. In some embodiments, the anti-CD3 antigen-binding domain binds to the CD3 epsilon chain expressed on the surface of eukaryotic cells. In some embodiments, the anti-CD3 antigen-binding domain binds to the CD3 epsilon chain expressed on the surface of T cells.

In specific embodiments, the antigen-binding domain binds to CD3 comprises any one of the antibody variable region sequences shown in Tables 2A below. In specific embodiments, the antigen-binding domain binds to CD3 comprises any one of the combinations of the heavy chain variable region and light chain variable region shown in Table 2A. In specific embodiments, the antigen-binding domain binds CD3 comprises the HVR sequences comprised in the antibody variable regions shown in Table 2A.

Table 2A shows SEQ ID NOs of the variable regions of the anti-CD3 antigen-binding domain.

TABLE 2A

| Name | SEQ ID NOs Heavy chain variable region | Light chain variable region |
|---|---|---|
| No. 12 | 57 | 58 |
| TR01 | 98 | 103 |
| AN104 | 99 | 103 |
| AN119 | 100 | 103 |
| AN121 | 101 | 103 |
| AN395 | 102 | 103 |
| hu40G5c | 298 | 299 |
| 40G5c | 300 | 301 |
| 38E4v1 | 302 | 303 |
| 38E4v2 | 304 | 305 |
| 38E4v3 | 306 | 307 |
| 38E4v4 | 308 | 309 |
| 38E4v5 | 310 | 311 |
| 38E4v6 | 312 | 313 |
| 38E4v7 | 314 | 315 |
| 38E4v8 | 316 | 317 |
| 38E4v9 | 318 | 319 |
| 38E4c | 320 | 321 |
| UCHT1v9 | 322 | 323 |
| UCHT1 v1 | 324 | 325 |
| UCHT1 vM1 | 326 | 327 |
| SP34 | 328 | 329 |
| SP34v52 | 330 | 331 |
| hu41D9a | 332 | 333 |
| 41 D9a | 334 | 335 |
| hu13A3 | 336 | 337 |
| 13A3.v2 | 338 | 339 |

TABLE 2A-continued

| Name | SEQ ID NOs Heavy chain variable region | Light chain variable region |
|---|---|---|
| 13A3 | 340 | 341 |
| hu30A1 | 342 | 343 |
| 30A1 | 344 | 345 |
| 30A1 .v2 | 346 | 347 |
| 21A9 | 348 | 349 |
| 21B2 | 350 | 351 |
| 125A1 | 552 | 353 |
| 72H6 | 354 | 355 |
| 19B1 | 356 | 357 |
| 71 H7 | 358 | 359 |
| 14C7 | 360 | 361 |
| 127B3 | 362 | 363 |
| 18F12 | 364 | 365 |
| 27H5-1 | 366 | 367 |
| 39B7 | 368 | 369 |
| 40D2 | 370 | 371 |
| 79B7 | 372 | 373 |
| 95A2 | 374 | 375 |
| 118G9 | 376 | 377 |
| Rab17 | 378 | 379 |
| 38E4 | 380 | 381 |
| 1217 | 382 | 383 |
| hu38E4 | 384 | 385 |
| 40G5 | 386 | 387 |
| hu40G5 | 388 | 389 |
| humuSP34 | 390 | 391 |

In specific embodiments, the antigen-binding domain binds to CD3 comprises any one of the combinations of HVR sequences shown in Table 2B below.

Table 2B shows SEQ ID NOs of the HVR (CDR) sequences of the anti-CD3 antigen-binding domain.

TABLE 2B

| Name | SEQ ID NOs HVR-H1 | HVR-H2 | HVR-H3 | HVR-L1 | HVR-L2 | HVR-L3 |
|---|---|---|---|---|---|---|
| 40G5c | 136 | 137 | 138 | 139 | 140 | 141 |
| 38E4v1 | 142 | 143 | 144 | 145 | 146 | 147 |
| 38E4v2 | 142 | 143 | 148 | 145 | 146 | 147 |
| 38E4v3 | 142 | 143 | 144 | 145 | 146 | 149 |
| 38E4v4 | 142 | 143 | 144 | 145 | 146 | 150 |
| 38E4v5 | 142 | 143 | 144 | 145 | 146 | 151 |
| 38E4v6 | 142 | 143 | 152 | 145 | 146 | 147 |
| 38E4v7 | 142 | 143 | 153 | 145 | 146 | 147 |
| 38E4v8 | 142 | 143 | 154 | 145 | 146 | 147 |
| 38E4v9 | 142 | 143 | 155 | 145 | 146 | 147 |
| 38E4c | 142 | 143 | 156 | 145 | 146 | 157 |
| UCHT1v9 | 158 | 159 | 160 | 161 | 162 | 163 |
| UCHT1 v1 | 158 | 164 | 160 | 161 | 162 | 163 |
| UCHT1 vM1 | 158 | 165 | 160 | 161 | 162 | 163 |
| SP34v52 | 166 | 167 | 168 | 169 | 170 | 171 |
| 41 D9a | 172 | 173 | 174 | 175 | 176 | 177 |
| 13A3 | 178 | 179 | 180 | 181 | 182 | 183 |
| 30A1 | 194 | 185 | 186 | 187 | 188 | 189 |
| 30A1 .v2 | 190 | 191 | 192 | 193 | 194 | 195 |
| h21A9 | 196 | 197 | 198 | 199 | 200 | 201 |
| 21B2 | 202 | 203 | 204 | 205 | 206 | 207 |
| 125A1 | 208 | 209 | 210 | 211 | 212 | 213 |
| 72H6 | 214 | 215 | 216 | 217 | 218 | 219 |
| 19B1 | 220 | 221 | 222 | 223 | 224 | 225 |
| 71 H7 | 226 | 227 | 228 | 229 | 230 | 231 |
| 14C7 | 232 | 233 | 234 | 235 | 236 | 237 |
| 127B3 | 238 | 239 | 240 | 241 | 242 | 243 |
| 18F12 | 244 | 245 | 246 | 247 | 248 | 249 |
| 27H5-1 | 250 | 251 | 252 | 253 | 354 | 255 |
| 39B7 | 256 | 257 | 258 | 359 | 260 | 261 |
| 40D2 | 262 | 263 | 264 | 265 | 266 | 267 |
| 79B7 | 268 | 269 | 270 | 271 | 272 | 273 |
| 95A2 | 274 | 275 | 276 | 277 | 278 | 279 |

TABLE 2B-continued

| | SEQ ID NOs | | | | | |
|---|---|---|---|---|---|---|
| Name | HVR-H1 | HVR-H2 | HVR-H3 | HVR-L1 | HVR-L2 | HVR-L3 |
| 118G9 | 280 | 281 | 282 | 283 | 284 | 285 |
| Rab17 | 286 | 287 | 288 | 389 | 290 | 291 |
| 43H8 | 292 | 293 | 294 | 295 | 296 | 297 |

In specific embodiments, the antigen-binding domain binds to CD3 is a domain that comprises an antibody variable fragment that competes for binding to CD3 with any one of the antibody variable regions shown in Table 2A, or competes for binding to CD3 with any antibody variable fragment that comprises the HVR sequence identical with the HVR regions of the antibody variable regions shown in Table 2A, or competes for binding to CD3 with any antibody variable fragment that comprises the HVR sequence identical with the ones shown in Table 2B. In specific embodiments, the antigen-binding domain binds to CD3 is a domain that comprises an antibody variable fragment that binds to the same epitope within CD3 as any one of the antibody variable regions shown in Table 2A, or binds to the same epitope within CD3 as any antibody variable fragment that comprises the HVR sequence identical with the HVR regions of the antibody variable regions shown in Table 2A, or binds to the same epitope within CD3 as any antibody variable fragment that comprises the HVR sequence identical with the ones shown in Table 2B.

Alternatively, the antigen-binding domain binds to CD3 comprises an antibody variable fragment that competes for binding to CD3 with any one of the above-mentioned antibody variable fragments/antibody variable regions. Alternatively, the antigen-binding domain binds to CD3 comprises an antibody variable fragment that binds to the same epitope to which any one of the above-mentioned antibody variable fragments/antibody variable regions bind on CD3.

Multispecific Antigen-Binding Molecules

"Multispecific antigen-binding molecules" refers to antigen-binding molecules that bind specifically to more than one antigen. In a favorable embodiment, multispecific antigen-binding molecules of the present invention comprise two or more antigen-binding domains, and different antigen-binding domains bind specifically to different antigens.

The multispecific antigen-binding molecule of the present invention comprises a first antigen-binding domain binds to DLL3, and a second antigen-binding domain binds to T cell receptor complex. The combinations of an antigen-binding domain binds to DLL3 selected from those described in "Antigen-binding domains bind to DLL3" above and an antigen-binding domain binds to T cell receptor complex selected from those described in "Antigen-binding domains bind to T-cell receptor complex" to "Antigen-binding domains bind to CD3" above can be used.

For example, the first antigen-binding domain is a domain comprising antibody heavy-chain and light-chain variable regions, and/or the second antigen-binding domain is a domain comprising antibody heavy-chain and light-chain variable regions. Alternatively, the first antigen-binding domain is a domain comprising an antibody variable fragment, and/or the second antigen-binding domain is a domain comprising an antibody variable fragment. Alternatively, the first antigen-binding domain is a domain comprising a Fab structure, and/or the second antigen-binding domain is a domain comprising a Fab structure.

In certain embodiments, the present invention provides a multispecific antigen-binding molecule comprising a first antigen-binding domain binds to DLL3, and a second antigen-binding domain binds to T cell receptor complex. In certain embodiments, the present invention provides bispecific antigen-binding molecules that comprise a first antigen-binding domain binds to DLL3, a second antigen-binding domain binds to T cell receptor complex, and a domain comprising an Fc region that has a reduced Fc gamma receptor-binding activity. The Fc region may have a reduced Fc gamma receptor-binding activity compared with the Fc domain of an IgG1, IgG2, IgG3, or IgG4 antibody. In an embodiment, the Fc region is an Fc region with an amino acid mutation at any of the Fc region-constituting amino acids of SEQ ID NOs: 112 to 115 (IgG1 to IgG4).

In certain embodiments, the present invention provides bispecific antibodies that comprise a first antibody variable fragment binds to DLL3, and a second antibody variable fragment binds to CD3. In certain embodiments, the present invention provides bispecific antibodies that comprise a first antibody variable fragment binds to DLL3, a second antibody variable fragment binds to CD3, and an Fc region that has a reduced Fc gamma receptor-binding activity. In certain embodiments, the present invention provides bispecific antibodies that comprise a first antibody variable fragment binds to DLL3, a second antibody variable fragment binds to CD3 epsilon chain, and an Fc region that has a reduced Fe gamman receptor-binding activity compared with naturally occurring IgG Fc regions.

Examples of a preferred embodiment of the "multispecific antigen-binding molecule" of the present invention include multispecific antibodies. When an Fc region with reduced Fc gamma receptor-binding activity is used as the multispecific antibody Fc region, an Fc region derived from the multispecific antibody may be used appropriately. Bispecific antibodies are particularly preferred as the multispecific antibodies of the present invention. In this case, a bispecific antibody is an antibody having two different specificities. IgG-type bispecific antibodies can be secreted from a hybrid hybridoma (quadroma) produced by fusing two types of hybridomas that produce IgG antibodies (Milstein et al., Nature (1983) 305, 537-540).

Furthermore, IgG-type bispecific antibodies are secreted by introducing the genes of L chains and H chains constituting the two types of IgGs of interest, i.e., a total of four genes, into cells, and co-expressing them. However, the number of combinations of H and L chains of IgG that can be produced by these methods is theoretically ten combinations. Accordingly, it is difficult to purify an IgG comprising the desired combination of H and L chains from ten types of IgGs. Furthermore, theoretically, the amount of secretion of the IgG having the desired combination will decrease remarkably, and therefore large-scale culturing will be necessary, and production costs will increase further.

Therefore, techniques for promoting the association among H chains and between L and H chains having the desired combinations can be applied to the multispecific antigen-binding molecules of the present invention.

For example, techniques for suppressing undesired H-chain association by introducing electrostatic repulsion at the interface of the second constant region or the third constant region of the antibody H chain (CH2 or CH3) can be applied to multispecific antibody association (WO2006/106905).

In the technique of suppressing unintended H-chain association by introducing electrostatic repulsion at the interface of CH2 or CH3, examples of amino acid residues in contact at the interface of the other constant region of the H chain include regions corresponding to the residues at EU numbering positions 356, 439, 357, 370, 399, and 409 in the CH3 region.

More specifically, examples include an antibody comprising two types of H-chain CH3 regions, in which one to three pairs of amino acid residues in the first H-chain CH3 region, selected from the pairs of amino acid residues indicated in (1) to (3) below, carry the same type of charge: (1) amino acid residues comprised in the H chain CH3 region at EU numbering positions 356 and 439; (2) amino acid residues comprised in the H-chain CH3 region at EU numbering positions 357 and 370; and (3) amino acid residues comprised in the H-chain CH3 region at EU numbering positions 399 and 409.

Furthermore, the antibody may be an antibody in which pairs of the amino acid residues in the second H-chain CH3 region which is different from the first H-chain CH3 region mentioned above, are selected from the aforementioned pairs of amino acid residues of (1) to (3), wherein the one to three pairs of amino acid residues that correspond to the aforementioned pairs of amino acid residues of (1) to (3) carrying the same type of charges in the first H-chain CH3 region mentioned above carry opposite charges from the corresponding amino acid residues in the first H-chain CH3 region mentioned above.

Each of the amino acid residues indicated in (1) to (3) above come close to each other during association. Those skilled in the art can find out positions that correspond to the above-mentioned amino acid residues of (1) to (3) in a desired H-chain CH3 region or H-chain constant region by homology modeling and such using commercially available software, and amino acid residues of these positions can be appropriately subjected to modification.

In the antibodies mentioned above, "charged amino acid residues" are preferably selected, for example, from amino acid residues included in either one of the following groups:

(a) glutamic acid (E) and aspartic acid (D); and (b) lysine (K), arginine (R), and histidine (H).

In the above-mentioned antibodies, the phrase "carrying the same charge" means, for example, that all of the two or more amino acid residues are selected from the amino acid residues included in either one of groups (a) and (b) mentioned above. The phrase "carrying opposite charges" means, for example, that when at least one of the amino acid residues among two or more amino acid residues is selected from the amino acid residues included in either one of groups (a) and (b) mentioned above, the remaining amino acid residues are selected from the amino acid residues included in the other group.

In a preferred embodiment, the antibodies mentioned above may have their first H-chain CH3 region and second H-chain CH3 region crosslinked by disulfide bonds.

In the present invention, amino acid residues subjected to modification are not limited to the above-mentioned amino acid residues of the antibody variable regions or the antibody constant regions. Those skilled in the art can identify the amino acid residues that form an interface in mutant polypeptides or heteromultimers by homology modeling and such using commercially available software; and amino acid residues of these positions can then be subjected to modification so as to regulate the association.

Other known techniques can also be used for the association of multispecific antibodies of the present invention. Fc region-containing polypeptides comprising different amino acids can be efficiently associated with each other by substituting an amino acid side chain present in one of the H-chain Fc regions of the antibody with a larger side chain (knob), and substituting an amino acid side chain present in the corresponding Fc region of the other H chain with a smaller side chain (hole) to allow placement of the knob within the hole (WO1996/027011; Ridgway J B et al., Protein Engineering (1996) 9, 617-621; Merchant A. M. et al. Nature Biotechnology (1998) 16, 677-681; and US20130336973).

In addition, other known techniques can also be used for formation of multispecific antibodies of the present invention. Association of polypeptides having different sequences can be induced efficiently by complementary association of CH3 using a strand-exchange engineered domain CH3 produced by changing part of one of the H-chain CH3s of an antibody to a corresponding IgA-derived sequence and introducing a corresponding IgA-derived sequence into the complementary portion of the other H-chain CH3 (Protein Engineering Design & Selection, 23; 195-202, 2010). This known technique can also be used to efficiently form multispecific antibodies of interest.

In addition, technologies for antibody production using association of antibody CH1 and CL and association of VH and VL as described in WO 2011/028952, WO2014/018572, and Nat Biotechnol. 2014 February; 32(2):191-8; technologies for producing bispecific antibodies using separately prepared monoclonal antibodies in combination (Fab Arm Exchange) as described in WO2008/119353 and WO2011/131746; technologies for regulating association between antibody heavy-chain CH3s as described in WO2012/058768 and WO2013/063702; technologies for producing bispecific antibodies composed of two types of light chains and one type of heavy chain as described in WO2012/023053; technologies for producing bispecific antibodies using two bacterial cell strains that individually express one of the chains of an antibody comprising a single H chain and a single L chain as described by Christoph et al. (Nature Biotechnology Vol. 31, p 753-758 (2013)); and such may be used for the formation of multispecific antibodies.

Alternatively, even when a multispecific antibody of interest cannot be formed efficiently, a multispecific antibody of the present invention can be obtained by separating and purifying the multispecific antibody of interest from the produced antibodies. For example, a method for enabling purification of two types of homomeric forms and the heteromeric antibody of interest by ion-exchange chromatography by imparting a difference in isoelectric points by introducing amino acid substitutions into the variable regions of the two types of H chains has been reported (WO2007114325). To date, as a method for purifying heteromeric antibodies, methods using Protein A to purify a heterodimeric antibody comprising a mouse IgG2a H chain that binds to Protein A and a rat IgG2b H chain that does not bind to Protein A have been reported (WO98050431 and WO95033844). Furthermore, a heterodimeric antibody can be purified efficiently on its own by using H chains comprising substitution of amino acid residues at EU numbering positions 435 and 436, which is the IgG-Protein A binding site, with Tyr, His, or such which are amino acids that yield a different Protein A affinity, or using H chains with a different protein A affinity, to change the interaction of each of the H chains with Protein A, and then using a Protein A column.

Alternatively, a common L chain that can provide binding ability to a plurality of different H chains can be obtained and used as the common L chain of a multispecific antibody. Efficient expression of a multispecific IgG can be achieved by introducing the genes of such a common L chain and a plurality of different H chains into cells to express the IgG (Nature Biotechnology (1998) 16, 677-681). A method for selecting a common L chain that shows a strong binding ability to any of the different H chains can also be used when selecting the common H chain (WO 2004/065611).

Furthermore, an Fc region whose Fc region C-terminal heterogeneity has been improved can be appropriately used as an Fc region of the present invention. More specifically, the present invention provides Fc regions produced by deleting glycine at position 446 and lysine at position 447 as specified by EU numbering from the amino acid sequences of two polypeptides constituting an Fc region derived from IgG1, IgG2, IgG3, or IgG4.

A plurality, such as two or more, of these technologies can be used in combination. Furthermore, these technologies can be appropriately and separately applied to the two H chains to be associated. Furthermore, these techniques can be used in combination with the above-mentioned Fc region which has reduced binding activity to an Fc gamma receptor. Furthermore, an antigen-binding molecule of the present invention may be a molecule produced separately so that it has the same amino acid sequence, based on the antigen-binding molecule subjected to the above-described modifications.

Preferably, the antigen-binding molecule of the present invention may comprise a first antigen-binding domain binds to DLL3, and a second antigen-binding domain binds to T cell receptor complex. In an embodiment, the second antigen-binding domain binds to T cell receptor. In another embodiment, the second antigen-binding domain binds to CD3 epsilon chain. In an embodiment, the first antigen-binding domain binds to human DLL3. In a further embodiment, the first antigen-binding domain binds to DLL3 on the surface of a eukaryotic cell. In an embodiment, the first antigen-binding domain binds to human DLL3 on the surface of a eukaryotic cell, preferably a cancer cell.

The phrase "anti-DLL3 arm" in this specification refers to the antibody heavy chain and antibody light chain which binds to DLL3 in a bispecific antibody. The phrase "anti-CD3 arm" in this specification refers to the antibody heavy chain and antibody light chain which binds to CD3 in a bispecific antibody.

Preferably, the antigen-binding molecule of the present invention may have cellular cytotoxicity (also referred to as "cytotoxicity). In an embodiment, the cellular cytotoxicity is T cell-dependent cellular cytotoxicity (TDCC). In another embodiment, the cytotoxicity is a cellular cytotoxicity towards cells expressing DLL3 on their surfaces. The DLL3-expressing cells may be cancer cells.

In a preferred aspect, an antibody (or antigen-binding molecule) of the present invention has cytotoxicity (or cellular cytotoxicity), or preferably T cell-dependent cellular cytotoxicity (TDCC) against DLL3-expressing cells such as cancer cells. DLL3 may be expressed on the surface of such cells. The (cellular) cytotoxicity or TDCC of an antibody (or antigen-binding molecule) of the present invention can be evaluated by any suitable method known in the art. For example, the method described in some Examples can be used for measuring TDCC. In this case, the cytotoxic activity is assessed by the rate of cell growth inhibition by an antibody (or antigen-binding molecule) of the present invention. Cell growth is measured using a suitable analyzer such as xCELLigence Real-Time Cell Analyzer. Cancer cells are used as target cells, and they are seeded on a multi-well plate at a suitable cell concentration (for example, about $10^4$ cells/well). On the following day, a test antibody prepared at an appropriate concentration (for example, 0.001-10 nM) is added to the plate. After 15 minutes of reaction, a solution containing T cells (such as PBMC) is added thereto at a suitable effector (PBMC)/target (cancer cell) ratio such as the ratio of 10. The reaction is carried out with carbon dioxide gas. After the addition of T cells, the Cell Growth Inhibition (CGI) rate (%) is determined using the equation: CGI rate (%)=(A−B)×100/(A−1), where A represents the mean Cell Index value of wells without the antibody (or antigen-binding molecule), i.e., containing only target cells and T cells; and B represents the mean Cell Index value of wells with the antibody (or antigen-binding molecule). The Cell Index values used in the calculation are normalized values, i.e., the Cell Index value at the time point immediately before antibody addition is defined as 1. If the CGI rate of an antibody (or antigen-binding molecule) is high, i.e., has a significantly positive value, it can be said that the antibody (or antigen-binding molecule) has TDCC activity and is more preferable in the present invention.

Alternatively, cytotoxic activity can be assessed by the calcein-acetoxymethyl release assay. Cancer cells are used as target cells. The target cells are labeled with calcein-acetoxymethyl and then washed. A test antibody (for example, 0.001-10 nM) is pipetted into a plate and a calcein-labeled target cell suspension is added thereto. After leaving the plates at room temperature, an effector cell (such as PBMC) suspension is added thereto. After stirring the plate, it is centrifuged, and incubated in a $CO_2$ incubator. After the plate is stirred well and centrifuged, culture medium from each well is transferred to another plate. Absorbance (495 nm, reference 515 nm) is measured. For maximal release, the cells may be lysed with 0.5% NP-40. The fluorescence value of the culture medium background is subtracted from the value of the experimental release (A), the target cell spontaneous release (B), and the target cell maximal release (C). The cytotoxicity was calculated using the following formula: Cytotoxicity (%)=(A−B)/(C−B)×100. If this value of an antibody (or antigen-binding molecule) is high, i.e., has a significantly positive value, it can be said that the antibody (or antigen-binding molecule) has TDCC activity and is more preferable in the present invention.

Monospecific Antigen-Binding Molecules

The term "monospecific antigen-binding molecule" is used to refer to antigen-binding molecules that specifically bind to only one type of antigen. A favorable example of a monospecific antigen-binding molecule is an antigen-binding molecule that comprises a single type of antigen-binding domain. Monospecific antigen-binding molecules can comprise a single antigen-binding domain or a plurality of antigen-binding domains of the same type. A favorable example of monospecific antigen-binding molecules is a monospecific antibody. When the monospecific antigen-binding molecule is a monospecific antibody of the IgG form, the monospecific antibody comprises two antibody variable fragments that have the same antigen-binding specificity.

The monospecific antigen-binding molecule of the present invention comprises an antigen-binding domain binds to DLL3. The antigen-binding domain binds to DLL3 may be any one of those described in "Antigen-binding domains bind to DLL3" above.

The term "monospecific antigen-binding molecule binds to DLL3" refer to a monospecific antigen-binding molecule that is capable of binding DLL3 with sufficient affinity such that the antibody is useful as a diagnostic and/or therapeutic agent in targeting DLL3. In one embodiment, the extent of binding of a monospecific antigen-binding molecule binds to DLL3 to an unrelated, non-DLL3 protein is less than about 10% of the binding to DLL3 as measured, e.g., by a radioimmunoassay (RIA). In certain embodiments, a monospecific antigen-binding molecule binds to DLL3 has a dissociation constant (Kd) of 1 micro M or less, 100 nM or less, 10 nM or less, 1 nM or less, 0.1 nM or less, 0.01 nM or less, or 0.001 nM or less (e.g. 108 M or less, e.g. from 108 M to $10^{-13}$ M, e.g., from $10^{-9}$ M to 10-13 M).

In some embodiments, the monospecific antigen-binding molecule binds to DLL3 in the present invention comprises a functional Fc region possessing an effector function, such as C1q binding; CDC; Fc receptor binding; ADCC; phagocytosis; down regulation of cell surface receptors (e.g. B cell receptor; BCR).

Antibody-Dependent Cell-Mediated Cytotoxicity

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express Fc gamma RIII only, whereas monocytes express Fc gamma RI, Fc gamma RII, and Fc gamma RIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

Immunoconjugates

The invention also provides immunoconjugates comprising an antigen-binding molecule herein, for example a monospecific antigen-binding molecule binds to DLL3, conjugated to one or more cytotoxic agents, such as chemotherapeutic agents or drugs, growth inhibitory agents, toxic compounds, toxins (e.g., protein toxins, enzymatically active toxins of bacterial, fungal, plant, or animal origin, or fragments thereof), or radioactive isotopes. In some embodiments, the present invention provides an antigen-binding molecule or antibody that is conjugated to a toxic compound. In other words, the present invention provides an antibody-drug-conjugate compound that comprises an antigen-binding molecule or antibody.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antigen-binding molecule (such as a monospecific antigen-binding molecule binds to DLL3) as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antigen-binding molecule (such as a monospecific antigen-binding molecule binds to DLL3) as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antigen-binding molecule (such as a monospecific antigen-binding molecule binds to DLL3) and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A.).

Cancer

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

Tumor

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

In preferred embodiments, the cancer is a cancer (including cancer tissues or cells) expressing DLL3. In some embodiments, the cancer is pancreatic cancer, glioma, small cell lung cancer (SCLC), or melanoma.

Pharmaceutical Formulation

The term "pharmaceutical formulation" refers to a preparation which is in such form as to permit the biological activity of an active ingredient contained therein to be effective, and which contains no additional components which are unacceptably toxic to a subject to which the formulation would be administered.

Pharmaceutically Acceptable Carrier

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Treatment

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

In one aspect, the invention is based, in part, on multi-specific antigen-binding molecules that comprises a first antigen-binding domain binds to DLL3, and a second antigen-binding domain binds to T-cell receptor complex, and use thereof. Antigen-binding molecules and antibodies of the invention are useful, e.g., for the diagnosis or treatment of tumor, especially colorectal tumor and gastric tumor.

Pharmaceutical Composition

A pharmaceutical composition of the present invention, a therapeutic agent for inducing cellular cytotoxicity, a cell growth-suppressing agent, or an anticancer agent of the present invention may be formulated with different types of antigen-binding molecules, if needed. For example, the cytotoxic action against cells expressing an antigen can be enhanced by a cocktail of multiple antigen-binding molecules of the present invention.

If necessary, the antigen-binding molecules of the present invention may be encapsulated in microcapsules (microcapsules made from hydroxymethylcellulose, gelatin, poly[methylmethacrylate], and the like), and made into components of colloidal drug delivery systems (liposomes, albumin microspheres, microemulsions, nano-particles, and nanocapsules) (for example, see "Remington's Pharmaceutical Science 16th edition", Oslo Ed. (1980)). Moreover, methods for preparing agents as sustained-release agents are known, and these can be applied to the antigen-binding molecules of the present invention (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, cell growth-suppressing agents, or anticancer agents of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

Preferably, a pharmaceutical composition of the present invention comprises a antigen-binding molecule of the invention. In an embodiment, the composition is a pharmaceutical composition for use in inducing cellular cytotoxicity. In another embodiment, the composition is a pharmaceutical composition for use in treating or preventing cancer. Preferably, the cancer is an above-mentioned cancer. The pharmaceutical composition of the present invention can be used for treating or preventing cancer. Thus, the present invention provides a method for treating or preventing cancer, in which the antigen-binding molecule of the present invention is administered to a patient in need thereof.

Furthermore, the present invention provides use of an above-mentioned antigen-binding molecule or antibody in the manufacture of a pharmaceutical composition for treating or preventing cancer. The present invention also provides use of the antigen-binding molecule/antibody/pharmaceutical composition for treating or preventing cancer.

The present invention also provides methods for damaging cells expressing DLL3 or for suppressing the cell growth by contacting the cells expressing DLL3 with an antigen-binding molecule of the present invention that binds to DLL3. Monoclonal antibodies that bind to DLL3 are described above as an antigen-binding molecule of the present invention, which is included in the therapeutic agents for inducing cellular cytotoxicity, cell growth-suppressing agents, and anticancer agents of the present invention. Cells to which an antigen-binding molecule of the present invention binds are not particularly limited, as long as they express DLL3. Specifically, in the present invention, the preferred cancer antigen-expressing cells include pancreatic cancer cells, glioma cells, melanoma cells, or small cell lung cancer (SCLC) cells.

In the present invention, “contact” can be carried out, for example, by adding an antigen-binding molecule of the present invention to culture media of cells expressing DLL3 cultured in vitro. In this case, an antigen-binding molecule to be added can be used in an appropriate form, such as a solution or solid prepared by lyophilization or the like. When the antigen-binding molecule of the present invention is added as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The added concentration is not particularly limited; however, the final concentration in a culture medium is preferably in a range of 1 pg/ml to 1 g/ml, more preferably 1 ng/ml to 1 mg/ml, and still more preferably 1 micro g/ml to 1 mg/ml.

In another embodiment of the present invention, “contact” can also be carried out by administration to nonhuman animals transplanted with DLL3-expressing cells in vivo or to animals having cancer cells expressing DLL3 endogenously. The administration method may be oral or parenteral. Parenteral administration is particularly preferred. Specifically, the parenteral administration method includes injection, nasal administration, pulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, an appropriate administration method can be selected according to the age and symptoms of an animal subject. When the antigen-binding molecule is administered as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The administered dose can be selected, for example, from the range of 0.0001 to 1,000 mg per kg of body weight for each administration. Alternatively, the dose can be selected, for example, from the range of 0.001 to 100,000 mg/body for each patient. However, the dose of an antigen-binding molecule of the present invention is not limited to these examples.

The methods described below are preferably used as a method for assessing or determining cellular cytotoxicity caused by contacting an antigen-binding molecule of the present invention with DLL3-expressing cells to which the antigen-binding domain forming the antigen-binding molecules of the present invention binds. The methods for assessing or determining the cytotoxic activity in vitro include methods for determining the activity of cytotoxic T-cells or the like. Whether an antigen-binding molecule of the present invention has the activity of inducing T-cell mediated cellular cytotoxicity can be determined by known methods (see, for example, Current protocols in Immunology, Chapter 7. Immunologic studies in humans, Editor, John E, Coligan et al., John Wiley & Sons, Inc., (1993)). In the cytotoxicity assay, an antigen-binding molecule whose antigen-binding domain binds to an antigen different from DLL3 and which is not expressed in the cells is used as a control antigen-binding molecule. The control antigen-binding molecule is assayed in the same manner. Then, the activity is assessed by testing whether an antigen-binding molecule of the present invention exhibits a stronger cytotoxic activity than that of a control antigen-binding molecule.

Meanwhile, the in vivo cytotoxic activity is assessed or determined, for example, by the following procedure. Cells expressing the antigen to which the antigen-binding domain forming an antigen-binding molecule of the present invention binds are transplanted intracutaneously or subcutaneously to a nonhuman animal subject. Then, from the day of transplantation or thereafter, a test antigen-binding molecule is administered into vein or peritoneal cavity every day or at intervals of several days. The tumor size is measured over time. Difference in the change of tumor size can be defined as the cytotoxic activity. As in an in vitro assay, a control antigen-binding molecule is administered. The antigen-binding molecule of the present invention can be judged to have cytotoxic activity when the tumor size is smaller in the group administered with the antigen-binding molecule of the present invention than in the group administered with the control antigen-binding molecule.

An MTT method and measurement of isotope-labeled thymidine uptake into cells are preferably used to assess or determine the effect of contact with an antigen-binding molecule of the present invention to suppress the growth of cells expressing an antigen to which the antigen-binding domain forming the antigen-binding molecule binds. Meanwhile, the same methods described above for assessing or determining the in vivo cytotoxic activity can be used preferably to assess or determine the activity of suppressing cell growth in vivo.

The present invention also provides kits for use in a method of the present invention, which contain an antigen-binding molecule of the present invention or an antigen-binding molecule produced by a method of the present invention. The kits may be packaged with an additional pharmaceutically acceptable carrier or medium, or instruction manual describing how to use the kits, etc.

In addition, the present invention relates to antigen-binding molecules of the present invention or antigen-binding molecules produced by a method of the present invention for use in a method of the present invention.

In another embodiment, internalizing antibodies are provided. In other words, the present invention provides an antibody or an antigen-binding molecule that has internalization activity. Such Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be used. For example, based upon the variable region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA 90: 7889-7893 (1993). The internalization activity of an antibody (or an antigen-binding molecule) can be determined, for example, by the method described in Reference Example 18 of European Patent Publication No. 3015115 (WO2014/208482).

Expression and Purification of DLL3 Extracellular Domain (ECD) Fragment Proteins A DLL3 extracellular domain (ECD) fragment protein (or truncated variants thereof), optionally with Flag-tag on C-terminus, can be expressed transiently using appropriate vectors and cells. Cultivation supernatants containing the proteins are applied to a column packed with affinity resin and eluted. Fractions containing the proteins are collected and subsequently applied to a filtration column equilibrated with buffer. Fractions containing the proteins are then pooled and stored at −80 degrees Celsius (C) until use. ECD fragment proteins may be used for epitope mapping or competition assay by known methods or the methods described herein.

Establishment of Cell Lines Expressing DLL3

To establish a cell line expressing DLL3, a DLL3 cDNA is inserted into an expression vector, and this is introduced into cells by, for example, electroporation. After introduction, an agent for selection (such as Geneticin) is added, and the cells are cultured to obtain a cell line that is resistant to it. Transfected cell lines may be plated in a plate by limiting dilution, and expanded. The established cell line may be used for assessing TDCC activity of an antigen-binding molecule or antibody of the present invention against cells expressing DLL3.

Generation and Screening of Anti-DLL3 Antibodies (Monospecific)

Anti-DLL3 antibodies may be prepared, selected and assayed as described below. An animal such as rabbit is immunized with DLL3 or a fragment thereof. After the final immunization, the spleen and blood are collected from the immunized animal. Antigen-specific B-cells are stained and sorted with a cell sorter, and plated in plates at a density of one cell per well together with, e.g., EL4 cells (European Collection of Cell Cultures), and cultured. After cultivation, B-cell culture supernatants are collected for further analysis and pellets may be cryopreserved. ELISA screening may be conducted to test specificity of antibodies in B-cell culture supernatants. DLL3-expressing cells are immobilized onto a plate pre-coated with BSA and a biocompatible anchor for cell membrane. Immobilized cells are incubated with B-cell culture supernatants. The cells are washed, and, e.g., a goat anti-rabbit IgG polyclonal antibody HRP conjugate is added. The cells are further incubated on ice, and a substrate is added and optimal density is suitably analyzed. B-cell clones are screened for binding to DLL3-expressing cells, and clones are selected as DLL3-specific binders. The selected clones are purified from cryopreserved cell pellets. The DNAs of the antibody heavy chain variable regions are amplified by reverse transcription PCR and ligated with DNA encoding a human IgG1 heavy chain constant region, to form corresponding heavy chains. The DNAs of the antibody light chain variable regions are amplified by reverse transcription PCR and ligated with DNA encoding a light chain constant region, to form corresponding light chains. Cloned antibodies are expressed in cells, and purified from culture supernatants for functional evaluation. The monospecific antibodies may be used for producing anti-DLL3/anti-CD3 bispecific antibodies by known methods.

Epitope Mapping of Selected Anti-DLL3 Antibodies (Monospecific)

The structures of DLL3 and DLL3 ECD fragment proteins are schematically shown in FIG. 1. These DLL3 ECD fragment proteins may be used for epitope mapping of anti-DLL3 antibodies, for example, as described below. Plates are coated with a fragment protein, and blocked with a buffer. Blocking buffer is removed and an anti-DLL3 antibody is incubated with the immobilized protein, and washed with a buffer. Any suitable detection system including an anti-flag antibody can be used to assess antibody binding. For example, Monoclonal ANTI-FLAG M2-Peroxidase, Clone M2 (Sigma-Aldrich) is added and incubated and washed. Then, a substrate is added and optical density (e.g., OD405) is determined. The OD405 value represents the reactivity of the tested antibody against the fragment protein. Antibody epitopes can be inferred by testing which domain deletion (see FIG. 1) abrogates antibody binding. That is, if an antibody fails to bind to a certain deletion construct among a panel of sequential deletion constructs shortened, for example, from the N-terminus (FIG. 1), then it can be said that this construct does not contain the epitope of the antibody and longer deletion constructs to which the antibody can bind, or more specifically the N terminal region of the shortest one among such longer deletion constructs, contain the epitope of the antibody.

Functional Evaluation of Anti-DLL3/CD3 Bispecific Antibodies

Anti-DLL3/CD3 bispecific antibodies may be evaluated for their in vivo anti-tumor efficacy in a xenograft model, as described below. Cancer cell lines are transplanted into NOD scid mice, and the NOD scid mice with confirmed tumor formation are subjected to transplantation of T cells grown by in vitro culturing of human PBMCs. The mice (referred to as T cell-injected model) are treated by administration of the bispecific antibodies. For example, in anti-tumor efficacy tests of the bispecific antibodies using the T cell-injected model, the following may be performed. T cells are expansively cultured using PBMCs and a suitable media such as a T cell activation/expansion kit/human (MACS Miltenyi biotec). A human cancer cell line is mixed with a suitable support material such as Matrigel™ Basement Membrane Matrix (BD), and transplanted to a region of NOD scid mice. On the day before transplantation (day −1, when defining day 0 as the day of transplantation), an anti-asialo-GM1 antibody is administered intraperitoneally to the mice. On day 10 after the transplantation, the mice are separated into groups according to their body weight and tumor size, and the anti-asialo-GM1 antibody is administered again intraperitoneally to the mice. On the following day, T cells obtained by the aforementioned expansive culturing are transplanted intraperitoneally to the mice. Four hours after T cell transplantation, the anti-DLL3/CD3 bispecific antibodies are administered intravenously through the caudate vein. Anti-tumor activities (inhibition of tumor volume increase) can be assessed in the bispecific antibody-administered group compared to the solvent-administered control group.

Humanization and Optimization of Anti-DLL3 Monospecific Antibodies

Variable regions of the heavy and light chains of humanized DLL3 antibodies can be designed using human germline frameworks. The polynucleotides of the designed heavy and light chain variable regions are cloned into expression vectors containing the heavy chain constant region sequence and the light chain constant region sequence, respectively. Humanized antibodies are transiently expressed in cells, and BIAcore analysis is carried out as described above. Selected humanized antibodies are further optimized. To avoid chemical degradations such as deamidation, isomerization, succinimide formation, methionine and tryptophan oxidation and cysteinylation of unpaired cysteine in CDR regions, the sequences of the selected humanized antibodies may be mutated to 18 other amino acids, excluding the original amino acid and Cysteine. The variants are transiently expressed and purified by the method described above. Purified variant monoclonal antibodies are assessed by BIAcore using the method described above, and variants of interest which can bind to DLL3 as the parent antibody are selected. Antibodies with a combination of these mutations in the CDRs are then generated.

Competition Analysis of Anti-DLL3 Antibodies

Preparation of Biotin-Labelled Anti-DLL3 Antibodies

Variable heavy and light chain sequences (VH and VL) of anti-DLL3 antibodies are cloned into expression vectors. Anti-DLL3 antibodies may be labelled with NHS-PEG4-Biotin, thereby preparing biotin-labelled anti-DLL3 antibodies.

Octet Assay

Octet (registered trademark) RED384 (Fortebio) can be used to perform competitive binding assays by epitope binning for a panel of antibodies. A biotinylated antibody is loaded to a streptavidin (SA) biosensor. Next, the sensor is exposed to DLL3, followed by exposure to a second antibody. Raw data is processed using ForteBio's Data Analysis Software 7.0 and the antibody pairs are assessed for competitive binding. Additional binding by the second antibody indicates an unoccupied epitope (non-competitor), while no binding indicates epitope blocking (competitor). To determine if there is a competitive antibody binding, Antibody A is first immobilized to streptavidin biosensor and the sequential binding of the complex of antigen with Antibody B is measured. The competition ratio of Antibody B to Antibody A is calculated using the following equation:

$$\text{Competition Ratio(Antibody } B \text{ to Antibody } A\text{)} = [\text{Binding Response(Antibody } B\text{-Antigen)}] / [\text{Binding Response(Antigen-Antibody } A\text{)}]$$

If the competition ratio is low, i.e., close to 0, then it can be said that Antibody A and Antibody B do not compete with each other for the same epitope.

Preparation of an Anti-DLL3/Anti-CD3 Bispecific Antibody

An anti-DLL3 monospecific antibody and an anti-CD3 antibody can be used to generate an anti-DLL3/CD3 bispecific antibody using a conventional method published elsewhere. The anti-CD3 antibody used may bind to an epitope within a region in CD3 epsilon chain. The bispecific antibody generated may contain a silent Fc with attenuated affinity for the Fc gamma receptor. In addition, the Fab arm exchange technique reported in, e.g., WO 2016159213 may be used to make the bispecific antibody.

BIAcore Analysis for Binding Affinity Evaluation of Anti-DLL3 Arm (or Anti-CD3 Arm) in the Anti-DLL3/CD3 Bispecific Antibodies Binding affinity of anti-DLL3 arm (or anti-CD3 arm) in the anti-DLL3/CD3 antibodies to DLL3 can be assessed, e.g., at pH 7.4 and 37 degrees C. using BIAcore. For example, anti-human Fc (GE Healthcare) is immobilized onto all flow cells of a CM4 sensor chip using amine coupling kit (GE Healthcare). The bispecific antibodies are captured onto the anti-Fc sensor surface, and then DLL3 (or CD3) is injected over the flow cell. Antibodies and analytes may be prepared in ACES pH 7.4 containing 20 mM ACES, 150 mM NaCl, 0.05% Tween 20, 0.005% $NaN_3$. Sensor surface is regenerated each cycle with 3M $MgCl_2$. Binding affinity is determined by processing and fitting the data to 1:1 binding model.

All documents cited herein are incorporated herein by reference.

EXAMPLES

The following are examples of methods and compositions of the invention. It is understood that various other embodiments may be practiced, given the general description provided above.

Example 1. Expression and Purification of Human DLL3 Extracellular Domain (ECD) Fragment Proteins and Cynomolgus DLL3 ECD Protein As human DLL3 extracellular domain (ECD) fragment proteins, human DLL3 ECD with Flag-tag (SEQ ID NO: 135) on C-terminus (SEQ ID NO: 1, hereinafter referred to as del0) and truncated human DLL3 ECD variants with Flag-tag on C-terminus (SEQ ID NOs: 2 to 7, hereinafter referred to as del1 to del6, respectively) were expressed transiently using FreeStyle 293-F Cells (Thermo Fisher Scientific). Cultivation supernatants containing human DLL3 ECD fragment proteins were applied to a column packed with anti-Flag M2 affinity resin (Sigma) and eluted with Flag peptide (Sigma). Fractions containing human DLL3 ECD fragment proteins were collected and subsequently applied to a Superdex 200 gel filtration column (GE healthcare) equilibrated with 1×D-PBS. Fractions containing human DLL3 ECD fragment proteins were then pooled and stored at −80 degrees Celsius (C).

Cynomolgus DLL3 ECD with Myc-tag on N-terminus and His-tag on C-terminus (SEQ ID NO: 8, hereinafter referred to as Myc-cynoDLL3-His) was expressed transiently using FreeStyle 293-F Cells (Thermo Fisher Scientific). Cultivation supernatant containing cynomolgus DLL3 ECD protein was applied to a HisTrap HP column (GE Healthcare) and eluted with imidazole. Fractions containing cynomolgus DLL3 ECD protein were collected and subsequently applied to a Superdex 200 gel filtration column (GE healthcare) equilibrated with 1×D-PBS. Fractions containing cynomolgus DLL3 ECD protein were then pooled and stored at −80 degrees C.

Example 2. Establishment of Ba/F3 Cell Line Expressing Human DLL3

Human DLL3 cDNA encoding delta-like protein 3 isoform 1 precursor (NCBI accession No. NP_058637.1 SEQ ID NO: 9) was inserted into the expression vector pCXND3 (described in WO2008/156083).

Linearized human DLL3-pCXND3 was introduced into mouse IL-3-dependent pro-B cell-derived cell line Ba/F3 by electroporation (LONZA, 4D-Nucleofector X).

After introduction, Geneticin was added, and the cells were cultured to obtain a cell line that was resistant to Geneticin. Transfected cells were plated in a 96-well plate by limiting dilution and were expanded. Established cell line was named hDLL3/BaF_H3.

Example 3: Generation and Screening of Anti-DLL3 Antibodies (Monospecific)

Anti-DLL3 antibodies were prepared, selected and assayed as described below.

Twelve week old NZW rabbits were immunized intradermally with human DLL3 ECD and cynomolgus DLL3 ECD proteins prepared as described in Example 1 alternately (50-100 micrograms (micro g)/dose/rabbit). Six days after the final immunization, the spleen and blood were collected from the immunized rabbits. Antigen-specific B-cells were stained with Myc-cynoDLL3-His and Anti-c-myc-FITC (Miltenyi Biotech), sorted with FCM cell sorter (FACS aria III, BD), and plated in 96-well plates at a density of one cell per well together with 25,000 cells/well of EL4 cells (European Collection of Cell Cultures) and activated rabbit T-cell conditioned medium diluted 20 times, and were cultured for 7-12 days. EL4 cells were treated with mitomycin C (Sigma, Cat No. M4287) for 2 hours and washed 3 times in advance. The activated rabbit T-cell conditioned medium was prepared by culturing rabbit thymocytes in RPMI-1640 containing Phytohemagglutinin-M (Roche, Cat No. 1 1082132-001), phorbol 12-myristate 13-acetate (Sigma, Cat No. P1585) and 2% FBS. After cultivation, B-cell culture supernatants were collected for further analysis and pellets were cryopreserved.

ELISA screening was conducted to test specificity of antibodies in B-cell culture supernatants. Human DLL3 expressing Ba/F3 (hDLL3/BaF_H3 established in Example 2, $2.5\times10^4$ cells) were immobilized onto a Nunc MaxiSorp 384-well plate (Sigma-Aldrich) which was pre-coated with BSA (Sigma-Aldrich) and SUNBRIGHT (registered trademark) OE-080CS as Biocompatible Anchor for cell Membrane (YUKA SANGYO). Immobilized cells were incubated with 20 microliters (micro L) of B-cell culture supernatants for 1 hour. The supernatants were aspirated and the cells were washed with HEPES buffer (0.02 M HEPES, 5 mM KCl, 4 mM $NaHCO_3$, 138 mM NaCl, 2 mM $CaCl_2$, 5 mM Glucose, 0.4 mM $KH_2PO_4$, 0.34 mM $Na_2HPO_4$° and 0.1% BSA). After washing, goat anti-rabbit IgG polyclonal antibody HRP conjugate (BETHYL, A120-111P) was added. The cells were further incubated on ice for 1 hour and washed. Then, ABTS Microwell Peroxidase Substrate (Kirkegaard & Perry Laboratories) was added and OD405 was analyzed with SPECTRAMax 384 (Molecular Devices).

A total of 28,864 B-cell clones were screened for binding to human DLL3 expressing Ba/F3, and 846 clones were selected as DLL3-specific binders which bind to hDLL3/BaF_H3. The selected clones were designated as DLA0001 to DLA0846. RNAs of DLA0001 to DLA0846 were purified from cryopreserved cell pellets by using ZR-96 Quick-RNA kits (ZYMO RESEARCH, Cat No. R1053). The DNAs of the antibody heavy chain variable regions were amplified by reverse transcription PCR and ligated with DNA encoding a human IgG1 heavy chain constant region, to form corresponding heavy chains. The DNAs of the antibody light chain variable regions were amplified by reverse transcription PCR and ligated with DNA encoding hkOMC light chain constant region (the amino acid sequence is shown in SEQ ID NO: 10), to form corresponding light chains. Cloned antibodies were expressed in FreeStyle 293-F Cells (Thermo Fisher Scientific) and purified from culture supernatants for functional evaluation. Several anti-DLL3 antibodies listed in Table 3 were selected for further analysis.

The DNA of anti-DLL3 antibody (DLA0316) heavy chain variable regions was also ligated with DNA encoding rabbit IgG heavy chain constant region, and the DNA of anti-DLL3 antibody (DLA0316) light chain variable regions was ligated with DNA encoding rabbit kappa chain constant region. This antibody was transiently expressed in FreeStyle 293-F Cells (Thermo Fisher Scientific), and named DLA0316-rbIgG.

Table 3 shows SEQ ID NOs of the variable regions of selected anti-DLL3 antibodies.

TABLE 3

| Antibody | Variable region | |
|---|---|---|
| name | Heavy chain | Light chain |
| DLA0106 | 11 | 12 |
| DLA0126 | 13 | 14 |
| DLA0316 | 15 | 16 |
| DLA0379 | 17 | 18 |
| DLA0580 | 19 | 20 |
| DLA0641 | 21 | 22 |
| DLA0769 | 23 | 24 |
| DLA0841 | 25 | 26 |

Example 4. Epitope Mapping of Selected Anti-DLL3 Antibodies (Monospecific)

The schematic structures of the full-length DLL3 protein and human DLL3 ECD fragment proteins prepared in Example 1 are shown in FIG. 1. The human DLL3 ECD fragment proteins prepared in Example 1 were used for epitope mapping of anti-DLL3 antibodies.

Nunc MaxiSorp 384-well plates (Sigma-Aldrich) were coated with each of the human DLL3 ECD fragment proteins del0 to del6, and blocked with 20% Blocking One (NACALAI TESQUE). Blocking buffer was removed and recombinant anti-DLL3 antibodies were incubated with the immobilized proteins for 1 hour at room temperature and washed with HEPES buffer (0.05% Tween20, HEPES). Monoclonal ANTI-FLAG M2-Peroxidase, Clone M2 (Sigma-Aldrich) was then added and incubated for 1 hour at room temperature and washed. Then, ABTS Microwell Peroxidase Substrate (Kirkegaard & Perry Laboratories) was added and OD405 was analyzed with SPECTRAMax 384 (Molecular Devices).

Figure 2:
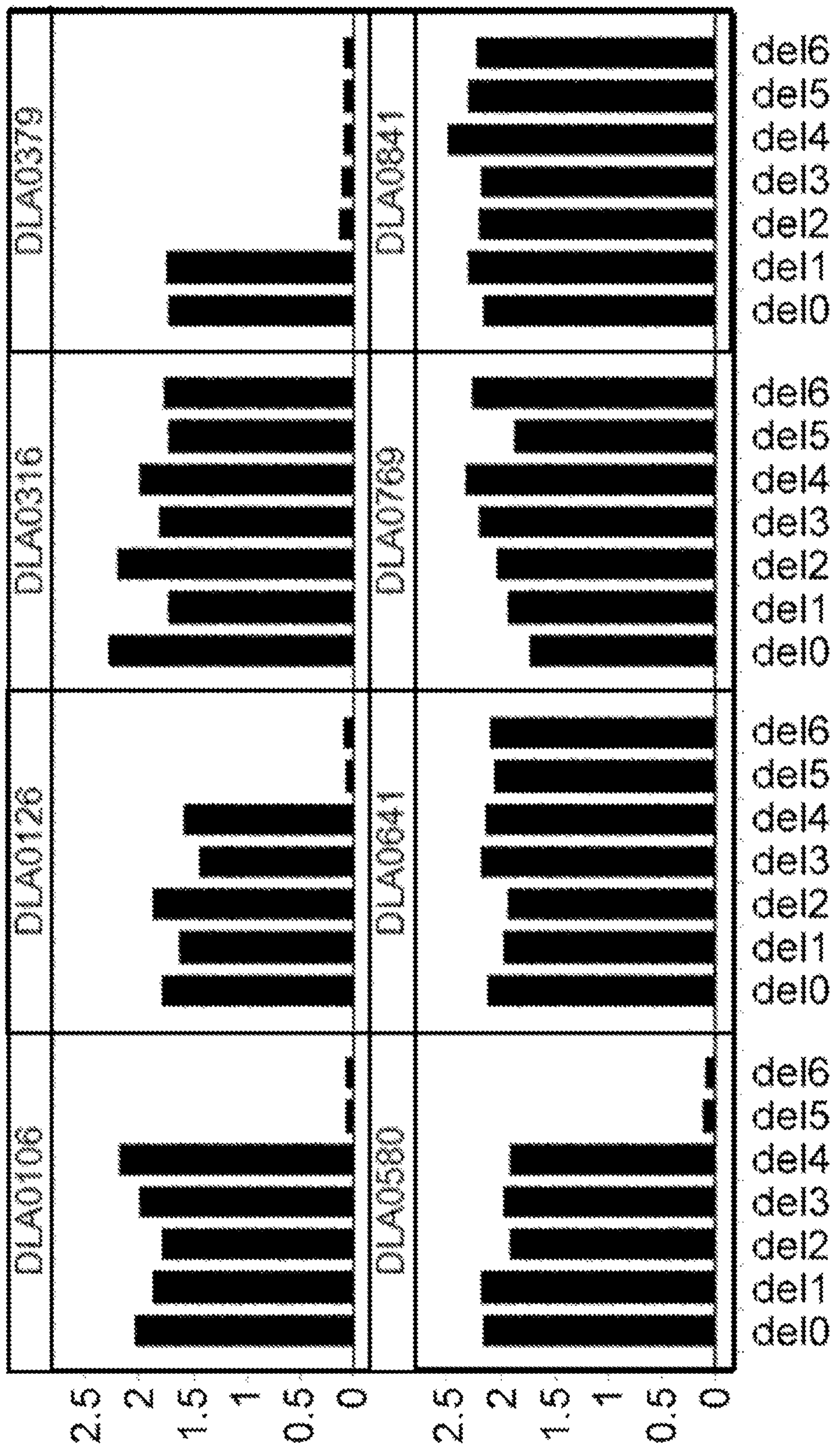
FIG. 2 shows the binding of the antibodies to the human DLL3 ECD fragment proteins. Names of the tested anti-DLL3 antibodies are shown on the top of each graph.

FIG. 2 shows the binding for the human DLL3 ECD fragment proteins. Each bar (OD405 value) represents the reactivity of the tested antibody against each of the human DLL3 ECD fragment proteins. Antibody epitopes can be inferred by testing which domain deletion abrogates antibody binding, and the epitope of each antibody is shown in FIG. 1.

Example 5: Generation and Functional Evaluation of Anti-DLL3/CD3 Bispecific Antibodies Example 5.1. Evaluation of DLL3 Expression on Cancer Cell Surface Expression of DLL3 on the cell surface of cultured cancer cell lines SK-MEL 30 (DSMZ), NCI-H1436 (ATCC), and NCI-H2227 (ATCC) was evaluated by flow cytometry.

Figure 3:
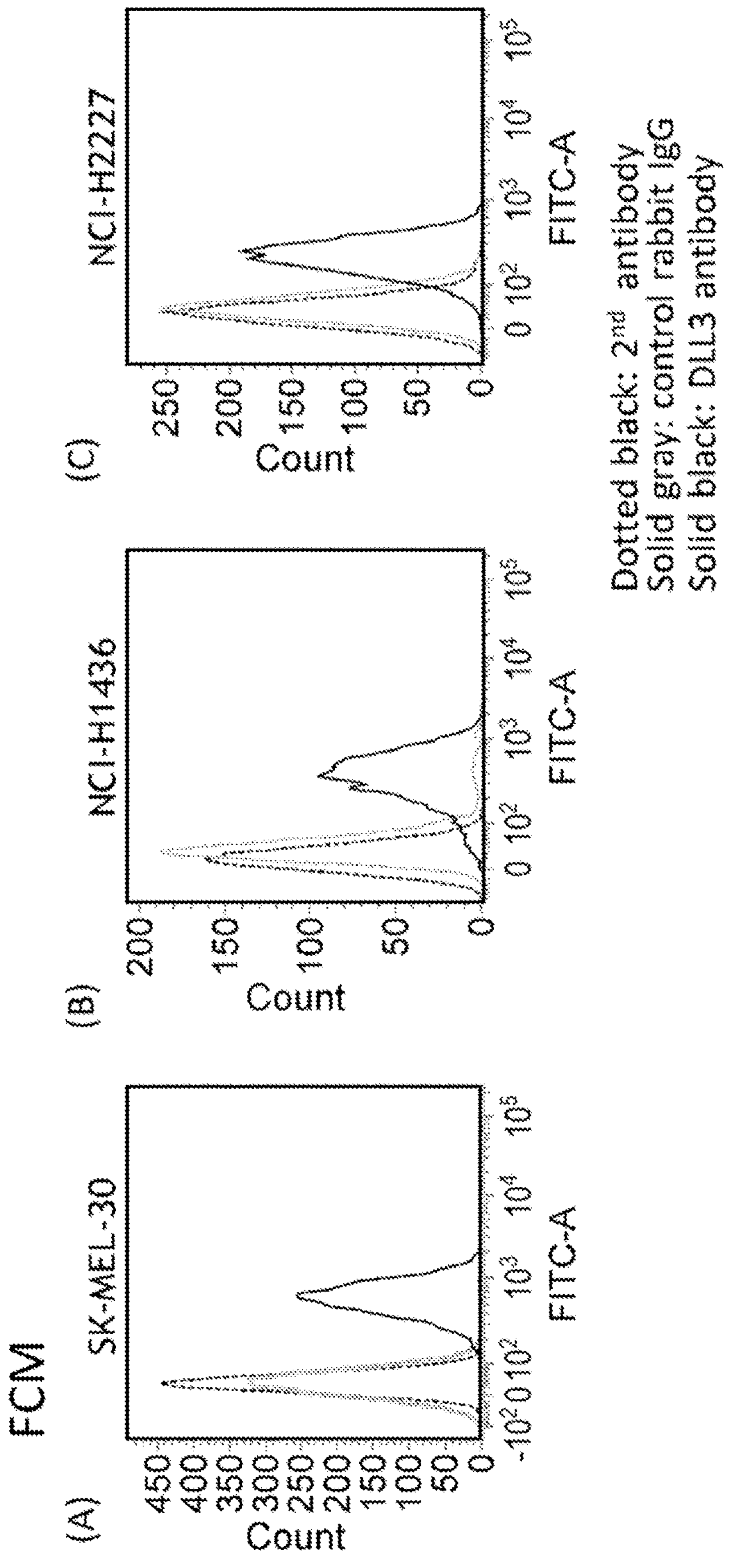
FIG. 3 shows DLL3 expression in SK-MEL-30 (A), NCI-H1436 (B) and NCI-H2227 (C) cancer cell lines. Dotted black line: 2nd antibody (BECKMAN COULTER) only, solid gray line: control rabbit IgG (CELL LAB), solid black line: DLL3 antibody (bivalent DLA0316).

The cancer cells ($5\times10^5$ cells) were washed with 0.5% BSA-supplemented CellWASH (BD Bioscience) (hereinafter referred to as FACS/PBS). Bivalent anti-DLL3 antibody (DLA0316-rbIgG) or the control antibody (rabbit IgG) was added at a final concentration of 20 micro g/mL in a 50 micro L solution. After being left to stand at 4 degrees C. for 30 to 60 minutes, the cells were washed with FACS/PBS, and an FITC-labeled goat anti-rabbit IgG antibody diluted 50-fold with FACS/PBS was added to the cells. After being left to stand at 4 degrees C. for further 30 minutes, the cells were washed with FACS/PBS, and analyzed by FACS Verse (Becton Dickinson). DLL3 was found to be expressed on each of the cancer cell lines (FIG. 3).

Example 5.2 Functional Characterization of Anti-DLL3/CD3 Bispecific Antibodies

Example 5.2.1 Preparation of Human Peripheral Blood Mononuclear Cells (PBMC) Solution Primary human PBMC solutions were freshly isolated from healthy volunteers.

For fresh PBMC solutions, 50 mL of peripheral blood was collected from each healthy volunteer (individual adult) using a syringe preloaded with 100 micro L of 1,000 units/mL heparin solution (Novo Heparin for injection, 5,000 units, Novo Nordisk). This peripheral blood was diluted two-fold in PBS (−), divided into four aliquots, and added to a Leucosep tube for lymphocyte separation (Cat. No. 227290, Greiner Bio-One) that had been loaded with 15 mL of Ficoll-Paque PLUS and subjected to centrifugation in advance. This separation tube was centrifuged (at 2,150 rpm for ten minutes at room temperature), and the mononuclear cell fraction was collected. The cells in the mononuclear cell fraction were washed once with Dulbecco's Modified Eagle's Medium containing 10% FBS (SIGMA) and adjusted to the cell density of $4\times10^6$ cells/mL using 10% FBS/RPMI1640. This cell suspension was used as the human PBMC solution in the experiments below.

Example 5.2.2 Measurement of T Cell-Dependent Cell Cytotoxicity (TDCC) of Anti-DLL3/CD3 Bispecific Antibodies by the Rate of Cell Growth Inhibition Some anti-DLL3 monospecific antibodies described in Table 3 and some anti-DLL3 antibodies described in WO2011/093097A1, together with an anti-CD3 antibody (variable region of heavy chain SEQ ID NO: 57, variable region of light chain SEQ ID NO: 58) were used to generate anti-DLL3/CD3 bispecific antibodies using conventional methods published elsewhere. The CDR sequences of the DLL3-binding arm in the anti-DLL3/CD3 bispecific antibodies are shown in Table 4.

Each of the generated bispecific antibodies contained an Fc region with attenuated affinity for the Fc gamma receptor.

Table 4 shows SEQ ID NOs of HVR (CDR) sequences of the DLL3-binding arm in anti-DLL3/CD3 bispecific antibodies.

TABLE 4

| | Hyper variable region (HVR) sequences of anti-DLL3 arm | | | | | |
|---|---|---|---|---|---|---|
| Antibody name | HCDR1 | HCDR2 | HCDR3 | LCDR1 | LCDR2 | LCDR3 |
| DLA0316/No.12 | 27 | 28 | 29 | 30 | 31 | 32 |
| DLA0841/No.12 | 33 | 34 | 35 | 36 | 37 | 38 |
| DLA0580/No.12 | 39 | 40 | 41 | 42 | 43 | 44 |
| DLA0769/No.12 | 45 | 46 | 47 | 48 | 49 | 50 |
| DL312/No.12 | 51 | 52 | 53 | 54 | 55 | 56 |

"HCDR1", "HCDR2", "HCDR3", LCDR1", "LCDR2", and "LCDR3" in Table 4 correspond to HVR-H1, HVR-H2, HVR-H3, HVR-L1, HVR-L2, and HVR-L3, respectively.

Figure 4:
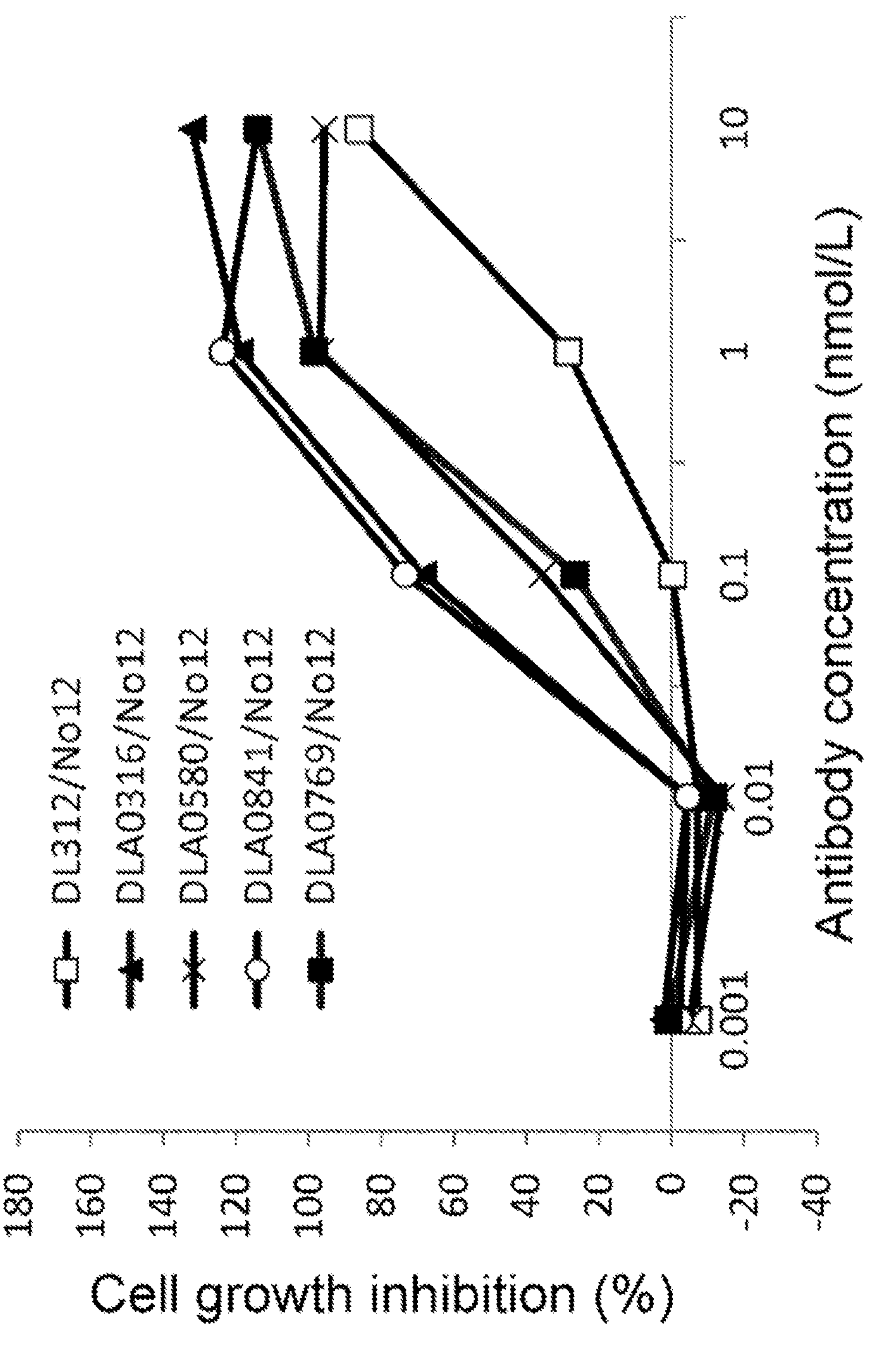
FIG. 4 shows T cell-dependent cellular cytotoxicity (TDCC) of anti-DLL3/CD3 bispecific antibodies (DL312/No.12, DLA0316/No.12, DLA0580/No.12, DLA0814/No.12, and DLA0769/No.12) against SK-MEL-30 cell lines.

FIG. 4 shows the T cell-dependent cellular cytotoxicity (TDCC) of the generated anti-DLL3/CD3 bispecific antibodies. Cytotoxic activity was assessed by the rate of cell growth inhibition using xCELLigence Real-Time Cell Analyzer (Roche Diagnostics). The SK-MEL 30 human cancer cell line was used as target cells. Target cells were detached from the dish and plated onto E-plate 96 (Roche Diagnostics) in aliquots of 100 micro L/well by adjusting the cells to $1\times10^4$ cells/well, and the measurement of the cell growth was initiated using xCELLigence Real-Time Cell Analyzer. 24 hours later, the plate was removed and a 50 micro L aliquot of the respective antibodies prepared at each concentration (0.001, 0.01, 0.1, 1 or 10 nmol/L) was added to the plate. After 15 minutes of reaction at room temperature, 50 micro L of the fresh human PBMC solution prepared in Example 5.2.1 was added at an effector (PBMC)/target (SK-MEL 30) ratio of 2 (i.e., $2\times10^4$ cells/well), and the measurement of the cell growth was resumed using xCELLigence Real-Time Cell Analyzer. The reaction was carried out under the conditions of 5% carbon dioxide gas at 37 degrees C. 38 hours after the addition of PBMCs, the Cell Growth Inhibition (CGI) rate (%) was determined using the equation below. The Cell Index value obtained from xCELLigence Real-Time Cell Analyzer used in the calculation was a normalized value where the Cell Index value at the time point immediately before antibody addition was defined as 1.

$$\text{Cell Growth Inhibition rate (\%)}=(A-B)\times100/(A-1)$$

A represents the mean Cell Index value in wells without antibody addition (containing only target cells and human PBMCs), and B represents the mean Cell Index value of target wells containing one of the generated anti-DLL3/CD3 bispecific antibodies. The examinations were performed in triplicates.

All antibodies analyzed were subjected to TDCC assay using the SK-MEL-30 cell line. All the bispecific antibodies showed cell growth inhibition in a dose dependent manner, and the cell growth inhibition rates were over 80% at an antibody concentration of 10 nmol/L. The bispecific antibodies DLA0316/No.12 and DLA0841/No.12 showed the strongest TDCC activity (FIG. 4).

Example 5.2.3 Measurement of TDCC of Chimeric Anti-DLL3/CD3 Bispecific Antibodies by Calcein Release Assay in SCLCs TDCC of anti-DLL3/CD3 bispecific antibodies against small cell lung cancer cell lines was also analyzed. Cytotoxic activity was assessed by the calcein-acetoxymethyl release assay. The NCI-H1436 and NCI-H2227 human cancer cell lines were used as target cells. The assay was conducted in triplicate. The target cells were labeled with calcein-acetoxymethyl (Calcein-AM; Nacalai tesque) for 2 h at 37 degrees C. and then were washed. The anti-DLL3/CD3 bispecific antibodies prepared at each final concentration (0.001, 0.01, 0.1, 1 or 10 nM) were pipetted into a 96-well U-bottomed plate and, calcein-labeled target cell suspensions ($2\times10^5$ cells/mL) was added to each well. After leaving the plates for 15 minutes at room temperature, the effector cell (PBMC) suspension ($5\times10^6$ cells/mL) was added to the wells. After the 96-well plate was stirred, the plate was centrifuged at 1000 rpm for 2 minutes, and incubated in a 5% $CO_2$ incubator at 37 degrees C. for approximately 4 hours. After the 96-well plate was stirred well, and centrifuged at 1000 rpm for 5 minutes, a 100 micro L aliquot of culture medium from each well was transferred to a 96-well flat bottomed plate. Absorbance (495 nm, reference 515 nm) was measured with EnSpire (PerkinElmer). For maximal release, the cells were lysed with 0.5% NP-40. The fluorescence value of the culture medium background was subtracted from the value of the experimental release (A), the target cell spontaneous release (B), and the target cell maximal release (C). The cytotoxicity was calculated using the following formula:

$$\text{Cytotoxicity}(\%)=(A-B)/(C-B)\times100$$

Figure 5:
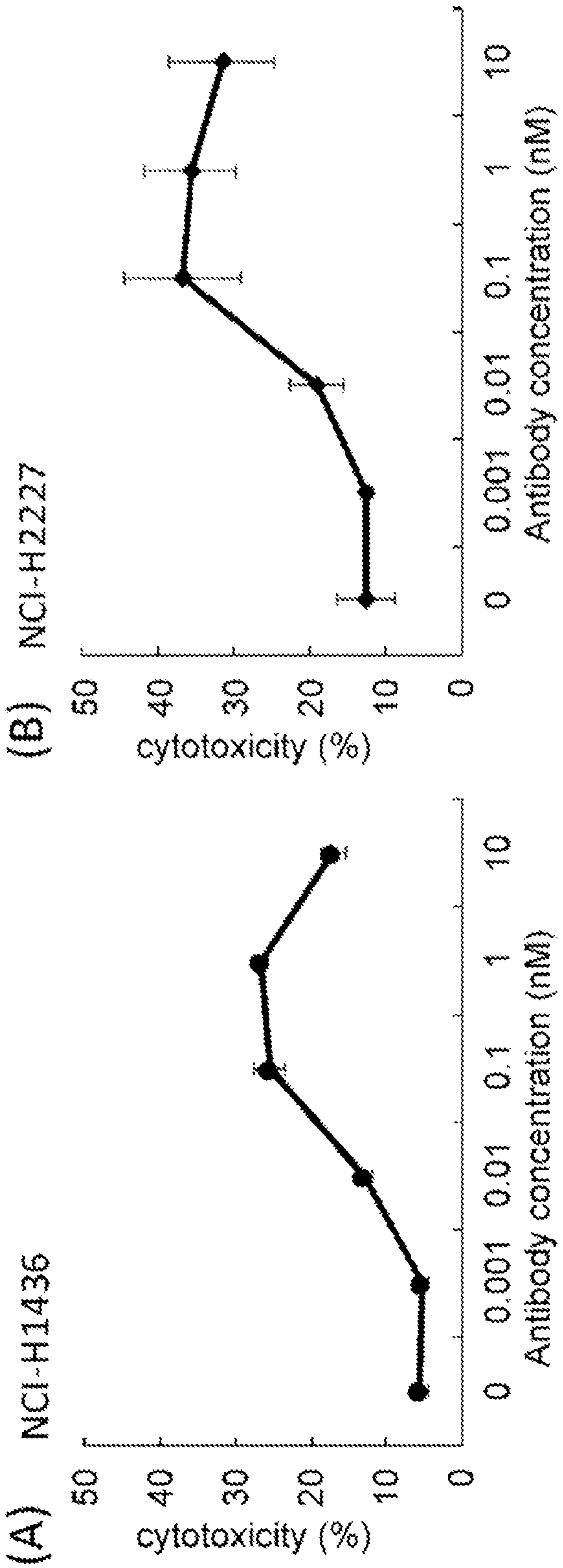
FIG. 5 shows TDCC of anti-DLL3/CD3 bispecific antibodies (DLA0316/No.12) evaluated by calcein release assay against NCI-H1436 (A) and NCI-H2227 (B) SCLC cell lines.

FIG. 5 shows the TDCC of anti-DLL3/CD3 bispecific antibodies against small cell lung cancer cell lines. DLA0316/No.12 showed cytotoxicity in a dose dependent manner against both of the two small cell lung cancer cell lines.

Example 6. Evaluation of the In Vivo Anti-Tumor Efficacy

Some of the above-described antibodies were evaluated for their in vivo efficacy using tumor-bearing models.

Evaluation of the in vivo anti-tumor efficacy was carried out using the anti-human DLL3/CD3 bispecific antibodies (DLA0316/No.12, DLA0841/No.12, and DLA0580/No.12) which were confirmed to have cytotoxic activities in the in vitro assay described in Example 5. Cancer cell lines were transplanted into NOD scid mice, and the NOD scid mice with confirmed tumor formation were subjected to transplantation of T cells grown by in vitro culturing of human PBMCs. The mice (referred to as T cell-injected model) were treated by administration of the anti-human DLL3/CD3 bispecific antibodies.

More specifically, in anti-tumor efficacy tests of the anti-human DLL3/CD3 bispecific antibodies using the SK-MEL-30 (ATCC)-transplanted T cell-injected model, the tests below were performed. T cells were expansively cultured using purchased PBMCs and a T cell activation/expansion kit/human (MACS Miltenyi biotec). The human cancer cell line SK-MEL-30 ($1\times10^7$ cells) was mixed with Matrigel™ Basement Membrane Matrix (BD), and transplanted to the inguinal subcutaneous region of NOD scid mice (CLEA Japan, female, 6 W to 8 W). The day of transplantation was defined as day 0. On the day before transplantation (day 0), the anti-asialo-GM1 antibody (Wako Pure Chemicals) was administered intraperitoneally to the mice at 0.2 mg/mouse. On day 10 after the transplantation, the mice were separated into groups according to their body weight and tumor size, and the anti-asialo-GM1 antibody was administered again intraperitoneally to the mice at 0.2 mg/mouse. On the following day, T cells obtained by the aforementioned expansive culturing were transplanted intraperitoneally at $3\times10^7$ cells/mouse. Four hours after T cell transplantation, the anti-human DLL3/CD3 bispecific antibodies were administered intravenously through the caudate vein at 5 mg/kg and 1 mg/kg. The anti-human DLL3/CD3 bispecific antibodies were administered only once.

Figure 6:
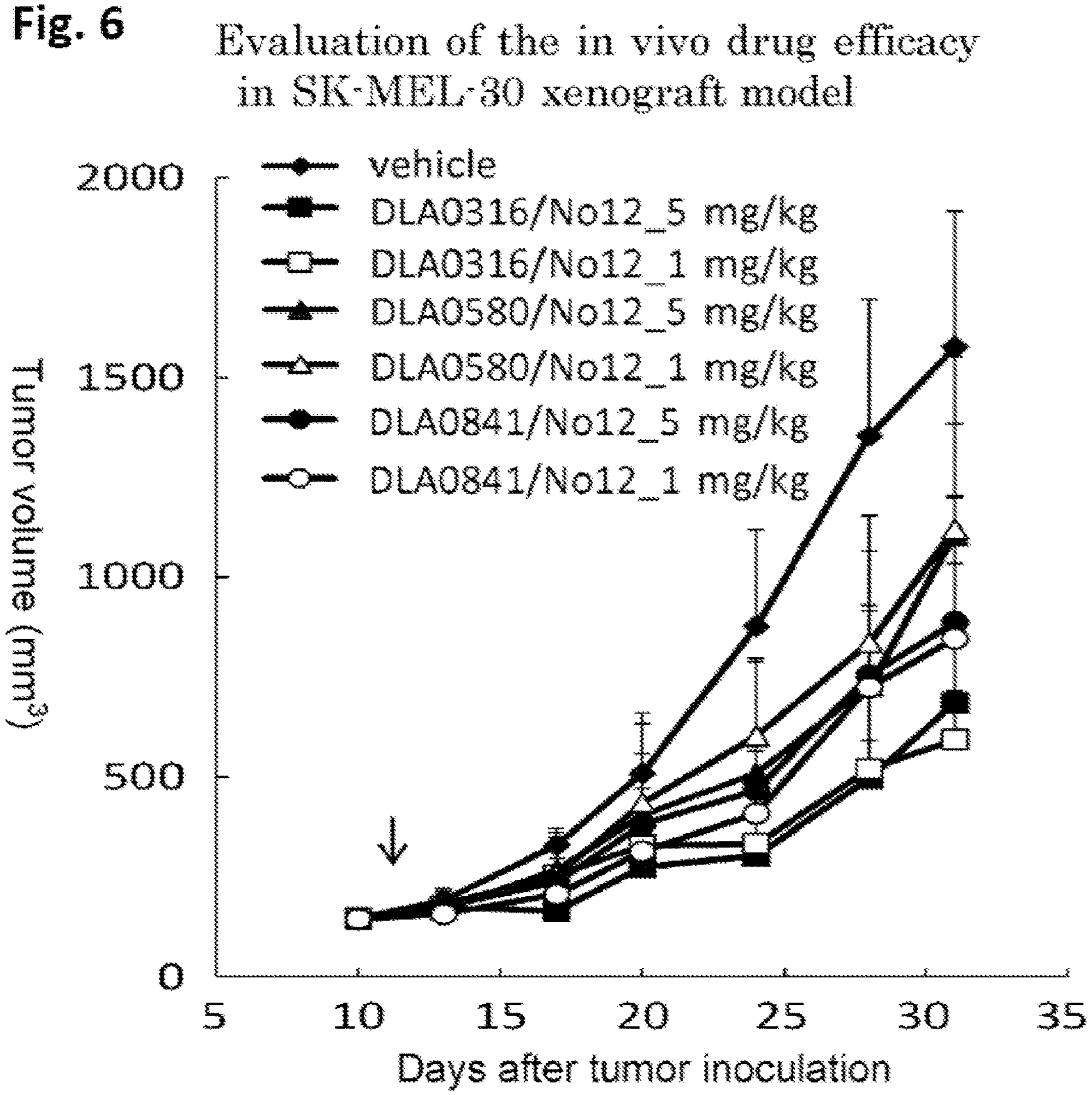
FIG. 6 shows in vivo anti-tumor efficacy of anti-DLL3/CD3 bispecific antibodies (DLA0316/No.12, DLA0580/No.12 and DLA0841/No.12) in an SK-MEL-30 tumor-bearing T-cell injection model. The antibody used and its dose are also shown.

Anti-tumor activities (inhibition of tumor volume increase) were observed in the anti-human DLL3/CD3 bispecific antibody-administered group compared to the solvent-administered control group (FIG. 6).

The anti-tumor efficacy tests for DLA0316/No.12 on the NCI-H1436-transplanted T cell-injected model were performed by similar methods. On day 16 after the tumor transplantation, the mice were separated into groups and T cells were transplanted on the following day. Three days after T cell transplantation, the anti-DLL3/CD3 bispecific antibodies were administered intravenously at 5 mg/kg, 1 mg/kg, and 0.2 mg/kg.

Figure 7:
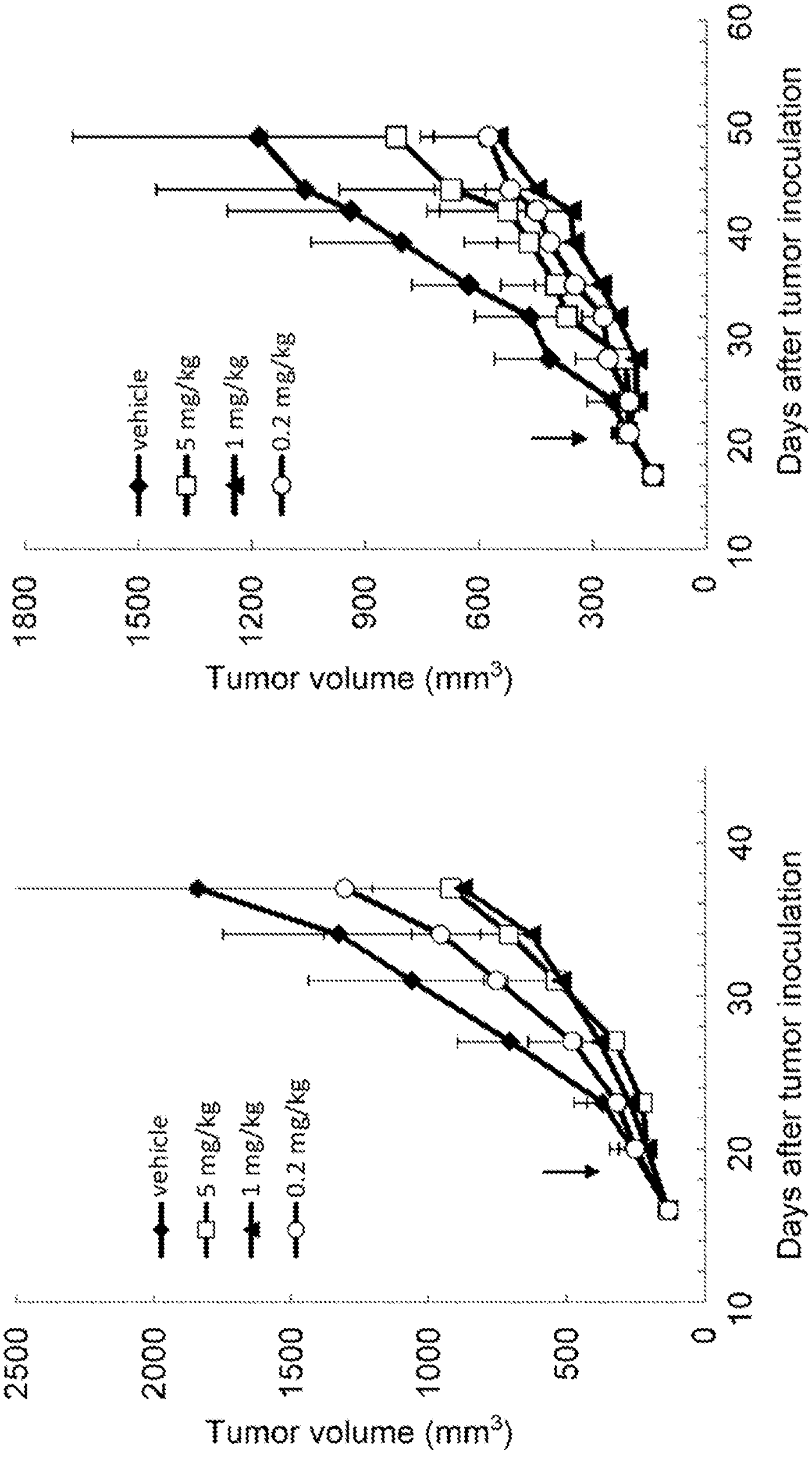
FIG. 7 shows in vivo anti-tumor efficacy of anti-DLL3/CD3 bispecific antibody (DLA0316/No.12) in an SCLC tumor-bearing T-cell injection model. The cancer cell lines used were NCI-H1436 (A) and NCI-H2227 (B).

Anti-tumor activities (inhibition of tumor volume increase) were observed in the DLA0316/No.12-administered group compared to the solvent-administered control group (FIG. 7A).

The anti-tumor efficacy tests for DLA0316/No.12 on the NCI-H2227-transplanted T cell-injected model were performed by similar methods. On day 18 after the tumor transplantation, the mice were separated into groups and T cells were transplanted on day 17. Three days after T cell transplantation, the anti-DLL3/CD3 bispecific antibodies were administered intravenously at 5 mg/kg, 1 mg/kg, and 0.2 mg/kg.

Anti-tumor activities (inhibition of tumor volume increase) were observed in the DLA0316/No.12-administered group compared to the solvent-administered control group (FIG. 7B).

Example 7. Humanization and Optimization of Anti-DLL3 Monospecific Antibodies Variable regions of the heavy and light chains of humanized DLL3 antibodies were designed using human germline frameworks. The polynucleotides of the designed heavy and light chain variable regions were cloned into expression vectors containing the heavy chain constant region SG1 sequence (SEQ ID NO: 59 (the amino acid sequence is shown in SEQ ID NO: 60)) and the light chain constant region SK1 sequence (SEQ ID NO: 61 (the amino acid sequence is shown in SEQ ID NO: 62)), respectively. Humanized antibodies were transiently expressed in Free-Style 293-F Cells (Thermo Fisher Scientific), and BIAcore analysis was carried out as described above. The sequences of humanized antibodies and their parental antibodies are shown in Table 5 below.

Selected humanized antibodies were further optimized. To avoid chemical degradations such as deamidation, isomerization, succinimide formation, methionine and tryptophan oxidation and cysteinylation of unpaired cysteine in CDR regions, amino acid residues within the sequences of the selected humanized antibodies were mutated to 18 other amino acids, excluding the original amino acid and Cysteine. The variants were transiently expressed and purified by the method described above. Purified variant monoclonal antibodies were assessed by BIAcore using the method described above, and variants of interest which could bind to human DLL3 and cynomolgus DLL3 as the parent antibody were selected. Antibodies with a combination of these mutations in the CDRs were then generated. The HVR (CDR) sequences of the antibodies containing these various mutations are shown in Table 6 below with the HVR (CDR) sequences of the parental antibodies.

Table 5 shows SEQ ID NOs of the generated anti-DLL3 antibodies.

TABLE 5

| | Variable region | | Constant region | |
|---|---|---|---|---|
| Antibody name | Heavy chain | Light chain | Heavy chain | Light chain |
| DLA0316-SG1 | 15 | 16 | 60 | 10 |
| D30316AE01-SG1 | 63 | 72 | 60 | 62 |
| D30316AE02-SG1 | 64 | 72 | 60 | 62 |
| D30316AE03-SG1 | 65 | 72 | 60 | 62 |
| DLA0841-SG1 | 25 | 26 | 60 | 10 |
| D30841AE05-SG1 | 66 | 73 | 60 | 62 |
| D30841AE08-SG1 | 67 | 73 | 60 | 62 |
| D30841AE11-SG1 | 67 | 74 | 60 | 62 |
| D30841AE12-SG1 | 68 | 73 | 60 | 62 |
| D30841AE13-SG1 | 69 | 73 | 60 | 62 |
| D30841AE14-SG1 | 70 | 73 | 60 | 62 |
| D30841AE15-SG1 | 71 | 73 | 60 | 62 |

Table 6 shows SEQ ID NOs of the HVR (CDR) sequences of the generated anti-DLL antibodies.

TABLE 6

| | Hyper variable region (HVR) | | | | | |
|---|---|---|---|---|---|---|
| Antibody name | HCDR1 | HCDR2 | HCDR3 | LCDR1 | LCDR2 | LCDR3 |
| DLA0316-SG1 | 27 | 28 | 29 | 30 | 31 | 32 |
| D30316AE01-SG1 | 27 | 28 | 29 | 30 | 31 | 32 |
| D30316AE02-SG1 | 27 | 75 | 29 | 30 | 31 | 32 |
| D30316AE03-SG1 | 27 | 76 | 29 | 30 | 31 | 32 |
| DLA0841-SG1 | 33 | 34 | 35 | 36 | 37 | 38 |
| D30841AE05-SG1 | 77 | 78 | 79 | 36 | 37 | 38 |
| D30841AE08-SG1 | 77 | 78 | 80 | 36 | 37 | 38 |
| D30841AE11-SG1 | 77 | 78 | 80 | 36 | 37 | 81 |
| D30841AE12-SG1 | 77 | 78 | 80 | 36 | 37 | 38 |
| D30841AE13-SG1 | 77 | 78 | 80 | 36 | 37 | 38 |
| D30841AE14-SG1 | 77 | 78 | 80 | 36 | 37 | 38 |
| D30841AE15-SG1 | 77 | 78 | 80 | 36 | 37 | 38 |

"HCDR1", "HCDR2", "HCDR3", LCDR1", "LCDR2", and "LCDR3" in Table 6 correspond to HVR-H1, HVR-H2, HVR-H3, HVR-L1, HVR-L2, and HVR-L3, respectively.

Example 8 Competition Analysis of Anti-DLL3 Antibodies

Preparation of Biotin-Labelled Anti-DLL3 Antibodies

Anti-DLL3 antibodies (DL301-SG1, DL306-SG1, DL309-SG1, DL312-SG1, DLL3-14-SG1, DLL3-22-SG1, DLL3-4-SG1 and DLL3-6-SG1) which comprises variable regions of previously reported anti-DLL3 antibodies, were prepared in the same manner as described above. Variable heavy and light chain sequences (VH and VL) were cloned into expression vectors with SG1 (SEQ ID NO: 60) and with SK1 (SEQ ID NO: 62), respectively. The sequences of the anti-DLL3 antibodies are shown in Table 7 below.

Table 7 shows SEQ ID NOs of prepared anti-DLL3 antibodies.

TABLE 7

| | Variable region | | Constant region | |
|---|---|---|---|---|
| Antibody name | Heavy chain | Light chain | Heavy chain | Light chain |
| DL301-SG1 | 82 | 90 | 60 | 62 |
| DL306-SG1 | 83 | 91 | 60 | 62 |
| DL309-SG1 | 84 | 92 | 60 | 62 |
| DL312-SG1 | 85 | 93 | 60 | 62 |
| DLL3-14-SG1 | 86 | 94 | 60 | 62 |
| DLL3-22-SG1 | 87 | 95 | 60 | 62 |
| DLL3-4-SG1 | 88 | 96 | 60 | 62 |
| DLL3-6-SG1 | 89 | 97 | 60 | 62 |

Anti-DLL3 antibodies (DL301-SG1, DL306-SG1, DL309-SG1, DL312-SG1, D30316AE02-SG1, and D30841AE05-SG1) were labelled with NHS-PEG4-Biotin (Thermo Fisher), thereby preparing biotin-labelled anti-DLL3 antibodies.

Octet Assay

Octet (registered trademark) RED384 (Fortebio) was used to perform competitive binding assays by epitope binning for a panel of antibodies. A biotinylated antibody (DL301-SG1, DL306-SG1, DL309-SG1, DL312-SG1, D30316AE02-SG1, and D30841AE05-SG1) at 40 nM was first loaded to a streptavidin (SA) biosensor. Next, the sensor is exposed to 20 nM of human DLL3, followed by exposure to 80 nM of second antibody. The second antibodies are DL301-SG1, DL306-SG1, DL309-SG1, DL312-SG1, D30316AE02-SG1, D30841AE05-SG1, DLL3-14-SG1, DLL3-22-SG1, DLL3-4-SG1 and DLL3-6-SG1. Raw data was processed using ForteBio's Data Analysis Software 7.0 and the antibody pairs were assessed for competitive binding. Additional binding by the second antibody indicates an unoccupied epitope (non-competitor), while no binding indicates epitope blocking (competitor).

To determine if there is a competitive antibody binding, antibody A was first immobilized to streptavidin biosensor and the sequential binding of the complex of antigen with antibody B was measured.

The competition ratio of antibody B to antibody A was calculated using the following equation: Competition Ratio (Antibody B to Antibody A)=[Binding Response (Antibody B-Antigen)]/[Binding Response (Antigen-Antibody A)]

The results revealed that D30841AE05-SG1 competes with DL306-SG1, and D30316AE02-SG1 does not compete with other antibodies tested (FIG. 8).

Example 9 Preparation of an Anti-Human DLL3/Anti-Human CD3 Bispecific Antibody

The anti-DLL3 monospecific antibodies described in Table 5 and an anti-CD3 antibody were used to generate anti-DLL3/CD3 bispecific antibodies using conventional methods published elsewhere. The combination of anti-DLL3 arm and anti-CD3 arm are shown in Table 8.

The bispecific antibodies generated contain a silent Fc with attenuated affinity for the Fc gamma receptor. For these molecules, the Fab arm exchange technique reported by Igawa et al. (WO 2016159213) was used to make the bispecific antibodies.

Table 8 shows SEQ ID NOs of the variable regions of the prepared anti-DLL3/CD3 bispecific antibodies.

TABLE 8

| | anti-DLL3 arm | | anti-CD3 arm | |
|---|---|---|---|---|
| Antibody name | Heavy chain variable region | Light chain variable region | Heavy chain variable region | Light chain variable region |
| DLA0316/TR01 | 15 | 16 | 98 | 103 |
| DLA0316/AN104 | 15 | 16 | 99 | 103 |
| DLA0316/AN119 | 15 | 16 | 100 | 103 |
| DLA0316/AN121 | 15 | 16 | 101 | 103 |
| DLA0316/AN395 | 15 | 16 | 102 | 103 |
| D30316AE03/TR01 | 65 | 72 | 98 | 103 |
| D30316AE03/AN104 | 65 | 72 | 99 | 103 |
| D30316AE03/AN119 | 65 | 72 | 100 | 103 |
| D30316AE03/AN121 | 65 | 72 | 101 | 103 |
| D30316AE03/AN395 | 65 | 72 | 102 | 103 |
| D30841AE08/TR01 | 67 | 73 | 98 | 103 |
| D30841AE11/TR01 | 67 | 74 | 98 | 103 |
| D30841AE08/AN121 | 67 | 73 | 101 | 103 |
| D30841AE11/AN121 | 67 | 74 | 101 | 103 |
| DLA0841/TR01 | 25 | 26 | 98 | 103 |
| DLA0841/AN121 | 25 | 26 | 101 | 103 |

Example 10 Biacore Analysis for Binding Affinity Evaluation of Anti-DLL3 Arm in the Anti-DLL3/CD3 Bispecific Antibodies Binding affinity of anti-DLL3 arm in the anti-DLL3/CD3 antibodies to human or cynomolgus DLL3 at pH 7.4 were assessed at 37 degrees C. using Biacore 8K instrument (GE Healthcare). Anti-human Fc (GE Healthcare) was immobilized onto all flow cells of a CM4 sensor chip using amine coupling kit (GE Healthcare). The bispecific antibodies were captured onto the anti-Fc sensor surfaces, and then recombinant human or cynomolgus DLL3 was injected over the flow cell. All antibodies and analytes were prepared in ACES pH 7.4 containing 20 mM ACES, 150 mM NaCl, 0.05% Tween 20, 0.005% $NaN_3$. Sensor surface was regenerated each cycle with 3M $MgCl_2$. Binding affinity were determined by processing and fitting the data to 1:1 binding model using Biacore 8K Evaluation software, version 2.0 (GE Healthcare).

The binding affinity of anti-DLL3 arm of the bispecific antibodies to recombinant DLL3 are shown in Table 9.

Table 9 shows binding affinity of anti-DLL3 arm of the bispecific antibodies.

TABLE 9

| | Human DLL3 | | | Cyno DLL3 | | |
|---|---|---|---|---|---|---|
| Ab name | ka ($M^{-1}s^{-1}$) | kd ($s^{-1}$) | KD (M) | ka ($M^{-1}s^{-1}$) | kd ($s^{-1}$) | KD (M) |
| DLA0316/TR01 | 2.47E+06 | 8.72E−05 | 3.53E−11 | 2.49E+06 | 4.96E−05 | 1.99E−11 |
| D30316AE03/TR01 | 2.34E+06 | 6.11E−05 | 2.61E−11 | 2.32E+06 | 2.72E−05 | 1.17E−11 |
| D30841AE08/TR01 | 2.47E+06 | 2.15E−04 | 8.72E−11 | 2.59E+06 | 1.91E−04 | 7.37E−11 |
| D30841AE11/TR01 | 1.88E+06 | 3.25E−04 | 1.72E−10 | 1.86E+06 | 2.65E−04 | 1.42E−10 |
| DLA0841/TR01 | 3.87E+06 | 2.47E−04 | 6.39E−11 | 3.83E+06 | 2.38E−04 | 6.21E−11 |

Example 11 Biacore Analysis for Binding Affinity Evaluation of Anti-CD3 Arm of the Anti-DLL3/CD3 Bispecific Antibodies Binding affinity of the anti-CD3 arm of the anti-DLL3/CD3 bispecific antibodies to CD3 at pH 7.4 was assessed at 37 degrees C. using Biacore 8K instrument (GE Healthcare). Anti-human Fc (GE Healthcare) was immobilized onto all flow cells of a CM4 sensor chip using amine coupling kit (GE Healthcare). The bispecific antibodies were captured onto the anti-Fc sensor surfaces, and then recombinant human CD3eg proteins (CD3 epsilon-gamma, heterodimer of CD3 epsilon and CD3 gamma) was injected over the flow cell. All antibodies and analytes were prepared in ACES pH 7.4 containing 20 mM ACES, 150 mM NaCl, 0.05% Tween 20, 0.005% $NaN_3$. Sensor surface was regenerated each cycle with 3M $MgCl_2$. Binding affinity were determined by processing and fitting the data to 1:1 binding model using Biacore 8K Evaluation software, version 2.0 (GE Healthcare).

The binding affinity of various anti-CD3 arms of bispecific antibodies to recombinant CD3eg proteins are shown in Table 10.

Table 10 shows binding affinity of the anti-CD3 arm of the bispecific antibodies.

TABLE 10

| Ab name | ka ($M^{-1}s^{-1}$) | kd ($s^{-1}$) | KD (M) |
|---|---|---|---|
| D30316AE03/TR01 | 1.34E+05 | 1.69E−02 | 1.27E−07 |
| D30316AE03/AN104 | 7.14E+04 | 2.66E−03 | 3.73E−08 |

TABLE 10-continued

| Ab name | ka ($M^{-1}s^{-1}$) | kd ($s^{-1}$) | KD (M) |
|---|---|---|---|
| D30316AE03/AN119 | 1.45E+05 | 1.60E−03 | 1.10E−08 |
| D30316AE03/AN121 | 9.86E+04 | 7.44E−04 | 7.55E−09 |
| D30316AE03/AN395 | 2.42E+05 | 7.43E−03 | 3.07E−08 |

Figure 9:
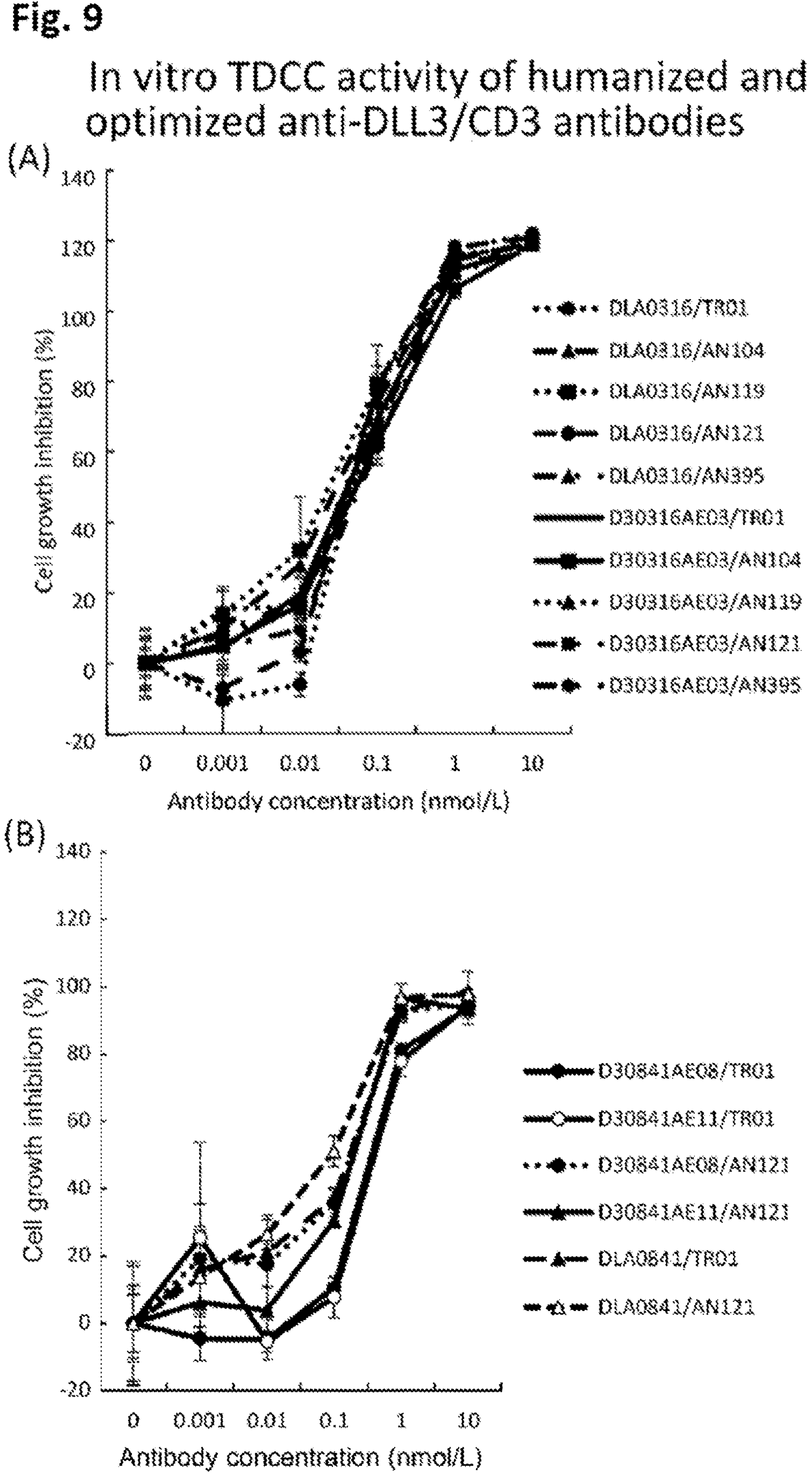
FIG. 9 shows TDCC of humanized anti-DLL3/CD3 bispecific antibodies against SK-MEL-30 cell lines. The anti-DLL3 arms of the tested bispecific antibodies were derived from DLA0136 or its humanized variant D30316AE03 (A), and DLA0841 or its humanized variants D30841AE08 and D30841AE11 (B), respectively.

Example 12. Measurement of T Cell-Dependent Cell Cytotoxicity (TDCC) of Humanized Anti-DLL3/CD3 Bispecific Antibodies by the Rate of Cell Growth Inhibition The TDCC assay for the humanized anti-DLL3/CD3 bispecific antibodies was performed by methods similar to those described in Example 5.2.2. The SK-MEL 30 human cancer cell line was used as target cells and the assay time was for 48 or 72 hours. FIG. 9 shows the TDCC of humanized anti-DLL3/CD3 bispecific antibodies. Humanized antibodies showed the same level of TDCC activity compared with its parent clone, concluded as sufficient efficacy.

Example 13. Preparation of an Anti-Human DLL3/Anti-human CD3 Bispecific Antibody The anti-DLL3 monospecific antibody D30841AE13-SG1 described in Table 5 and anti-CD3 antibodies were used to generate anti-DLL3/CD3 bispecific antibodies using conventional methods published elsewhere. The SEQ ID NOs are shown in Table 11.

Table 11 shows SEQ ID NOs of the variable regions of the prepared anti-DLL3/CD3 bispecific antibodies.

TABLE 11

| | anti-DLL3 arm | | anti-CD3 arm | |
|---|---|---|---|---|
| Antibody name | Heavy chain variable region | Light chain variable region | Heavy chain variable region | Light chain variable region |
| D30841AE13/TR01 | 69 | 73 | 98 | 103 |
| D30841AE13/hu40G5c | 69 | 73 | 298 | 299 |

The bispecific antibodies generated contain a silent Fc with attenuated affinity for the Fc gamma receptor. For these molecules, the Fab arm exchange technique reported by Igawa et al. (WO 2016159213) was used to make the bispecific antibodies.

Example 14. Measurement of T Cell-Dependent Cell Cytotoxicity (TDCC) of Humanized Anti-DLL3/CD3 Bispecific Antibodies by the Rate of Cell Growth Inhibition The TDCC assay of anti-DLL3/CD3 bispecific antibodies made in Example 13 was performed by methods similar to those described in Example 5.2.2. The SK-MEL 30 human cancer cell line was used as target cells. As for effector cells, frozen PBMCs were used. To prepare frozen PBMCs, cryovials were placed in the water bath at 37 degrees C. to thaw frozen cells. Cells were then dispensed into a 15 mL falcon tube containing 9 mL of media (media used to culture target cells). Cell suspension was then subjected to centrifugation at 1,200 rpm for 5 minutes at room temperature. The supernatant was aspirated gently and fresh warmed medium was added for resuspension. PBMCs were co-cultured with SK-MEL-30 at effector: target ratio of 5. 72 hours after addition of PBMC, cell growth inhibition rate (%) was plotted and shown in FIG. 10.

Figure 10:
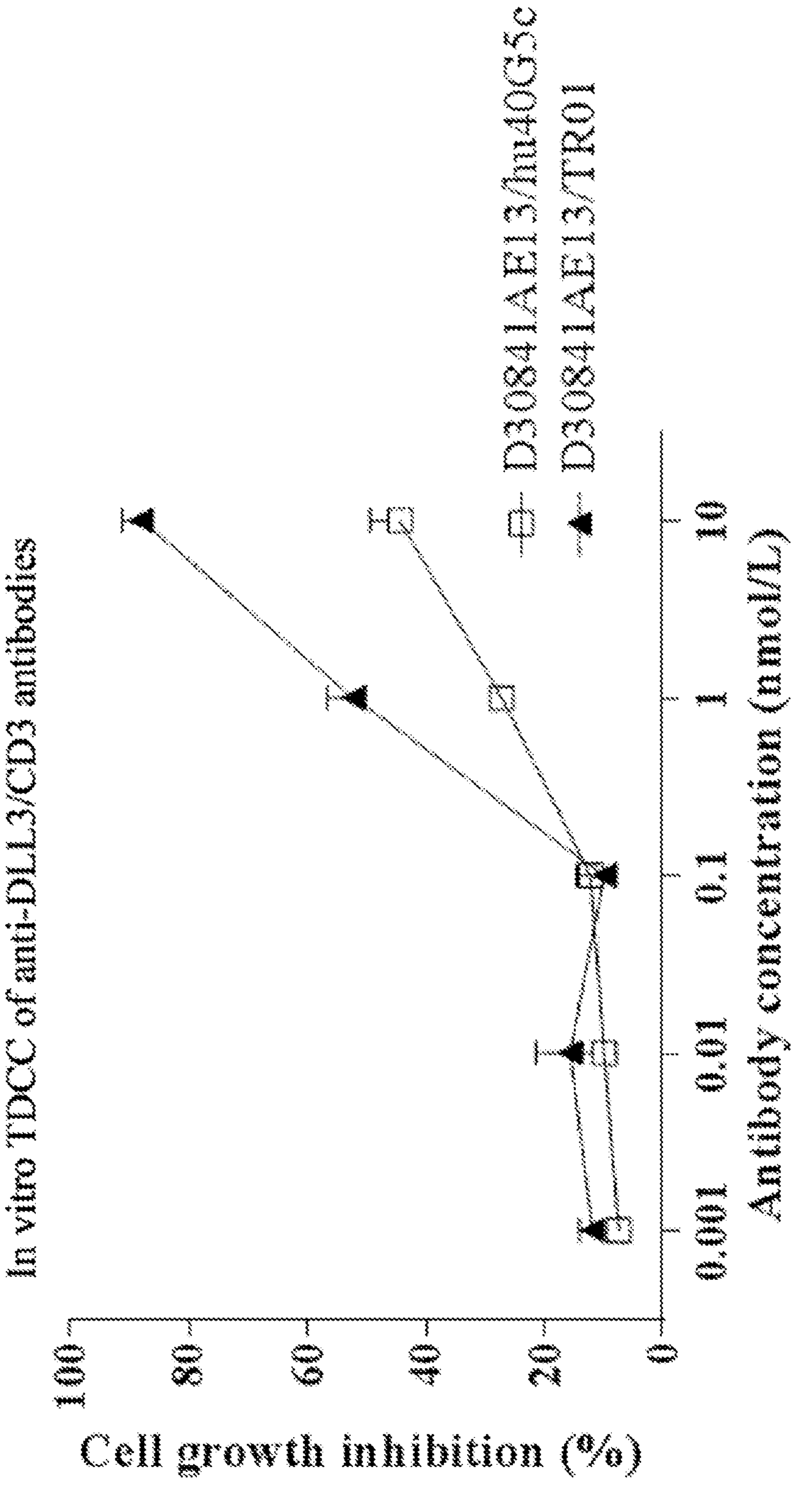
FIG. 10 shows TDCC of humanized anti-DLL3/CD3 bispecific antibodies against SK-MEL-30 cell line. The graph shows cytotoxicity of SK-MEL-30 when co-cultured with PBMC at E:T ratio of 5 in the presence of bi-specific humanized DLL3 antibodies with different anti-CD3 arms at 0.001 nM to 10 nM.

As shown in FIG. 10, both D30841AE13/TR01 and D30841AE13/hu40G5c showed TDCC activity at 1 and 10 nM concentration of bi-specific antibodies.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

INDUSTRIAL APPLICABILITY

The present invention provides novel antigen-binding molecules that have a strong anti-tumor activity and an excellent safety property of not inducing a cytokine storm or such independently from cancer antigens. Cytotoxicity-inducing agents that comprise an antigen-binding molecule of the present invention as an active ingredient can target DLL3-expressing cells and tumor tissues containing these cells and induce cell injury. Administration of an antigen-binding molecule or antibody of the present invention to patients makes it possible to have a desirable treatment that has not only a high level of safety but also a reduced physical burden, and is highly convenient.

Sequence Listing C1-A1723Psq.txt

The invention claimed is:

1. A method of treating cancer, which comprises administering to a patient in need thereof a multispecific antigen-binding molecule that comprises:

(1) a first domain comprising a first antigen-binding domain that binds to human DLL3, and (2) a second domain comprising a second antigen-binding domain that binds to T-cell receptor complex, wherein the first antigen-binding domain comprises any one of (a1) to (a9) below:

(a1) an antibody variable fragment comprising the HVR-H1 sequence of SEQ ID NO: 27, the HVR-H2 sequence of SEQ ID NO: 28, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a2) an antibody variable fragment comprising the HVR-H1 sequence of SEQ ID NO: 33, the HVR-H2 sequence of SEQ ID NO: 34, the HVR-H3 sequence of SEQ ID NO: 35, the HVR-L1 sequence of SEQ ID NO: 36, the HVR-L2 sequence of SEQ ID NO: 37, and the HVR-L3 sequence of SEQ ID NO: 38;

(a3) an antibody variable fragment comprising the HVR-H1 sequence of SEQ ID NO: 39, the HVR-H2 sequence of SEQ ID NO: 40, the HVR-H3 sequence of SEQ ID NO: 41, the HVR-L1 sequence of SEQ ID NO: 42, the HVR-L2 sequence of SEQ ID NO: 43, and the HVR-L3 sequence of SEQ ID NO: 44;

(a4) an antibody variable fragment comprising the HVR-H1 sequence of SEQ ID NO: 45, the HVR-H2 sequence of SEQ ID NO: 46, the HVR-H3 sequence of SEQ ID NO: 47, the HVR-L1 sequence of SEQ ID NO: 48, the HVR-L2 sequence of SEQ ID NO: 49, and the HVR-L3 sequence of SEQ ID NO: 50;

(a5) an antibody variable fragment comprising the HVR-H1 sequence of SEQ ID NO: 27, the HVR-H2 sequence of SEQ ID NO: 75, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a6) an antibody variable fragment comprising the HVR-H1 sequence of SEQ ID NO: 27, the HVR-H2 sequence of SEQ ID NO: 76, the HVR-H3 sequence of SEQ ID NO: 29, the HVR-L1 sequence of SEQ ID NO: 30, the HVR-L2 sequence of SEQ ID NO: 31, and the HVR-L3 sequence of SEQ ID NO: 32;

(a7) an antibody variable fragment comprising the HVR-H1 sequence of SEQ ID NO: 77, the HVR-H2 sequence of SEQ ID NO: 78, the HVR-H3 sequence of SEQ ID NO: 79, the HVR-L1 sequence of SEQ ID NO: 36, the HVR-L2 sequence of SEQ ID NO: 37, and the HVR-L3 sequence of SEQ ID NO: 38;

(a8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38; and (a9) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 81, wherein the cancer expresses DLL3.

2. The method of claim 1, wherein the administered multispecific antigen-binding molecule is a bispecific antibody.

3. The method of claim 1, wherein the first antigen-binding domain of the administered multispecific antigen-binding molecule comprises:

(a8) an antibody variable fragment comprising the HVR-H1 sequence of SEQ ID NO: 77, the HVR-H2 sequence of SEQ ID NO: 78, the HVR-H3 sequence of SEQ ID NO: 80, the HVR-L1 sequence of SEQ ID NO: 36, the HVR-L2 sequence of SEQ ID NO: 37, and the HVR-L3 sequence of SEQ ID NO: 38.

4. The method of claim 1, wherein the second antigen-binding domain of the administered multispecific antigen-binding molecule binds to CD3 epsilon chain.

5. The method of claim 1, wherein the second antigen-binding domain of the administered multispecific antigen-binding molecule binds to T-cell receptor.

6. The method of claim 1, wherein the administered multispecific antigen binding molecule further comprises a third binding domain comprising an Fc region with reduced binding activity towards an Fc gamma receptor.

7. The method of claim 6, wherein the third binding domain of the administered multispecific antigen binding molecule comprises an Fc region with an amino acid mutation at any of the Fc region-constituting amino acids of SEQ ID NOs: 112 to 115 (IgG1 to IgG4).

8. The method of claim 6, wherein the third binding domain of the administered multispecific antigen binding molecule comprises an Fc region with a mutation of at least one amino acid selected from the following amino acid positions specified by EU numbering: position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

9. The method of claim 6, wherein the third binding domain of the administered multispecific antigen binding molecule comprises an Fc region with a mutation at position 235 by EU numbering.

10. The method of claim 1, wherein the cancer expresses DLL3 on the cell surface.

11. The method of claim 10, wherein the cancer is pancreatic cancer, glioma, small cell lung cancer (SCLC), or melanoma.

12. A method of treating cancer, which comprises administering to a patient in need thereof a multispecific antigen-binding molecule that comprises:

(1) a first domain comprising a first antigen-binding domain that binds to human DLL3, and (2) a second domain comprising a second antigen-binding domain that binds to T-cell receptor complex, wherein the first antigen-binding domain comprises any one of (b1) to (b18) below:

(b1) an antibody variable fragment comprising the HVR-H1 sequence identical to the amino acid sequences of the HVR-H1 region comprised in SEQ ID NO: 15, the HVR-H2 sequence identical to the amino acid sequences of the HVR-H2 region comprised in SEQ ID NO: 15, the HVR-H3 sequence identical to the amino acid sequences of the HVR-H3 region comprised in SEQ ID NO: 15, the HVR-L1 sequence identical to the amino acid sequences of the HVR-L1 region comprised in SEQ ID NO: 16, the HVR-L2 sequence identical to the amino acid sequences of the HVR-L2 region comprised in SEQ ID NO: 16, and the HVR-L3 sequence identical to the amino acid sequences of the HVR-L3 region comprised in SEQ ID NO: 16;

(b2) an antibody variable fragment comprising the HVR-H1 sequence identical to the amino acid sequences of the HVR-H1 region comprised in SEQ ID NO: 25, the HVR-H2 sequence identical to the amino acid sequences of the HVR-H2 region comprised in SEQ ID NO: 25, the HVR-H3 sequence identical to the amino acid sequences of the HVR-H3 region comprised in SEQ ID NO: 25, the HVR-L1 sequence identical to the amino acid sequences of the HVR-L1 region comprised in SEQ ID NO: 26, the HVR-L2 sequence identical to the amino acid sequences of the HVR-L2 region comprised in SEQ ID NO: 26, and the HVR-L3 sequence identical to the amino acid sequences of the HVR-L3 region comprised in SEQ ID NO: 26;

(b3) an antibody variable fragment comprising the HVR-H1 sequence identical to the amino acid sequences of the HVR-H1 region comprised in SEQ ID NO: 19, the HVR-H2 sequence identical to the amino acid sequences of the HVR-H2 region comprised in SEQ ID NO: 19, the HVR-H3 sequence identical to the amino acid sequences of the HVR-H3 region comprised in SEQ ID NO: 19, the HVR-L1 sequence identical to the amino acid sequences of the HVR-L1 region comprised in SEQ ID NO: 20, the HVR-L2 sequence identical to the amino acid sequences of the HVR-L2 region comprised in SEQ ID NO: 20, and the HVR-L3 sequence identical to the amino acid sequences of the HVR-L3 region comprised in SEQ ID NO: 20;

(b4) an antibody variable fragment comprising the HVR-H1 sequence identical to the amino acid sequences of the HVR-H1 region comprised in SEQ ID NO: 23, the HVR-H2 sequence identical to the amino acid sequences of the HVR-H2 region comprised in SEQ ID NO: 23, the HVR-H3 sequence identical to the amino acid sequences of the HVR-H3 region comprised in SEQ ID NO: 23, the HVR-L1 sequence identical to the amino acid sequences of the HVR-L1 region comprised in SEQ ID NO: 24, the HVR-L2 sequence identical to the amino acid sequences of the HVR-L2 region comprised in SEQ ID NO: 24, and the HVR-L3 sequence identical to the amino acid sequences of the HVR-L3 region comprised in SEQ ID NO: 24;

(b5) an antibody variable fragment comprising the HVR-H1 sequence identical to the amino acid sequences of the HVR-H1 region comprised in SEQ ID NO: 11, the HVR-H2 sequence identical to the amino acid sequences of the HVR-H2 region comprised in SEQ ID NO: 11, the HVR-H3 sequence identical to the amino acid sequences of the HVR-H3 region comprised in SEQ ID NO: 11, the HVR-L1 sequence identical to the amino acid sequences of the HVR-L1 region comprised in SEQ ID NO: 12, the HVR-L2 sequence identical to the amino acid sequences of the HVR-L2 region comprised in SEQ ID NO: 12, and the HVR-L3 sequence identical to the amino acid sequences of the HVR-L3 region comprised in SEQ ID NO: 12;

(b6) an antibody variable fragment comprising the HVR-H1 sequence identical to the amino acid sequences of the HVR-H1 region comprised in SEQ ID NO: 13, the HVR-H2 sequence identical to the amino acid sequences of the HVR-H2 region comprised in SEQ ID NO: 13, the HVR-H3 sequence identical to the amino acid sequences of the HVR-H3 region comprised in SEQ ID NO: 13, the HVR-L1 sequence identical to the amino acid sequences of the HVR-L1 region comprised in SEQ ID NO: 14, the HVR-L2 sequence identical to the amino acid sequences of the HVR-L2 region comprised in SEQ ID NO: 14, and the HVR-L3 sequence identical to the amino acid sequences of the HVR-L3 region comprised in SEQ ID NO: 14;

(b7) an antibody variable fragment comprising the HVR-H1 sequence identical to the amino acid sequences of the HVR-H1 region comprised in SEQ ID NO: 17, the HVR-H2 sequence identical to the amino acid sequences of the HVR-H2 region comprised in SEQ ID NO: 17, the HVR-H3 sequence identical to the amino acid sequences of the HVR-H3 region comprised in SEQ ID NO: 17, the HVR-L1 sequence identical to the amino acid sequences of the HVR-L1 region comprised in SEQ ID NO: 18, the HVR-L2 sequence identical to the amino acid sequences of the HVR-L2 region comprised in SEQ ID NO: 18, and the HVR-L3 sequence identical to the amino acid sequences of the HVR-L3 region comprised in SEQ ID NO: 18;

(b8) an antibody variable fragment comprising the HVR-H1 sequence identical to the amino acid sequences of the HVR-H1 region comprised in SEQ ID NO: 21, the HVR-H2 sequence identical to the amino acid sequences of the HVR-H2 region comprised in SEQ ID NO: 21, the HVR-H3 sequence identical to the amino acid sequences of the HVR-H3 region comprised in SEQ ID NO: 21, the HVR-L1 sequence identical to the amino acid sequences of the HVR-L1 region comprised in SEQ ID NO: 22, the HVR-L2 sequence identical to the amino acid sequences of the HVR-L2 region comprised in SEQ ID NO: 22, and the HVR-L3 sequence identical to the amino acid sequences of the HVR-L3 region comprised in SEQ ID NO: 22;

(b9) an antibody variable fragment comprising the HVR-H1 sequence identical to the amino acid sequences of the HVR-H1 region comprised in SEQ ID NO: 63, the HVR-H2 sequence identical to the amino acid sequences of the HVR-H2 region comprised in SEQ ID NO: 63, the HVR-H3 sequence identical to the amino acid sequences of the HVR-H3 region comprised in SEQ ID NO: 63, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b10) an antibody variable fragment comprising the HVR-H1 sequence identical to the amino acid sequences of the HVR-H1 region comprised in SEQ ID NO: 64, the HVR-H2 sequence identical to the amino acid sequences of the HVR-H2 region comprised in SEQ ID NO: 64, the HVR-H3 sequence identical to the amino acid sequences of the HVR-H3 region comprised in SEQ ID NO: 64, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b11) an antibody variable fragment comprising the HVR-H1 sequence identical to the amino acid sequences of the HVR-H1 region comprised in SEQ ID NO: 65, the HVR-H2 sequence identical to the amino acid sequences of the HVR-H2 region comprised in SEQ ID NO: 65, the HVR-H3 sequence identical to the amino acid sequences of the HVR-H3 region comprised in SEQ ID NO: 65, the HVR-L1 sequence identical to the amino acid sequences of the HVR-L1 region comprised in SEQ ID NO: 72, the HVR-L2 sequence identical to the amino acid sequences of the HVR-L2 region comprised in SEQ ID NO: 72, and the HVR-L3 sequence identical to the amino acid sequences of the HVR-L3 region comprised in SEQ ID NO: 72;

(b12) an antibody variable fragment comprising the HVR-H1 sequence identical to the amino acid sequences of the HVR-H1 region comprised in SEQ ID NO: 66, the HVR-H2 sequence identical to the amino acid sequences of the HVR-H2 region comprised in SEQ ID NO: 66, the HVR-H3 sequence identical to the amino acid sequences of the HVR-H3 region comprised in SEQ ID NO: 66, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b13) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b14) an antibody variable fragment comprising the HVR-H1 sequence identical to the amino acid sequences of the HVR-H1 region comprised in SEQ ID NO: 67, the HVR-H2 sequence identical to the amino acid sequences of the HVR-H2 region comprised in SEQ ID NO: 67, the HVR-H3 sequence identical to the amino acid sequences of the HVR-H3 region comprised in SEQ ID NO: 67, the HVR-L1 sequence identical to the amino acid sequences of the HVR-L1 region comprised in SEQ ID NO: 74, the HVR-L2 sequence identical to the amino acid sequences of the HVR-L2 region comprised in SEQ ID NO: 74, and the HVR-L3 sequence identical to the amino acid sequences of the HVR-L3 region comprised in SEQ ID NO: 74;

(b15) an antibody variable fragment comprising the HVR-H1 sequence identical to the amino acid sequences of the HVR-H1 region comprised in SEQ ID NO: 68, the HVR-H2 sequence identical to the amino acid sequences of the HVR-H2 region comprised in SEQ ID NO: 68, the HVR-H3 sequence identical to the amino acid sequences of the HVR-H3 region comprised in SEQ ID NO: 68, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b16) an antibody variable fragment comprising the HVR-H1 sequence identical to the amino acid sequences of the HVR-H1 region comprised in SEQ ID NO: 69, the HVR-H2 sequence identical to the amino acid sequences of the HVR-H2 region comprised in SEQ ID NO: 69, the HVR-H3 sequence identical to the amino acid sequences of the HVR-H3 region comprised in SEQ ID NO: 69, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b17) an antibody variable fragment comprising the HVR-H1 sequence identical to the amino acid sequences of the HVR-H1 region comprised in SEQ ID NO: 70, the HVR-H2 sequence identical to the amino acid sequences of the HVR-H2 region comprised in SEQ ID NO: 70, the HVR-H3 sequence identical to the amino acid sequences of the HVR-H3 region comprised in SEQ ID NO: 70, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73;

(b18) an antibody variable fragment comprising the HVR-H1 sequence identical to the amino acid sequences of the HVR-H1 region comprised in SEQ ID NO: 71, the HVR-H2 sequence identical to the amino acid sequences of the HVR-H2 region comprised in SEQ ID NO: 71, the HVR-H3 sequence identical to the amino acid sequences of the HVR-H3 region comprised in SEQ ID NO: 71, the HVR-L1 sequence identical to the amino acid sequences of the HVR-L1 region comprised in SEQ ID NO: 73, the HVR-L2 sequence identical to the amino acid sequences of the HVR-L2 region comprised in SEQ ID NO: 73, and the HVR-L3 sequence identical to the amino acid sequences of the HVR-L3 region comprised in SEQ ID NO: 73, wherein the cancer expresses DLL3.

13. The method of claim 12, wherein the administered multispecific antigen-binding molecule is a bispecific antibody.

14. The method of claim 12, wherein the second antigen-binding domain of the administered multispecific antigen-binding molecule binds to CD3 epsilon chain.

15. The method of claim 12, wherein the second antigen-binding domain of the administered multispecific antigen-binding molecule binds to T-cell receptor.

16. The method of claim 12, wherein the administered multispecific antigen binding molecule further comprises a third binding domain comprising an Fc region with reduced binding activity towards an Fc gamma receptor.

17. The method of claim 16, wherein the third binding domain of the administered multispecific antigen binding molecule comprises an Fc region with an amino acid mutation at any of the Fc region-constituting amino acids of SEQ ID NOs: 112 to 115 (IgG1 to IgG4).

18. The method of claim 16, wherein the third binding domain of the administered multispecific antigen binding molecule comprises an Fc region with a mutation of at least one amino acid selected from the following amino acid positions specified by EU numbering: position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

19. The method of claim 16, wherein the third binding domain of the administered multispecific antigen binding molecule comprises an Fc region with a mutation at position 235 by EU numbering.

20. The method of claim 12, wherein the cancer expresses DLL3 on the cell surface.

21. The method of claim 20, wherein the cancer is pancreatic cancer, glioma, small cell lung cancer (SCLC), or melanoma.

22. The method of claim 1, wherein the first antigen-binding domain of the administered of the administered multispecific antigen-binding molecule comprises any one of the combinations of heavy chain variable region and light chain variable region selected from the following (c1) to (c22):

(c1) heavy chain variable region having the amino acid sequence of SEQ ID NO: 15 and light chain variable region having the amino acid sequence of SEQ ID NO: 16;

(c2) heavy chain variable region having the amino acid sequence of SEQ ID NO: 25 and light chain variable region having the amino acid sequence of SEQ ID NO: 26;

(c3) heavy chain variable region having the amino acid sequence of SEQ ID NO: 19 and light chain variable region having the amino acid sequence of SEQ ID NO: 20;

(c4) heavy chain variable region having the amino acid sequence of SEQ ID NO: 23 and light chain variable region having the amino acid sequence of SEQ ID NO: 24;

(c5) heavy chain variable region having the amino acid sequence of SEQ ID NO: 11 and light chain variable region having the amino acid sequence of SEQ ID NO: 12;

(c6) heavy chain variable region having the amino acid sequence of SEQ ID NO: 13 and light chain variable region having the amino acid sequence of SEQ ID NO: 14;

(c7) heavy chain variable region having the amino acid sequence of SEQ ID NO: 17 and light chain variable region having the amino acid sequence of SEQ ID NO: 18;

(c8) heavy chain variable region having the amino acid sequence of SEQ ID NO: 21 and light chain variable region having the amino acid sequence of SEQ ID NO: 22;

(c9) heavy chain variable region having the amino acid sequence of SEQ ID NO: 63 and light chain variable region having the amino acid sequence of SEQ ID NO: 72;

(c10) heavy chain variable region having the amino acid sequence of SEQ ID NO: 64 and light chain variable region having the amino acid sequence of SEQ ID NO: 72;

(c11) heavy chain variable region having the amino acid sequence of SEQ ID NO: 65 and light chain variable region having the amino acid sequence of SEQ ID NO: 72;

(c12) heavy chain variable region having the amino acid sequence of SEQ ID NO: 66 and light chain variable region having the amino acid sequence of SEQ ID NO: 73;

(c13) heavy chain variable region having the amino acid sequence of SEQ ID NO: 67 and light chain variable region having the amino acid sequence of SEQ ID NO: 73;

(c14) heavy chain variable region having the amino acid sequence of SEQ ID NO: 67 and light chain variable region having the amino acid sequence of SEQ ID NO: 74;

(c15) heavy chain variable region having the amino acid sequence of SEQ ID NO: 68 and light chain variable region having the amino acid sequence of SEQ ID NO: 72;

(c16) heavy chain variable region having the amino acid sequence of SEQ ID NO: 69 and light chain variable region having the amino acid sequence of SEQ ID NO: 73;

(c17) heavy chain variable region having the amino acid sequence of SEQ ID NO: 70 and light chain variable region having the amino acid sequence of SEQ ID NO: 73;

(c18) heavy chain variable region having the amino acid sequence of SEQ ID NO: 71 and light chain variable region having the amino acid sequence of SEQ ID NO: 73.

23. The method of claim 22, wherein the administered multispecific antigen-binding molecule is a bispecific antibody.

24. The method of claim 22, wherein the second antigen-binding domain of the administered multispecific antigen-binding molecule binds to CD3 epsilon chain.

25. The method of claim 22, wherein the second antigen-binding domain of the administered multispecific antigen-binding molecule binds to T-cell receptor.

26. The method of claim 22, wherein the administered multispecific antigen binding molecule further comprises a third binding domain comprising an Fc region with reduced binding activity towards an Fc gamma receptor.

27. The method of claim 26, wherein the third binding domain of the administered multispecific antigen binding molecule comprises an Fc region with an amino acid mutation at any of the Fc region-constituting amino acids of SEQ ID NOs: 112 to 115 (IgG1 to IgG4).

28. The method of claim 26, wherein the third binding domain of the administered multispecific antigen binding molecule comprises an Fc region with a mutation of at least one amino acid selected from the following amino acid positions specified by EU numbering: position 220, position 226, position 229, position 231, position 232, position 233, position 234, position 235, position 236, position 237, position 238, position 239, position 240, position 264, position 265, position 266, position 267, position 269, position 270, position 295, position 296, position 297, position 298, position 299, position 300, position 325, position 327, position 328, position 329, position 330, position 331, and position 332.

29. The method of claim 26, wherein the third binding domain of the administered multispecific antigen binding molecule comprises an Fc region with a mutation at position 235 by EU numbering.

30. The method of claim 22, wherein the cancer expresses DLL3 on the cell surface.

31. The method of claim 22, wherein the cancer is pancreatic cancer, glioma, small cell lung cancer (SCLC), or melanoma.

* * * * *

SEQUENCE LISTING

```
Sequence total quantity: 391
SEQ ID NO: 1            moltype = AA  length = 490
FEATURE                 Location/Qualifiers
REGION                  1..490
                        note = an artificial synthesized sequence
source                  1..490
                        mol_type = protein
                        organism = synthetic construct
SEQUENCE: 1
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
```

```
FGGRDCRERA DPCAARPCAH GGRCYAHFSG LVCACAPGYM GARCEFPVHP DGASALPAAP  480
PGLRPGDPQR                                                         490

SEQ ID NO: 2            moltype = AA  length = 301
FEATURE                 Location/Qualifiers
REGION                  1..301
                        note = an artificial synthesized sequence
source                  1..301
                        mol_type = protein
                        organism = synthetic construct
SEQUENCE: 2
MVLASSTTSI HTMLLLLLML AQPAMAAPLV CRAGCSPEHG FCEQPGECRC LEGWTGPLCT  60
VPVSTSSCLS PRGPSSATTG CLVPGPGPCD GNPCANGGSC SETPRSFECT CPRGFYGLRC  120
EVSGVTCADG PCFNGGLCVG GADPDSAYIC HCPPGFQGSN CEKRVDRCSL QPCRNGGLCL  180
DLGHALRCRC RAGFAGPRCE HDLDDCAGRA CANGGTCVEG GGAHRCSCAL GFGGRDCRER  240
ADPCAARPCA HGGRCYAHFS GLVCACAPGY MGARCEFPVH PDGASALPAA PPGLRPGDPQ  300
R                                                                  301

SEQ ID NO: 3            moltype = AA  length = 243
FEATURE                 Location/Qualifiers
REGION                  1..243
                        note = an artificial synthesized sequence
source                  1..243
                        mol_type = protein
                        organism = synthetic construct
SEQUENCE: 3
MVLASSTTSI HTMLLLLLML AQPAMAGPGP CDGNPCANGG SCSETPRSFE CTCPRGFYGL  60
RCEVSGVTCA DGPCFNGGLC VGGADPDSAY ICHCPPGFQG SNCEKRVDRC SLQPCRNGGL  120
CLDLGHALRC RCRAGFAGPR CEHDLDDCAG RACANGGTCV EGGGAHRCSC ALGFGGRDCR  180
ERADPCAARP CAHGGRCYAH FSGLVCACAP GYMGARCEFP VHPDGASALP AAPPGLRPGD  240
PQR                                                                243

SEQ ID NO: 4            moltype = AA  length = 205
FEATURE                 Location/Qualifiers
REGION                  1..205
                        note = an artificial synthesized sequence
source                  1..205
                        mol_type = protein
                        organism = synthetic construct
SEQUENCE: 4
MVLASSTTSI HTMLLLLLML AQPAMASGVT CADGPCFNGG LCVGGADPDS AYICHCPPGF  60
QGSNCEKRVD RCSLQPCRNG GLCLDLGHAL RCRCRAGFAG PRCEHDLDDC AGRACANGGT  120
CVEGGGAHRC SCALGFGGRD CRERADPCAA RPCAHGGRCY AHFSGLVCAC APGYMGARCE  180
FPVHPDGASA LPAAPPGLRP GDPQR                                        205

SEQ ID NO: 5            moltype = AA  length = 164
FEATURE                 Location/Qualifiers
REGION                  1..164
                        note = an artificial synthesized sequence
source                  1..164
                        mol_type = protein
                        organism = synthetic construct
SEQUENCE: 5
MVLASSTTSI HTMLLLLLML AQPAMARVDR CSLQPCRNGG LCLDLGHALR CRCRAGFAGP  60
RCEHDLDDCA GRACANGGTC VEGGGAHRCS CALGFGGRDC RERADPCAAR PCAHGGRCYA  120
HFSGLVCACA PGYMGARCEF PVHPDGASAL PAAPPGLRPG DPQR                   164

SEQ ID NO: 6            moltype = AA  length = 126
FEATURE                 Location/Qualifiers
REGION                  1..126
                        note = an artificial synthesized sequence
source                  1..126
                        mol_type = protein
                        organism = synthetic construct
SEQUENCE: 6
MVLASSTTSI HTMLLLLLML AQPAMADLDD CAGRACANGG TCVEGGGAHR CSCALGFGGR  60
DCRERADPCA ARPCAHGGRC YAHFSGLVCA CAPGYMGARC EFPVHPDGAS ALPAAPPGLR  120
PGDPQR                                                             126

SEQ ID NO: 7            moltype = AA  length = 88
FEATURE                 Location/Qualifiers
REGION                  1..88
                        note = an artificial synthesized sequence
source                  1..88
                        mol_type = protein
                        organism = synthetic construct
SEQUENCE: 7
MVLASSTTSI HTMLLLLLML AQPAMARADP CAARPCAHGG RCYAHFSGLV CACAPGYMGA  60
RCEFPVHPDG ASALPAAPPG LRPGDPQR                                     88
```

```
SEQ ID NO: 8            moltype = AA  length = 501
FEATURE                 Location/Qualifiers
source                  1..501
                        mol_type = protein
                        organism = Macaca fascicularis
SEQUENCE: 8
MGWSCIILFL VATATGVHSE QKLISEEDLA GVFELQIHSF GPGPGPGAPR SPCSARGPCR  60
LFFRVCLKPG LSEEAAESPC ALGAALSARG PVYTEQPEAP APDLPLPNGL LQVPFRDAWP  120
GTFSLIIETW REELGDQIGG PAWSLLARVT RRRRLAAGGP WARDIQRAGA WELRFSYRAR  180
CELPAVGTAC TRLCRPRSAP SRCGPGLRPC APLEDECEAP PVCRAGCSLE HGFCEQPGEC  240
RCLEGWTGPL CTVPASTSSC LGLRGPSSAT TGCLVPGPGP CDGNPCANGG SCSETPGSFE  300
CTCPRGFYGL RCEVSGVTCA DGPCFNGGLC VGGADPDSAY ICHCPPGFQG SNCEKRVDRC  360
SLQPCRNGGL CLDLGHALRC RCRAGFAGPR CEHNLDDCAG RACANGGTCV EGGGAHRCSC  420
ALGFGGRDCR ERADPCAARP CAHGGRCYAH FSGLVCACAP GYMGSRCEFP VHPDGVSALP  480
AAPPGLRPGD PQRHHHHHHH H                                         501

SEQ ID NO: 9            moltype = AA  length = 618
FEATURE                 Location/Qualifiers
source                  1..618
                        mol_type = protein
                        organism = Homo sapiens
SEQUENCE: 9
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
FGGRDCRERA DPCAARPCAH GGRCYAHFSG LVCACAPGYM GARCEFPVHP DGASALPAAP  480
PGLRPGDPQR YLLPPALGLL VAAGVAGAAL LLVHVRRRGH SQDAGSRLLA GTPEPSVHAL  540
PDALNNLRTQ EGSGDGPSSS VDWNRPEDVD PQGIYVISAP SIYAREVATP LFPPLHTGRA  600
GQRQHLLFPY PSSILSVK                                             618

SEQ ID NO: 10           moltype = AA  length = 107
FEATURE                 Location/Qualifiers
REGION                  1..107
                        note = an artificial synthesized sequence
source                  1..107
                        mol_type = protein
                        organism = synthetic construct
SEQUENCE: 10
RTVAAPSVFI FPPSDEQLKS GTASVVCLLN NFYPREAKVQ WKVDNALQSG NSQESVTEQD  60
SKDCTYSLSS TLTLSKADYE KHKVYACEVT HQGLSSPVTK SFNRGEC              107

SEQ ID NO: 11           moltype = AA  length = 122
FEATURE                 Location/Qualifiers
REGION                  1..122
                        note = an artificial synthesized sequence
source                  1..122
                        mol_type = protein
                        organism = synthetic construct
SEQUENCE: 11
QSVEESGGRL VTPGTPLTLT CTVSGIDLSS YAMSWVRQAP GKGLEWIGII SNSGSGFYAN  60
WAKGRFTISK TSSTTVDVKI SSPTTEDTAT YFCARVFDAD SSGYYYYGMD PWGPGTLVTV  120
SS                                                              122

SEQ ID NO: 12           moltype = AA  length = 111
FEATURE                 Location/Qualifiers
REGION                  1..111
                        note = an artificial synthesized sequence
source                  1..111
                        mol_type = protein
                        organism = synthetic construct
SEQUENCE: 12
DVVMTQTPSS VSEPVGGTVT IKCQASEDIE SYLAWYQQKP GQPPKLLIYA ASTLASGVSS  60
RFRGSGSGTE YTLTISDLEC ADAATYYCQS TYYDSSGVDW AFGGGTEVVV K          111

SEQ ID NO: 13           moltype = AA  length = 123
FEATURE                 Location/Qualifiers
REGION                  1..123
                        note = an artificial synthesized sequence
source                  1..123
                        mol_type = protein
                        organism = synthetic construct
SEQUENCE: 13
QSVEESGGRL VTPGTPLTLT CTVSGFSLSR YAMSWVRQAP GKGLEWIGII TGGGDPYYAS  60
WAKGRFTISK TSTTMDLKIT SPTTEDTATY FCARMIGSEY ASSSEYYDAF DPWGPGTLVT  120
```

```
VSS                                                                 123

SEQ ID NO: 14           moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 14
ALVMTQTPSS VSAAVGGTVT INCQASQNIY SNLAWYQQKP GQRPKLLIYG ASNLESGVPS  60
RFKGSGSGTE YTLTISDLEC DDAAIYYCQS AYYTTSVDVL YPFGGGTEVV VK          112

SEQ ID NO: 15           moltype = AA  length = 124
FEATURE                 Location/Qualifiers
REGION                  1..124
                        note = an artificial synthesized sequence
source                  1..124
                        mol_type = protein
                        organism = synthetic construct
SEQUENCE: 15
QEQLVESGGG LVQPGGSLKL SCKVSGFDFS NYGVSWVRQA PGKGLEWIGY IDPAFGRTYY  60
ASWVNGRFTI SSHNAQNTLY LQLNSLTAAD TATYFCVRVA LVVAGVAYYG MDVWGPGTLV  120
TVSS                                                                124

SEQ ID NO: 16           moltype = AA  length = 114
FEATURE                 Location/Qualifiers
REGION                  1..114
                        note = an artificial synthesized sequence
source                  1..114
                        mol_type = protein
                        organism = synthetic construct
SEQUENCE: 16
ADVVMTQTPA SVEAAVGGTV TINCQASQNI YSYLSWYQQK PGQPPKLLIY RTSTLASGVP  60
SRFKGSGSGT QFTLTISDLE CADAATYYCQ SYYYSSGSSY GAFAFGGGTE VVVK        114

SEQ ID NO: 17           moltype = AA  length = 114
FEATURE                 Location/Qualifiers
REGION                  1..114
                        note = an artificial synthesized sequence
source                  1..114
                        mol_type = protein
                        organism = synthetic construct
SEQUENCE: 17
QSLEESGGRL VTPGTPLTLT CTASGFSLNT YHMIWVRQAP GKGLEWIGIV DSGGSTYYAS  60
WAKGRFTISR TSTTVDLKAT SLTTEDTATY FCARGGSWDG FNIWGPGTLV TVSS        114

SEQ ID NO: 18           moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 18
DVVMTQTPSS VSAAVGGTVT INCQSSQSVY NSDFLAWYQQ KPGQPPKLLI YAASTLASGV  60
PSRFKGSGSG TQFTLTISDL ECDDAATYYC QGTYYEDVGWF NDFGGGTEVV VK         112

SEQ ID NO: 19           moltype = AA  length = 128
FEATURE                 Location/Qualifiers
REGION                  1..128
                        note = an artificial synthesized sequence
source                  1..128
                        mol_type = protein
                        organism = synthetic construct
SEQUENCE: 19
QEQLVESGGG LVQPGASLTL TCKASGFDFT SNAMCWVRQA PGKGPEWIAC IYNDDGSAYS  60
ASWAKGRFTV SKTSSTAVTL QVTGLTAADT ATYFCARSPY YTYGGAPSAY ASGYFNLWGP  120
GTLVTVSS                                                            128

SEQ ID NO: 20           moltype = AA  length = 113
FEATURE                 Location/Qualifiers
REGION                  1..113
                        note = an artificial synthesized sequence
source                  1..113
                        mol_type = protein
                        organism = synthetic construct
SEQUENCE: 20
ADIVMTQTPA SVEAAVGGTV TIKCQASENI YNSLAWYQQK PGQPPKLLMH DASVLTSGVP  60
```

```
SRFSGSGYGT EFTLTISDLE CADAATYYCQ SDYYSTGGSY GFAFGGGTEV VVK         113

SEQ ID NO: 21          moltype = AA  length = 121
FEATURE                Location/Qualifiers
REGION                 1..121
                       note = an artificial synthesized sequence
source                 1..121
                       mol_type = protein
                       organism = synthetic construct
SEQUENCE: 21
QEQLVESGGG LVQPGASLTL TCKASGFSFN TSYCPCWVRQ VPGKGPEWIA CIDAGYSGAT  60
WYANWAKGRF TISKTSSTTV TLQMTSLTGA DTATYFCVRC DAAGSGAFNL WGPGTLVTVS  120
S                                                                  121

SEQ ID NO: 22          moltype = AA  length = 110
FEATURE                Location/Qualifiers
REGION                 1..110
                       note = an artificial synthesized sequence
source                 1..110
                       mol_type = protein
                       organism = synthetic construct
SEQUENCE: 22
AYDMTQTPAS VEVPVGGTVT IKCQASQSIY SYLSWYQQKP GQPPKLLIYE ASKLTSGVPS  60
RFSGSGSGTE FTLTISGVQC DDAATYYCQQ GSGYMDVDNV FGGGTEVVVK             110

SEQ ID NO: 23          moltype = AA  length = 123
FEATURE                Location/Qualifiers
REGION                 1..123
                       note = an artificial synthesized sequence
source                 1..123
                       mol_type = protein
                       organism = synthetic construct
SEQUENCE: 23
QEQLVESGGG LVQPEGSLTL TCTASGFSFS SSGYMCWVRQ APGKGLEWIA CISGGSSGDT  60
DYANWAKGRF SISKTSSTTV TLQMTSLTVA DTATYFCARD VYIDSTIFNF NLWGPGTLVT  120
VSS                                                                123

SEQ ID NO: 24          moltype = AA  length = 111
FEATURE                Location/Qualifiers
REGION                 1..111
                       note = an artificial synthesized sequence
source                 1..111
                       mol_type = protein
                       organism = synthetic construct
SEQUENCE: 24
QVLTQTPSPV SAAVGGTVTI SCQASQSVYN NNNLAWYQQK PGQPPKLLIY AASSLASGVP  60
SRFKGSGAGT QFTLTISDLE CDDAATYYCQ GTYYSSGWYS TFGGGTEVVV K           111

SEQ ID NO: 25          moltype = AA  length = 118
FEATURE                Location/Qualifiers
REGION                 1..118
                       note = an artificial synthesized sequence
source                 1..118
                       mol_type = protein
                       organism = synthetic construct
SEQUENCE: 25
QEQLVESGGG LVQPEGSLTL TCTASGFSFS SSYDMCWVRQ APGKGPEWIA CIYTGDGSTD  60
YASWAKGRFT VSKASSTTVT LQMTSLAVAD TATYFCARNS GYGYFGLWGP GTLVTVSS    118

SEQ ID NO: 26          moltype = AA  length = 109
FEATURE                Location/Qualifiers
REGION                 1..109
                       note = an artificial synthesized sequence
source                 1..109
                       mol_type = protein
                       organism = synthetic construct
SEQUENCE: 26
QVLTQTPSPV SAAVGGTVTI SCQSTESVYG SDWLSWYQQK PGQPPKVLIY QASNLEIGVP  60
SRFKGSGSGT QFTLTISGAQ CDDAATYYCQ GYYSGYIYAF GGGTEVVVK             109

SEQ ID NO: 27          moltype = AA  length = 5
FEATURE                Location/Qualifiers
REGION                 1..5
                       note = an artificial synthesized sequence
source                 1..5
                       mol_type = protein
                       organism = synthetic construct
SEQUENCE: 27
NYGVS                                                              5
```

```
SEQ ID NO: 28          moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 28
YIDPAFGRTY YASWVNG                                                17

SEQ ID NO: 29          moltype = AA  length = 15
FEATURE                Location/Qualifiers
REGION                 1..15
                       note = an artificial synthesized sequence
source                 1..15
                       mol_type = protein
                       organism = synthetic construct
SEQUENCE: 29
VALVVAGVAY YGMDV                                                  15

SEQ ID NO: 30          moltype = AA  length = 11
FEATURE                Location/Qualifiers
REGION                 1..11
                       note = an artificial synthesized sequence
source                 1..11
                       mol_type = protein
                       organism = synthetic construct
SEQUENCE: 30
QASQNIYSYL S                                                      11

SEQ ID NO: 31          moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 31
RTSTLAS                                                           7

SEQ ID NO: 32          moltype = AA  length = 15
FEATURE                Location/Qualifiers
REGION                 1..15
                       note = an artificial synthesized sequence
source                 1..15
                       mol_type = protein
                       organism = synthetic construct
SEQUENCE: 32
QSYYYSSGSS YGAFA                                                  15

SEQ ID NO: 33          moltype = AA  length = 6
FEATURE                Location/Qualifiers
REGION                 1..6
                       note = an artificial synthesized sequence
source                 1..6
                       mol_type = protein
                       organism = synthetic construct
SEQUENCE: 33
SSYDMC                                                            6

SEQ ID NO: 34          moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 34
CIYTGDGSTD YASWAKG                                                17

SEQ ID NO: 35          moltype = AA  length = 9
FEATURE                Location/Qualifiers
REGION                 1..9
                       note = an artificial synthesized sequence
source                 1..9
                       mol_type = protein
                       organism = synthetic construct
SEQUENCE: 35
```

```
NSGYGYFGL                                                          9

SEQ ID NO: 36          moltype = AA  length = 13
FEATURE                Location/Qualifiers
REGION                 1..13
                       note = an artificial synthesized sequence
source                 1..13
                       mol_type = protein
                       organism = synthetic construct
SEQUENCE: 36
QSTESVYGSD WLS                                                     13

SEQ ID NO: 37          moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 37
QASNLEI                                                            7

SEQ ID NO: 38          moltype = AA  length = 10
FEATURE                Location/Qualifiers
REGION                 1..10
                       note = an artificial synthesized sequence
source                 1..10
                       mol_type = protein
                       organism = synthetic construct
SEQUENCE: 38
QGYYSGYIYA                                                         10

SEQ ID NO: 39          moltype = AA  length = 5
FEATURE                Location/Qualifiers
REGION                 1..5
                       note = an artificial synthesized sequence
source                 1..5
                       mol_type = protein
                       organism = synthetic construct
SEQUENCE: 39
SNAMC                                                              5

SEQ ID NO: 40          moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 40
CIYNDDGSAY SASWAKG                                                 17

SEQ ID NO: 41          moltype = AA  length = 20
FEATURE                Location/Qualifiers
REGION                 1..20
                       note = an artificial synthesized sequence
source                 1..20
                       mol_type = protein
                       organism = synthetic construct
SEQUENCE: 41
SPYYTYGGAP SAYASGYFNL                                              20

SEQ ID NO: 42          moltype = AA  length = 11
FEATURE                Location/Qualifiers
REGION                 1..11
                       note = an artificial synthesized sequence
source                 1..11
                       mol_type = protein
                       organism = synthetic construct
SEQUENCE: 42
QASENIYNSL A                                                       11

SEQ ID NO: 43          moltype = AA  length = 7
FEATURE                Location/Qualifiers
REGION                 1..7
                       note = an artificial synthesized sequence
source                 1..7
                       mol_type = protein
                       organism = synthetic construct
```

```
SEQUENCE: 43
DASVLTS                                                      7

SEQ ID NO: 44           moltype = AA  length = 14
FEATURE                 Location/Qualifiers
REGION                  1..14
                        note = an artificial synthesized sequence
source                  1..14
                        mol_type = protein
                        organism = synthetic construct
SEQUENCE: 44
QSDYYSTGGS YGFA                                              14

SEQ ID NO: 45           moltype = AA  length = 6
FEATURE                 Location/Qualifiers
REGION                  1..6
                        note = an artificial synthesized sequence
source                  1..6
                        mol_type = protein
                        organism = synthetic construct
SEQUENCE: 45
SSGYMC                                                       6

SEQ ID NO: 46           moltype = AA  length = 18
FEATURE                 Location/Qualifiers
REGION                  1..18
                        note = an artificial synthesized sequence
source                  1..18
                        mol_type = protein
                        organism = synthetic construct
SEQUENCE: 46
CISGGSSGDT DYANWAKG                                          18

SEQ ID NO: 47           moltype = AA  length = 13
FEATURE                 Location/Qualifiers
REGION                  1..13
                        note = an artificial synthesized sequence
source                  1..13
                        mol_type = protein
                        organism = synthetic construct
SEQUENCE: 47
DVYIDSTIFN FNL                                               13

SEQ ID NO: 48           moltype = AA  length = 13
FEATURE                 Location/Qualifiers
REGION                  1..13
                        note = an artificial synthesized sequence
source                  1..13
                        mol_type = protein
                        organism = synthetic construct
SEQUENCE: 48
QASQSVYNNN NLA                                               13

SEQ ID NO: 49           moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 49
AASSLAS                                                      7

SEQ ID NO: 50           moltype = AA  length = 12
FEATURE                 Location/Qualifiers
REGION                  1..12
                        note = an artificial synthesized sequence
source                  1..12
                        mol_type = protein
                        organism = synthetic construct
SEQUENCE: 50
QGTYYSSGWY ST                                                12

SEQ ID NO: 51           moltype = AA  length = 5
FEATURE                 Location/Qualifiers
REGION                  1..5
                        note = an artificial synthesized sequence
source                  1..5
                        mol_type = protein
```

```
                        organism = synthetic construct
SEQUENCE: 51
DYYMN                                                           5

SEQ ID NO: 52           moltype = AA  length = 19
FEATURE                 Location/Qualifiers
REGION                  1..19
                        note = an artificial synthesized sequence
source                  1..19
                        mol_type = protein
                        organism = synthetic construct
SEQUENCE: 52
LIRNKANGYT TEYNASVKG                                            19

SEQ ID NO: 53           moltype = AA  length = 12
FEATURE                 Location/Qualifiers
REGION                  1..12
                        note = an artificial synthesized sequence
source                  1..12
                        mol_type = protein
                        organism = synthetic construct
SEQUENCE: 53
DSDGYYEYYF DY                                                   12

SEQ ID NO: 54           moltype = AA  length = 11
FEATURE                 Location/Qualifiers
REGION                  1..11
                        note = an artificial synthesized sequence
source                  1..11
                        mol_type = protein
                        organism = synthetic construct
SEQUENCE: 54
RASQEISDYL S                                                    11

SEQ ID NO: 55           moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 55
AASTLDS                                                         7

SEQ ID NO: 56           moltype = AA  length = 9
FEATURE                 Location/Qualifiers
REGION                  1..9
                        note = an artificial synthesized sequence
source                  1..9
                        mol_type = protein
                        organism = synthetic construct
SEQUENCE: 56
LQYASYPYT                                                       9

SEQ ID NO: 57           moltype = AA  length = 125
FEATURE                 Location/Qualifiers
REGION                  1..125
                        note = an artificial synthesized sequence
source                  1..125
                        mol_type = protein
                        organism = synthetic construct
SEQUENCE: 57
EVKLLESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL  120
VTVSA                                                           125

SEQ ID NO: 58           moltype = AA  length = 109
FEATURE                 Location/Qualifiers
REGION                  1..109
                        note = an artificial synthesized sequence
source                  1..109
                        mol_type = protein
                        organism = synthetic construct
SEQUENCE: 58
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNLWVF GGGTKLTVL            109

SEQ ID NO: 59           moltype = AA  length = 987
FEATURE                 Location/Qualifiers
```

```
REGION                  1..987
                        note = an artificial synthesized sequence
source                  1..987
                        mol_type = protein
                        organism = synthetic construct
SEQUENCE: 59
GCTTCCACCA AGGGCCCATC GGTCTTCCCC CTGGCACCCT CCTCCAAGTC GACCTCTGGG  60
GGCACAGCGG CCCTGGGCTG CCTGGTCAAG GACTACTTCC CCGAACCGGT GACGGTGTCG  120
TGGAACTCAG GCGCCCTGAC CAGTGGCGTG CACACCTTCC CGGCTGTCCT ACAGTCCTCA  180
GGACTCTACT CCCTCAGTAG TGTGGTGACC GTGCCCTCCA GTAGTTTGGG CACCCAGACC  240
TACATCTGCA ACGTGAATCA CAAGCCCAGT AACACCAAGG TGGACAAGAA AGTTGAGCCC  300
AAATCTTGTG ACAAAACTCA CACATGCCCA CCGTGCCCAG CACCTGAGCT CCTGGGGGGA  360
CCGTCAGTCT TCCTCTTCCC CCCAAAACCC AAGGACACCC TCATGATCTC CCGGACCCCT  420
GAGGTCACAT GCGTGGTGGT GGACGTGAGT CACGAAGACC CTGAGGTCAA GTTCAACTGG  480
TACGTGGACG GCGTGGAGGT GCATAATGCC AAGACAAAGC CGCGGGAGGA GCAGTACAAC  540
AGTACGTACC GTGTGGTCAG TGTCCTCACC GTCCTGCACC AGGACTGGCT GAATGGCAAG  600
GAGTACAAGT GCAAGGTCTC CAACAAAGCC CTCCCAGCCC CCATCGAGAA AACCATCTCC  660
AAAGCCAAAG GGCAGCCCCG AGAACCACAG GTGTACACCC TGCCCCCATC CCGGGAGGAG  720
ATGACCAAGA ACCAGGTCAG TCTGACCTGC CTGGTCAAAG GCTTCTATCC CAGTGACATC  780
GCCGTGGAGT GGGAGAGTAA TGGGCAGCCG GAGAACAACT ACAAGACCAC GCCTCCCGTG  840
CTGGACTCCG ACGGCTCCTT CTTCCTCTAC AGTAAGCTCA CCGTGGACAA GAGTAGGTGG  900
CAGCAGGGGA ACGTCTTCTC ATGCTCCGTG ATGCATGAGG CTCTGCACAA CCACTACACG  960
CAGAAGAGTC TCTCCCTGTC TCCGTGA                                     987

SEQ ID NO: 60           moltype = AA  length = 328
FEATURE                 Location/Qualifiers
REGION                  1..328
                        note = an artificial synthesized sequence
source                  1..328
                        mol_type = protein
                        organism = synthetic construct
SEQUENCE: 60
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                    328

SEQ ID NO: 61           moltype = AA  length = 324
FEATURE                 Location/Qualifiers
REGION                  1..324
                        note = an artificial synthesized sequence
source                  1..324
                        mol_type = protein
                        organism = synthetic construct
SEQUENCE: 61
CGTACGGTGG CTGCACCATC TGTCTTCATC TTCCCGCCAT CTGATGAGCA GTTGAAATCT  60
GGTACCGCCT CTGTTGTGTG CCTGCTGAAT AACTTCTATC CCAGAGAGGC CAAAGTACAG  120
TGGAAGGTGG ATAACGCCCT CCAATCGGGT AACTCCCAGG AGAGTGTCAC AGAGCAGGAC  180
AGTAAGGACA GTACCTACAG TCTCAGTAGT ACCCTGACGC TGTCCAAAGC AGACTACGAG  240
AAACACAAAG TCTACGCCTG CGAAGTCACC CATCAGGGCC TGTCCTCGCC CGTCACAAAG  300
TCCTTCAACA GGGGAGAGTG TTGA                                        324

SEQ ID NO: 62           moltype = AA  length = 107
FEATURE                 Location/Qualifiers
REGION                  1..107
                        note = an artificial synthesized sequence
source                  1..107
                        mol_type = protein
                        organism = synthetic construct
SEQUENCE: 62
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 63           moltype = AA  length = 124
FEATURE                 Location/Qualifiers
REGION                  1..124
                        note = an artificial synthesized sequence
source                  1..124
                        mol_type = protein
                        organism = synthetic construct
SEQUENCE: 63
EVQLVESGGG LVQPGGSLRL SCAASGFTFS NYGVSWVRQA PGQGLEWMGY IDPAFGRTYY  60
ASWVNGRITI NPDTSKNQFS LQLNSVTPED TAVYYCARVA LVVAGVAYYG MDVWGQGTLV  120
TVSS                                                              124

SEQ ID NO: 64           moltype = AA  length = 124
FEATURE                 Location/Qualifiers
```

```
REGION                  1..124
                        note = an artificial synthesized sequence
source                  1..124
                        mol_type = protein
                        organism = synthetic construct
SEQUENCE: 64
EVQLVESGGG LVQPGGSLRL SCAASGFTFS NYGVSWVRQA PGQGLEWMGY IDIAFGRTYY  60
ASWVQGRITI NPDTSKNQFS LQLNSVTPED TAVYYCARVA LVVAGVAYYG MDVWGQGTLV  120
TVSS                                                               124

SEQ ID NO: 65           moltype = AA  length = 124
FEATURE                 Location/Qualifiers
REGION                  1..124
                        note = an artificial synthesized sequence
source                  1..124
                        mol_type = protein
                        organism = synthetic construct
SEQUENCE: 65
EVQLVESGGG LVQPGGSLRL SCAASGFTFS NYGVSWVRQA PGQGLEWMGY IDIAFGRTYY  60
ASWVTGRITI NPDTSKNQFS LQLNSVTPED TAVYYCARVA LVVAGVAYYG MDVWGQGTLV  120
TVSS                                                               124

SEQ ID NO: 66           moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 66
QVQLKESGPA LVKPTQTLTL TCTFSGFSLS SSYDMGWVRQ APGQGLEWMG TIYTGDYSTD  60
YASWAKGRVT ITADESTSTA YMELSSLRSE DTAVYYCARN TGYGYFGLWG QGTLVTVSS   119

SEQ ID NO: 67           moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 67
QVTLRESGPA LVKPTQTLTL TCTFSGFSLS SSYDMGWVRQ APGQGLEWMG TIYTGDYSTD  60
YASWAKGRVT ISVDTSKNQF SLKLSSVTAA DTAVYYCARH TGYGYFGLWG QGTLVTVSS   119

SEQ ID NO: 68           moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 68
QVTLRESGPA LVKPTQTLTL TCAFSGFSLS SSYDMGWVRQ APGQGLEWMG TIYTGDYSTD  60
YASWAKGRVT ISVDTSKNQF SLKLSSVTAA DTAVYYCARH TGYGYFGLWG QGTLVTVSS   119

SEQ ID NO: 69           moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 69
QVTLRESGPA LVKPTQTLTL TCTFSGFSLS SSYDMGWVRQ APGQGLEWMG TIYTGDYSTD  60
YASWAKGRVT ISVDRSKNQF SLKLSSVTAA DTAVYYCARH TGYGYFGLWG QGTLVTVSS   119

SEQ ID NO: 70           moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 70
QVTLRESGPA LVKPTQTLTL TCTFSGFSLS SSYDMGWVRQ APGQGLEWMG TIYTGDYSTD  60
YASWAKGRVT ISVDSSKNQF SLKLSSVTAA DTAVYYCARH TGYGYFGLWG QGTLVTVSS   119

SEQ ID NO: 71           moltype = AA  length = 119
FEATURE                 Location/Qualifiers
```

```
REGION                  1..119
                        note = an artificial synthesized sequence
source                  1..119
                        mol_type = protein
                        organism = synthetic construct
SEQUENCE: 71
QVTLRESGPA LVKPTQTLTL TCTFSGFSLS SSYDMGWVRQ APGQGLEWMG TIYTGDYSTD  60
YASWAKGRVT ISVDKSKNQF SLKLSSVTAA DTAVYYCARH TGYGYFGLWG QGTLVTVSS   119

SEQ ID NO: 72           moltype = AA  length = 113
FEATURE                 Location/Qualifiers
REGION                  1..113
                        note = an artificial synthesized sequence
source                  1..113
                        mol_type = protein
                        organism = synthetic construct
SEQUENCE: 72
DIVMTQSPDS LAVSLGERAT INCQASQNIY SYLSWYQQKP GKAPKLLIYR TSTLASGVPD  60
RFSGSGSGTD FTLKISRVEA EDVGVYYCQS YYYSSGSSYG AFAFGQGTKV EIK         113

SEQ ID NO: 73           moltype = AA  length = 110
FEATURE                 Location/Qualifiers
REGION                  1..110
                        note = an artificial synthesized sequence
source                  1..110
                        mol_type = protein
                        organism = synthetic construct
SEQUENCE: 73
DIQLTQSPSF LSASVGDRVT ITCQSTESVY GSDWLSWYQQ KPGQPPKLLI YQASNLEIGV  60
PSRFSGSGSG TDFTLTINSL EAEDAATYYC QGYYSGYIYA FGGGTKVEIK            110

SEQ ID NO: 74           moltype = AA  length = 110
FEATURE                 Location/Qualifiers
REGION                  1..110
                        note = an artificial synthesized sequence
source                  1..110
                        mol_type = protein
                        organism = synthetic construct
SEQUENCE: 74
DIQLTQSPSF LSASVGDRVT ITCQSTESVY GSDWLSWYQQ KPGQPPKLLI YQASNLEIGV  60
PSRFSGSGSG TDFTLTINSL EAEDAATYYC QGYYSGYSYA FGGGTKVEIK            110

SEQ ID NO: 75           moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 75
YIDIAFGRTY YASWVQG                                                17

SEQ ID NO: 76           moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 76
YIDIAFGRTY YASWVTG                                                17

SEQ ID NO: 77           moltype = AA  length = 6
FEATURE                 Location/Qualifiers
REGION                  1..6
                        note = an artificial synthesized sequence
source                  1..6
                        mol_type = protein
                        organism = synthetic construct
SEQUENCE: 77
SSYDMG                                                            6

SEQ ID NO: 78           moltype = AA  length = 17
FEATURE                 Location/Qualifiers
REGION                  1..17
                        note = an artificial synthesized sequence
source                  1..17
                        mol_type = protein
                        organism = synthetic construct
```

```
SEQUENCE: 78
TIYTGDYSTD YASWAKG                                                17

SEQ ID NO: 79          moltype = AA  length = 9
FEATURE                Location/Qualifiers
REGION                 1..9
                       note = an artificial synthesized sequence
source                 1..9
                       mol_type = protein
                       organism = synthetic construct
SEQUENCE: 79
NTGYGYFGL                                                         9

SEQ ID NO: 80          moltype = AA  length = 9
FEATURE                Location/Qualifiers
REGION                 1..9
                       note = an artificial synthesized sequence
source                 1..9
                       mol_type = protein
                       organism = synthetic construct
SEQUENCE: 80
HTGYGYFGL                                                         9

SEQ ID NO: 81          moltype = AA  length = 10
FEATURE                Location/Qualifiers
REGION                 1..10
                       note = an artificial synthesized sequence
source                 1..10
                       mol_type = protein
                       organism = synthetic construct
SEQUENCE: 81
QGYYSGYSYA                                                        10

SEQ ID NO: 82          moltype = AA  length = 121
FEATURE                Location/Qualifiers
REGION                 1..121
                       note = an artificial synthesized sequence
source                 1..121
                       mol_type = protein
                       organism = synthetic construct
SEQUENCE: 82
QVQLQQSGAD LVRPGTSVKV SCKASGYAFT NYLIEWIKQR PGQGLEWIGV MNPGSGGTHY  60
SEKFRGKATL TADKSSSTAY MQLISLTSDD SAVYFCARSD YDYVTYAMDY WGQGTSVTVS  120
S                                                                 121

SEQ ID NO: 83          moltype = AA  length = 118
FEATURE                Location/Qualifiers
REGION                 1..118
                       note = an artificial synthesized sequence
source                 1..118
                       mol_type = protein
                       organism = synthetic construct
SEQUENCE: 83
EVQLQQSGPE LVKPGASVKM SCRASGYTFT DYYMKWVKQS HGKSLEWIGD INPNNGDTFY  60
NQKFKGKATL TIDKSSSTAY MQLNSLTSDD SAVYYCARDG NYAYFDYWGQ GTTLTVSS    118

SEQ ID NO: 84          moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 84
QVQLQQSGGD LMKPGASVKI SCKAAGYTFS NYYIEWVKQR PGHGLEWIGE ILPGSGSTTY  60
NEKFKGKASF TADTSSNTAY MQLSSLTSED SAVYYCARWG AREPGFPYWG QGTLVTVSA   119

SEQ ID NO: 85          moltype = AA  length = 123
FEATURE                Location/Qualifiers
REGION                 1..123
                       note = an artificial synthesized sequence
source                 1..123
                       mol_type = protein
                       organism = synthetic construct
SEQUENCE: 85
EVKLVESGGG LVQPGGSLSL SCAASGFTFT DYYMNWVRQP PGKALEWLAL IRNKANGYTT  60
EYNASVKGRF TISRDNSQNI LYLQMNALRA EDSATYYCAR DSDGYYEYYF DYWGQGTTLT  120
VSS                                                               123
```

```
SEQ ID NO: 86          moltype = AA  length = 123
FEATURE                Location/Qualifiers
REGION                 1..123
                       note = an artificial synthesized sequence
source                 1..123
                       mol_type = protein
                       organism = synthetic construct
SEQUENCE: 86
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSS                                                               123

SEQ ID NO: 87          moltype = AA  length = 118
FEATURE                Location/Qualifiers
REGION                 1..118
                       note = an artificial synthesized sequence
source                 1..118
                       mol_type = protein
                       organism = synthetic construct
SEQUENCE: 87
QVQLQESGPG LVKPSETLSL TCTVSGDSIS SYYWTWIRQP PGKGLEWIGY IYYSGTTNYN  60
PSLKSRVTIS VDTSKSQFSL KLSSVTAADT AVYYCASIAV RGFFFDYWGQ GTLVTVSS    118

SEQ ID NO: 88          moltype = AA  length = 118
FEATURE                Location/Qualifiers
REGION                 1..118
                       note = an artificial synthesized sequence
source                 1..118
                       mol_type = protein
                       organism = synthetic construct
SEQUENCE: 88
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSS    118

SEQ ID NO: 89          moltype = AA  length = 118
FEATURE                Location/Qualifiers
REGION                 1..118
                       note = an artificial synthesized sequence
source                 1..118
                       mol_type = protein
                       organism = synthetic construct
SEQUENCE: 89
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSS    118

SEQ ID NO: 90          moltype = AA  length = 107
FEATURE                Location/Qualifiers
REGION                 1..107
                       note = an artificial synthesized sequence
source                 1..107
                       mol_type = protein
                       organism = synthetic construct
SEQUENCE: 90
DIKMTQSPSS MYASLGERVT ITCKASQDIN SYLIWFQQKP GKSPKTLIYR TNRLVDGVPS  60
RFSGSGSGQD YSLTISSLEY GDMGIYYCLQ YDEFPFTFGS GTKLEIK                107

SEQ ID NO: 91          moltype = AA  length = 111
FEATURE                Location/Qualifiers
REGION                 1..111
                       note = an artificial synthesized sequence
source                 1..111
                       mol_type = protein
                       organism = synthetic construct
SEQUENCE: 91
DIVLTQSPAS LAVSLGQRAT ISCRASKSVS TSGYSYMHWY QQKPGQPPKL LIFLASNLES  60
GVPARFSGSG SGTDFTLNIH PVEEEDAATY YCQHSRHLPW TFGGGTKLEI K            111

SEQ ID NO: 92          moltype = AA  length = 107
FEATURE                Location/Qualifiers
REGION                 1..107
                       note = an artificial synthesized sequence
source                 1..107
                       mol_type = protein
                       organism = synthetic construct
SEQUENCE: 92
DIVMTQSQKF MSTSVGDRVS VTCKASQNVG TNVAWYQQKP GQSPKALIYS ASYRYSGVPD  60
RFTGSGSGTD FTLTISNVQS EDLAEYFCQQ YNNYPLTFGA GTKLELK                107

SEQ ID NO: 93          moltype = AA  length = 107
```

```
FEATURE                Location/Qualifiers
REGION                 1..107
                       note = an artificial synthesized sequence
source                 1..107
                       mol_type = protein
                       organism = synthetic construct
SEQUENCE: 93
DIQMTQSPSS LSASLGERVS LTCRASQEIS DYLSWLQQKP DGTIKRLIFA ASTLDSGVPK  60
RFSGSRSGSD FSLSISSLES EDFADYYCLQ YASYPYTFGS GTKLEIK                107

SEQ ID NO: 94          moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 94
DVVMTQTPLS LPVTLGQPAS ISCRSSQSLV YRDGNTYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 95          moltype = AA  length = 108
FEATURE                Location/Qualifiers
REGION                 1..108
                       note = an artificial synthesized sequence
source                 1..108
                       mol_type = protein
                       organism = synthetic construct
SEQUENCE: 95
EIVLTQSPGT LSLSPGERAT LSCRASQSVS SSYLAWYQQK PGQAPRLLIY GASTRATGIP  60
DRFSGSGSGT DFTLTISRLE PEDFAVYYCQ QYGTSPLTFG GGTKVEIK               108

SEQ ID NO: 96          moltype = AA  length = 108
FEATURE                Location/Qualifiers
REGION                 1..108
                       note = an artificial synthesized sequence
source                 1..108
                       mol_type = protein
                       organism = synthetic construct
SEQUENCE: 96
EIVLTQSPGT LSLSPGERVT LSCRASQRVN NNYLAWYQQR PGQAPRLLIY GASSRATGIP  60
DRFSGSGSGT DFTLTISRLE PEDFAVYYCQ QYDRSPLTFG GGTKLEIK               108

SEQ ID NO: 97          moltype = AA  length = 108
FEATURE                Location/Qualifiers
REGION                 1..108
                       note = an artificial synthesized sequence
source                 1..108
                       mol_type = protein
                       organism = synthetic construct
SEQUENCE: 97
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG GGTKVEIK               108

SEQ ID NO: 98          moltype = AA  length = 122
FEATURE                Location/Qualifiers
REGION                 1..122
                       note = an artificial synthesized sequence
source                 1..122
                       mol_type = protein
                       organism = synthetic construct
SEQUENCE: 98
QVQLVESGGG VVQPGGSLRL SCAASGFTFS NAWMHWVRQA PGKGLEWVAQ IKDKSQNYAT  60
YVAESVKGRF TISRADSKNS IYLQMNSLKT EDTAVYYCRY VHYAAGYGVD IWGQGTTVTV  120
SS                                                                 122

SEQ ID NO: 99          moltype = AA  length = 128
FEATURE                Location/Qualifiers
REGION                 1..128
                       note = an artificial synthesized sequence
source                 1..128
                       mol_type = protein
                       organism = synthetic construct
SEQUENCE: 99
QVQLVESGGG LVQPGRSLRL SCAASGFTFS NAWMHWVRQA PGKGLEWVAQ IKDRQNGYNT  60
YYAESVKGRF TISRDDSKNS IYLQMNSLKT EDTAVYYCRY VHYTTTYGSY YQFGVDAWGQ  120
GTTVTVSS                                                           128

SEQ ID NO: 100         moltype = AA  length = 128
```

```
FEATURE                Location/Qualifiers
REGION                 1..128
                       note = an artificial synthesized sequence
source                 1..128
                       mol_type = protein
                       organism = synthetic construct
SEQUENCE: 100
QVQLVESGGG LVQPGRSLRL SCAASGFTFS NAWMHWVRQA PGKGLEWVAQ IKDKQNSYAA  60
YYAESVKGRF TISRDDSKNS IYLQMNSLKT EDTAVYYCRY VHYTTYSGGF FSYGVDAWGQ  120
GTTVTVSS                                                           128

SEQ ID NO: 101         moltype = AA  length = 128
FEATURE                Location/Qualifiers
REGION                 1..128
                       note = an artificial synthesized sequence
source                 1..128
                       mol_type = protein
                       organism = synthetic construct
SEQUENCE: 101
QVQLVESGGG LVQPGRSLRL SCAASGFTFS NAWMHWVRQA PGKGLEWVAQ IKDRANSYNT  60
YYAESVKGRF TISRDDSKNS IYLQMNSLKT EDTAVYYCRY VHYTTYAGSS FSYGVDAWGQ  120
GTTVTVSS                                                           128

SEQ ID NO: 102         moltype = AA  length = 128
FEATURE                Location/Qualifiers
REGION                 1..128
                       note = an artificial synthesized sequence
source                 1..128
                       mol_type = protein
                       organism = synthetic construct
SEQUENCE: 102
QVQLVESGGG LVQPGRSLRL SCAASGFTFS NAWMHWVRQA PGKGLEWVAQ IKDKANGYNA  60
YYAPSVKGRF TISRDDSKNS IYLQMNSLKT EDTAVYYCRY VHYTTFGFGL SYGGVDAWGQ  120
GTTVTVSS                                                           128

SEQ ID NO: 103         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 103
DIVMTQSPLS LPVTPGEPAS ISCRSSQPLV HSNRNTYLHW YQQKPGQAPR LLIYKVSNRF  60
SGVPDRFSGS GSGTDFTLKI SRVEAEDVGV YYCGQGTQVP YTFGQGTKLE IK          112

SEQ ID NO: 104         moltype = AA  length = 141
FEATURE                Location/Qualifiers
source                 1..141
                       mol_type = protein
                       organism = Homo sapiens
SEQUENCE: 104
DIQNPDPAVY QLRDSKSSDK SVCLFTDFDS QTNVSQSKDS DVYITDKTVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                            141

SEQ ID NO: 105         moltype = AA  length = 179
FEATURE                Location/Qualifiers
source                 1..179
                       mol_type = protein
                       organism = Homo sapiens
SEQUENCE: 105
EDLKNVFPPE VAVFEPSEAE ISHTQKATLV CLATGFYPDH VELSWWVNGK EVHSGVSTDP  60
QPLKEQPALN DSRYCLSSRL RVSATFWQNP RNHFRCQVQF YGLSENDEWT QDRAKPVTQI  120
VSAEAWGRAD CGFTSESYQQ GVLSATILYE ILLGKATLYA VLVSALVLMA MVKRKDSRG   179

SEQ ID NO: 106         moltype = AA  length = 173
FEATURE                Location/Qualifiers
source                 1..173
                       mol_type = protein
                       organism = Homo sapiens
SEQUENCE: 106
DKQLDADVSP KPTIFLPSIA ETKLQKAGTY LCLLEKFFPD VIKIHWQEKK SNTILGSQEG  60
NTMKTNDTYM KFSWLTVPEK SLDKEHRCIV RHENNKNGVD QEIIFPPIKT DVITMDPKDN  120
CSKDANDTLL LQLTNTSAYY MYLLLLLKSV VYFAIITCCL LRRTAFCCNG EKS         173

SEQ ID NO: 107         moltype = AA  length = 204
FEATURE                Location/Qualifiers
source                 1..204
```

```
                         mol_type = protein
                         organism = Homo sapiens
SEQUENCE: 107
KQLDADVSPK PTIFLPSIAE TKLQKAGTYL CLLEKFFPDI IKIHWQEKKS NTILGSQEGN  60
TMKTNDTYMK FSWLTVPEES LDKEHRCIVR HENNKNGIDQ EIIFPPIKTD VTTVDPKDSY  120
SKDANDVTTV DPKYNYSKDA NDVITMDPKD NWSKDANDTL LLQLTNTSAY YMYLLLLLKS  180
VVYFAIITCC LLGRTAFCCN GEKS                                        204

SEQ ID NO: 108           moltype = AA  length = 177
FEATURE                  Location/Qualifiers
source                   1..177
                         mol_type = protein
                         organism = Homo sapiens
SEQUENCE: 108
PSYTGGYADK LIFGKGTRVT VEPRSQPHTK PSVFVMKNGT NVACLVKEFY PKDIRINLVS  60
SKKITEFDPA IVISPSGKYN AVKLGKYEDS NSVTCSVQHD NKTVHSTDFE VKTDSTDHVK  120
PKETENTKQP SKSCHKPKAI VHTEKVNMMS LTVLGLRMLF AKTVAVNFLL TAKLFFL     177

SEQ ID NO: 109           moltype = AA  length = 182
FEATURE                  Location/Qualifiers
source                   1..182
                         mol_type = protein
                         organism = Homo sapiens
SEQUENCE: 109
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGFLF  120
AEIVSIFVLA VGVYFIAGQD GVRQSRASDK QTLLPNDQLY QPLKDREDDQ YSHLQGNQLR  180
RN                                                                182

SEQ ID NO: 110           moltype = AA  length = 171
FEATURE                  Location/Qualifiers
source                   1..171
                         mol_type = protein
                         organism = Homo sapiens
SEQUENCE: 110
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGIIVT DVIATLLLAL  120
GVFCFAGHET GRLSGAADTQ ALLRNDQVYQ PLRDRDDAQY SHLGGNWARN K           171

SEQ ID NO: 111           moltype = AA  length = 207
FEATURE                  Location/Qualifiers
source                   1..207
                         mol_type = protein
                         organism = Homo sapiens
SEQUENCE: 111
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                     207

SEQ ID NO: 112           moltype = AA  length = 330
FEATURE                  Location/Qualifiers
source                   1..330
                         mol_type = protein
                         organism = Homo sapiens
SEQUENCE: 112
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 113           moltype = AA  length = 326
FEATURE                  Location/Qualifiers
source                   1..326
                         mol_type = protein
                         organism = Homo sapiens
SEQUENCE: 113
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                      326

SEQ ID NO: 114           moltype = AA  length = 377
FEATURE                  Location/Qualifiers
source                   1..377
```

```
                         mol_type = protein
                         organism = Homo sapiens
SEQUENCE: 114
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 115           moltype = AA  length = 327
FEATURE                  Location/Qualifiers
source                   1..327
                         mol_type = protein
                         organism = Homo sapiens
SEQUENCE: 115
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 116           moltype = AA  length = 4
FEATURE                  Location/Qualifiers
REGION                   1..4
                         note = an artificial synthesized sequence
source                   1..4
                         mol_type = protein
                         organism = synthetic construct
SEQUENCE: 116
GGGS                                                              4

SEQ ID NO: 117           moltype = AA  length = 4
FEATURE                  Location/Qualifiers
REGION                   1..4
                         note = an artificial synthesized sequence
source                   1..4
                         mol_type = protein
                         organism = synthetic construct
SEQUENCE: 117
SGGG                                                              4

SEQ ID NO: 118           moltype = AA  length = 5
FEATURE                  Location/Qualifiers
REGION                   1..5
                         note = an artificial synthesized sequence
source                   1..5
                         mol_type = protein
                         organism = synthetic construct
SEQUENCE: 118
GGGGS                                                             5

SEQ ID NO: 119           moltype = AA  length = 5
FEATURE                  Location/Qualifiers
REGION                   1..5
                         note = an artificial synthesized sequence
source                   1..5
                         mol_type = protein
                         organism = synthetic construct
SEQUENCE: 119
SGGGG                                                             5

SEQ ID NO: 120           moltype = AA  length = 6
FEATURE                  Location/Qualifiers
REGION                   1..6
                         note = an artificial synthesized sequence
source                   1..6
                         mol_type = protein
                         organism = synthetic construct
SEQUENCE: 120
GGGGGS                                                            6

SEQ ID NO: 121           moltype = AA  length = 6
FEATURE                  Location/Qualifiers
REGION                   1..6
                         note = an artificial synthesized sequence
source                   1..6
```

```
                        mol_type = protein
                        organism = synthetic construct
SEQUENCE: 121
SGGGGG                                                          6

SEQ ID NO: 122          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 122
GGGGGGS                                                         7

SEQ ID NO: 123          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 123
SGGGGGG                                                         7

SEQ ID NO: 124          moltype = DNA  length = 1125
FEATURE                 Location/Qualifiers
source                  1..1125
                        mol_type = other DNA
                        organism = Homo sapiens
SEQUENCE: 124
atgtggttct tgacaactct gctcctttgg gttccagttg atgggcaagt ggacaccaca  60
aaggcagtga tcactttgca gcctccatgg gtcagcgtgt tccaagagga aaccgtaacc  120
ttgcactgtg aggtgctcca tctgcctggg agcagctcta cacagtggtt tctcaatggc  180
acagccactc agacctcgac ccccagctac agaatcacct ctgccagtgt caatgacagt  240
ggtgaataca ggtgccagag aggtctctca gggcgaagtg accccataca gctggaaatc  300
cacagaggct ggctactact gcaggtctcc agcagagtct tcacggaagg agaacctctg  360
gccttgaggt gtcatgcgtg gaaggataag ctggtgtaca atgtgcttta ctatcgaaat  420
ggcaaagcct ttaagttttt ccactggaat tctaacctca ccattctgaa aaccaacata  480
agtcacaatg gcacctacca ttgctcaggc atgggaaagc atcgctacac atcagcagga  540
atatctgtca ctgtgaaaga gctatttcca gctccagtgc tgaatgcatc tgtgacatcc  600
ccactcctgg aggggaatct ggtcaccctg agctgtgaaa caaagttgct cttgcagagg  660
cctggtttgc agctttactt ctccttctac atgggcagca agaccctgcg aggcaggaac  720
acatcctctg aataccaaat actaactgct agaagagaag actctgggtt atactggtgc  780
gaggctgcca cagaggatgg aaatgtcctt aagcgcagcc ctgagttgga gcttcaagtg  840
cttggcctcc agttaccaac tcctgtctgg tttcatgtcc ttttctatct ggcagtggga  900
ataatgtttt tagtgaacac tgttctctgg gtgacaatac gtaaagaact gaaaagaaag  960
aaaaagtggg atttagaaat ctctttggat tctggtcatg agaagaaggt aatttccagc  1020
cttcaagaag acagacattt agaagaagag ctgaaatgtc aggaacaaaa agaagaacag  1080
ctgcaggaag gggtgcaccg gaaggagccc caggggggcca cgtag                 1125

SEQ ID NO: 125          moltype = AA  length = 374
FEATURE                 Location/Qualifiers
source                  1..374
                        mol_type = protein
                        organism = Homo sapiens
SEQUENCE: 125
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLQLPTPVW FHVLFYLAVG  300
IMFLVNTVLW VTIRKELKRK KKWDLEISLD SGHEKKVISS LQEDRHLEEE LKCQEQKEEQ  360
LQEGVHRKEP QGAT                                                 374

SEQ ID NO: 126          moltype = DNA  length = 951
FEATURE                 Location/Qualifiers
source                  1..951
                        mol_type = other DNA
                        organism = Homo sapiens
SEQUENCE: 126
atgactatgg agacccaaat gtctcagaat gtatgtccca gaaacctgtg gctgcttcaa  60
ccattgacag ttttgctgct gctggcttct gcagacagtc aagctgctcc cccaaaggct  120
gtgctgaaac ttgagccccc gtggatcaac gtgctccagg aggactctgt gactctgaca  180
tgccaggggg ctcgcagccc tgagagcgac tccattcagt ggttccacaa tgggaatctc  240
attcccaccc acacgcagcc cagctacagg ttcaaggcca acaacaatga cagcggggag  300
tacacgtgcc agactggcca gaccagcctc agcgaccctg tgcatctgac tgtgctttcc  360
gaatggctgg tgctccagac ccctcacctg gagttccagg agggagaaac catcatgctg  420
aggtgccaca gctggaagga caagcctctg gtcaaggtca cattcttcca gaatggaaaa  480
```

```
tcccagaaat tctcccattt ggatcccacc ttctccatcc cacaagcaaa ccacagtcac  540
agtggtgatt accactgcac aggaaacata ggctacacgc tgttctcatc caagcctgtg  600
accatcactg tccaagtgcc cagcatgggc agctcttcac caatgggggt cattgtggct  660
gtggtcattg cgactgctgt agcagccatt gttgctgctg tagtggcctt gatctactgc  720
aggaaaaagc ggatttcagc caattccact gatcctgtga aggctgccca atttgagcca  780
cctggacgtc aaatgattgc catcagaaag agacaacttg aagaaaccaa caatgactat  840
gaaacagctg acggcggcta catgactctg aaccccaggg cacctactga cgatgataaa  900
aacatctacc tgactcttcc tcccaacgac catgtcaaca gtaataacta a           951

SEQ ID NO: 127         moltype = AA  length = 316
FEATURE                Location/Qualifiers
source                 1..316
                       mol_type = protein
                       organism = Homo sapiens
SEQUENCE: 127
MTMETQMSQN VCPRNLWLLQ PLTVLLLLAS ADSQAAPPKA VLKLEPPWIN VLQEDSVTLT  60
CQGARSPESD SIQWFHNGNL IPTHTQPSYR FKANNNDSGE YTCQTGQTSL SDPVHLTVLS  120
EWLVLQTPHL EFQEGETIML RCHSWKDKPL VKVTFFQNGK SQKFSHLDPT FSIPQANHSH  180
SGDYHCTGNI GYTLFSSKPV TITVQVPSMG SSSPMGVIVA VVIATAVAAI VAAVVALIYC  240
RKKRISANST DPVKAAQFEP PGRQMIAIRK RQLEETNNDY ETADGGYMTL NPRAPTDDDK  300
NIYLTLPPND HVNSNN                                                  316

SEQ ID NO: 128         moltype = DNA  length = 876
FEATURE                Location/Qualifiers
source                 1..876
                       mol_type = other DNA
                       organism = Homo sapiens
SEQUENCE: 128
atgggaatcc tgtcattctt acctgtcctt gccactgaga gtgactgggc tgactgcaag  60
tccccccagc cttggggtca tatgcttctg tggacagctg tgctattcct ggctcctgtt  120
gctgggacac ctgcagctcc cccaaaggct gtgctgaaac tcgagcccca gtggatcaac  180
gtgctccagg aggactctgt gactctgaca tgccggggga ctcacagccc tgagagcgac  240
tccattcagt ggttccacaa tgggaatctc attcccaccc acacgcagcc cagctacagg  300
ttcaaggcca acaacaatga cagcggggag tacacgtgcc agactggcca gaccagcctc  360
agcgaccctg tgcatctgac tgtgctttct gagtggctgg tgctccagac ccctcacctg  420
gagttccagg agggagaaac catcgtgctg aggtgccaca gctggaagga caagcctctg  480
gtcaaggtca cattcttcca gaatggaaaa tccaagaaat tttcccgttc ggatcccaac  540
ttctccatcc cacaagcaaa ccacagtcac agtggtgatt accactgcac aggaaacata  600
ggctacacgc tgtactcatc caagcctgtg accatcactg tccaagctcc cagctcttca  660
ccgatgggga tcattgtggc tgtggtcact gggattgctg tagcggccat tgttgctgct  720
gtagtggcct tgatctactg caggaaaaag cggatttcag ccaatcccac taatcctgat  780
gaggctgaca aagttggggc tgagaacaca atcacctatt cacttctcat gcacccggat  840
gctctggaag agcctgatga ccagaaccgt atttag                            876

SEQ ID NO: 129         moltype = AA  length = 291
FEATURE                Location/Qualifiers
source                 1..291
                       mol_type = protein
                       organism = Homo sapiens
SEQUENCE: 129
MGILSFLPVL ATESDWADCK SPQPWGHMLL WTAVLFLAPV AGTPAAPPKA VLKLEPQWIN  60
VLQEDSVTLT CRGTHSPESD SIQWFHNGNL IPTHTQPSYR FKANNNDSGE YTCQTGQTSL  120
SDPVHLTVLS EWLVLQTPHL EFQEGETIVL RCHSWKDKPL VKVTFFQNGK SKKFSRSDPN  180
FSIPQANHSH SGDYHCTGNI GYTLYSSKPV TITVQAPSSS PMGIIVAVVT GIAVAAIVAA  240
VVALIYCRKK RISANPTNPD EADKVGAENT ITYSLLMHPD ALEEPDDQNR I           291

SEQ ID NO: 130         moltype = DNA  length = 765
FEATURE                Location/Qualifiers
source                 1..765
                       mol_type = other DNA
                       organism = Homo sapiens
SEQUENCE: 130
atgtggcagc tgctcctccc aactgctctg ctacttctag tttcagctgg catgcggact  60
gaagatctcc caaaggctgt ggtgttcctg gagcctcaat ggtacagggt gctcgagaag  120
gacagtgtga ctctgaagtg ccagggagcc tactcccctg aggacaattc cacacagtgg  180
tttcacaatg agagcctcat ctcaagccag gcctcgagct acttcattga cgctgccaca  240
gttgacgaca gtggagagta caggtgccag acaaacctct ccaccctcag tgacccggtg  300
cagctagaag tccatatcgg ctggctgttg ctccaggccc ctcggtgggt gttcaaggag  360
gaagacccta ttcacctgag gtgtcacagc tggaagaaca ctgctctgca taaggtcaca  420
tatttacaga atggcaaagg caggaagtat tttcatcata attctgactt ctacattcca  480
aaagccacac tcaaagacag cggctcctac ttctgcaggg ggcttgttgg gagtaaaaat  540
gtgtcttcag agactgtgaa catcaccatc actcaaggtt tgtcagtgtc aaccatctca  600
tcattctttc cacctgggta ccaagtctct ttctgcttgg tgatggtact cctttttgca  660
gtggacacag gactatattt ctctgtgaag acaaacattc gaagctcaac aagagactgg  720
aaggaccata aatttaaatg gagaaaggac cctcaagaca aatga                  765

SEQ ID NO: 131         moltype = AA  length = 254
FEATURE                Location/Qualifiers
source                 1..254
```

```
                         mol_type = protein
                         organism = Homo sapiens
SEQUENCE: 131
MWQLLLPTAL LLLVSAGMRT EDLPKAVVFL EPQWYRVLEK DSVTLKCQGA YSPEDNSTQW  60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLVGSKN  180
VSSETVNITI TQGLSVSTIS SFFPPGYQVS FCLVMVLLFA VDTGLYFSVK TNIRSSTRDW  240
KDHKFKWRKD PQDK                                                   254

SEQ ID NO: 132           moltype = DNA  length = 702
FEATURE                  Location/Qualifiers
source                   1..702
                         mol_type = other DNA
                         organism = Homo sapiens
SEQUENCE: 132
atgtggcagc tgctcctccc aactgctctg ctacttctag tttcagctgg catgcggact  60
gaagatctcc caaaggctgt ggtgttcctg gagcctcaat ggtacagcgt gcttgagaag  120
gacagtgtga ctctgaagtg ccagggagcc tactcccctg aggacaattc cacacagtgg  180
tttcacaatg agagcctcat ctcaagccag gcctcgagct acttcattga cgctgccaca  240
gtcaacgaca gtggagagta caggtgccag acaaacctct ccaccctcag tgacccggtg  300
cagctagaag tccatatcgg ctggctgttg ctccaggccc ctcggtgggt gttcaaggag  360
gaagacccta ttcacctgag gtgtcacagc tggaagaaca ctgctctgca taaggtcaca  420
tatttacaga atggcaaaga caggaagtat tttcatcata attctgactt ccacattcca  480
aaagccacac tcaaagatag cggctcctac ttctgcaggg ggcttgttgg gagtaaaaat  540
gtgtcttcag agactgtgaa catcaccatc actcaaggtt tggcagtgtc aaccatctca  600
tcattctctc cacctgggta ccaagtctct ttctgcttgg tgatggtact cctttttgca  660
gtggacacag gactatattt ctctgtgaag acaaacattt ga                    702

SEQ ID NO: 133           moltype = AA  length = 233
FEATURE                  Location/Qualifiers
source                   1..233
                         mol_type = protein
                         organism = Homo sapiens
SEQUENCE: 133
MWQLLLPTAL LLLVSAGMRT EDLPKAVVFL EPQWYSVLEK DSVTLKCQGA YSPEDNSTQW  60
FHNESLISSQ ASSYFIDAAT VNDSGEYRCQ TNLSTLSDPV QLEVHIGWLL LQAPRWVFKE  120
EDPIHLRCHS WKNTALHKVT YLQNGKDRKY FHHNSDFHIP KATLKDSGSY FCRGLVGSKN  180
VSSETVNITI TQGLAVSTIS SFSPPGYQVS FCLVMVLLFA VDTGLYFSVK TNI        233

SEQ ID NO: 134           moltype = AA  length = 19
FEATURE                  Location/Qualifiers
REGION                   1..19
                         note = an artificial synthesized sequence
source                   1..19
                         mol_type = protein
                         organism = synthetic construct
SEQUENCE: 134
MGWSCIILFL VATATGVHS                                              19

SEQ ID NO: 135           moltype = AA  length = 8
FEATURE                  Location/Qualifiers
REGION                   1..8
                         note = an artificial synthesized sequence
source                   1..8
                         mol_type = protein
                         organism = synthetic construct
SEQUENCE: 135
DYKDDDDK                                                          8

SEQ ID NO: 136           moltype = AA  length = 5
FEATURE                  Location/Qualifiers
REGION                   1..5
                         note = an artificial synthesized sequence
source                   1..5
                         mol_type = protein
                         organism = synthetic construct
SEQUENCE: 136
NYYIH                                                             5

SEQ ID NO: 137           moltype = AA  length = 17
FEATURE                  Location/Qualifiers
REGION                   1..17
                         note = an artificial synthesized sequence
source                   1..17
                         mol_type = protein
                         organism = synthetic construct
SEQUENCE: 137
WIYPGDGNTK YNEKFKG                                                17
```

```
SEQ ID NO: 138          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 138
DSYSNYYFDY                                                    10

SEQ ID NO: 139          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 139
KSSQSLLNSR TRKNYLA                                            17

SEQ ID NO: 140          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 140
WASTRES                                                       7

SEQ ID NO: 141          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 141
TQSFILRT                                                      8

SEQ ID NO: 142          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 142
SYYIH                                                         5

SEQ ID NO: 143          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 143
WIYPENDNTK YNEKFKD                                            17

SEQ ID NO: 144          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 144
DGYSRYYFDY                                                    10

SEQ ID NO: 145          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 145
KSSQSLLNSR TRKNYLA                                            17
```

```
SEQ ID NO: 146          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 146
WTSTRKS                                                            7

SEQ ID NO: 147          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 147
KQSFILRT                                                           8

SEQ ID NO: 148          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 148
DAYSRYYFDY                                                         10

SEQ ID NO: 149          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 149
KQSFALRT                                                           8

SEQ ID NO: 150          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 150
KASFILRT                                                           8

SEQ ID NO: 151          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 151
KQSAILRT                                                           8

SEQ ID NO: 152          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 152
TGYSRYYFDY                                                         10

SEQ ID NO: 153          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 153
```

```
DGYSRYAFDY                                                          10

SEQ ID NO: 154          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 154
SGYSRYYFDY                                                          10

SEQ ID NO: 155          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 155
DGYSRAYFDY                                                          10

SEQ ID NO: 156          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 156
DSYSNYYFDY                                                          10

SEQ ID NO: 157          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 157
TQSFILRT                                                            8

SEQ ID NO: 158          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 158
GYTMN                                                               5

SEQ ID NO: 159          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 159
LINPYKGVST YNQKFKD                                                  17

SEQ ID NO: 160          moltype = AA  length = 13
FEATURE                 Location/Qualifiers
REGION                  1..13
                        note = an artificial synthesized sequence
source                  1..13
                        mol_type = protein
                        organism = synthetic construct
SEQUENCE: 160
SGYYGDSDWY FDV                                                      13

SEQ ID NO: 161          moltype = AA  length = 11
FEATURE                 Location/Qualifiers
REGION                  1..11
                        note = an artificial synthesized sequence
source                  1..11
                        mol_type = protein
                        organism = synthetic construct
```

```
SEQUENCE: 161
RASQDIRNYL N                                                 11

SEQ ID NO: 162         moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 162
YTSRLES                                                      7

SEQ ID NO: 163         moltype = AA  length = 9
FEATURE                Location/Qualifiers
REGION                 1..9
                       note = an artificial synthesized sequence
source                 1..9
                       mol_type = protein
                       organism = synthetic construct
SEQUENCE: 163
QQGNTLPWT                                                    9

SEQ ID NO: 164         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 164
LINPYKGVTT YADSVKG                                           17

SEQ ID NO: 165         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 165
LINPYKGVST YADSVKG                                           17

SEQ ID NO: 166         moltype = AA  length = 5
FEATURE                Location/Qualifiers
REGION                 1..5
                       note = an artificial synthesized sequence
source                 1..5
                       mol_type = protein
                       organism = synthetic construct
SEQUENCE: 166
TYAMN                                                        5

SEQ ID NO: 167         moltype = AA  length = 19
FEATURE                Location/Qualifiers
REGION                 1..19
                       note = an artificial synthesized sequence
source                 1..19
                       mol_type = protein
                       organism = synthetic construct
SEQUENCE: 167
RIRSKYNNYA TYYADSVKD                                         19

SEQ ID NO: 168         moltype = AA  length = 14
FEATURE                Location/Qualifiers
REGION                 1..14
                       note = an artificial synthesized sequence
source                 1..14
                       mol_type = protein
                       organism = synthetic construct
SEQUENCE: 168
HGNFGNSYVS WFAY                                              14

SEQ ID NO: 169         moltype = AA  length = 14
FEATURE                Location/Qualifiers
REGION                 1..14
                       note = an artificial synthesized sequence
source                 1..14
                       mol_type = protein
```

```
                        organism = synthetic construct
SEQUENCE: 169
RSSTGAVTTS NYAN                                                            14

SEQ ID NO: 170          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 170
GTNKRAP                                                                    7

SEQ ID NO: 171          moltype = AA  length = 9
FEATURE                 Location/Qualifiers
REGION                  1..9
                        note = an artificial synthesized sequence
source                  1..9
                        mol_type = protein
                        organism = synthetic construct
SEQUENCE: 171
ALWYSNLWV                                                                  9

SEQ ID NO: 172          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 172
NYGMN                                                                      5

SEQ ID NO: 173          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 173
WINTNTGKPT YAEEFKG                                                         17

SEQ ID NO: 174          moltype = AA  length = 11
FEATURE                 Location/Qualifiers
REGION                  1..11
                        note = an artificial synthesized sequence
source                  1..11
                        mol_type = protein
                        organism = synthetic construct
SEQUENCE: 174
RGDYRYAWFL Y                                                               11

SEQ ID NO: 175          moltype = AA  length = 14
FEATURE                 Location/Qualifiers
REGION                  1..14
                        note = an artificial synthesized sequence
source                  1..14
                        mol_type = protein
                        organism = synthetic construct
SEQUENCE: 175
RSSTGAVTTS NYAN                                                            14

SEQ ID NO: 176          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 176
GTSNRAP                                                                    7

SEQ ID NO: 177          moltype = AA  length = 9
FEATURE                 Location/Qualifiers
REGION                  1..9
                        note = an artificial synthesized sequence
source                  1..9
```

```
                        mol_type = protein
                        organism = synthetic construct
SEQUENCE: 177
ALWYSTHFV                                                     9

SEQ ID NO: 178          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 178
SYYIH                                                         5

SEQ ID NO: 179          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 179
WIYPGNVNTK YNEKFKG                                            17

SEQ ID NO: 180          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 180
NHDYYFDY                                                      8

SEQ ID NO: 181          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 181
KSSQSLLNSR TRKNYLA                                            17

SEQ ID NO: 182          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 182
WASTRES                                                       7

SEQ ID NO: 183          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 183
KQSYILRT                                                      8

SEQ ID NO: 184          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 184
NYAIH                                                         5

SEQ ID NO: 185          moltype = AA  length = 16
FEATURE                 Location/Qualifiers
REGION                  1..16
                        note = an artificial synthesized sequence
```

```
source                 1..16
                       mol_type = protein
                       organism = synthetic construct
SEQUENCE: 185
VIWAGGNTKY NSALMS                                                   16

SEQ ID NO: 186         moltype = AA  length = 11
FEATURE                Location/Qualifiers
REGION                 1..11
                       note = an artificial synthesized sequence
source                 1..11
                       mol_type = protein
                       organism = synthetic construct
SEQUENCE: 186
EDSSGYVALD Y                                                        11

SEQ ID NO: 187         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 187
KSSQSLLSGR TRKNYLA                                                  17

SEQ ID NO: 188         moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 188
WASTRES                                                             7

SEQ ID NO: 189         moltype = AA  length = 8
FEATURE                Location/Qualifiers
REGION                 1..8
                       note = an artificial synthesized sequence
source                 1..8
                       mol_type = protein
                       organism = synthetic construct
SEQUENCE: 189
KQSYYLLT                                                            8

SEQ ID NO: 190         moltype = AA  length = 10
FEATURE                Location/Qualifiers
REGION                 1..10
                       note = an artificial synthesized sequence
source                 1..10
                       mol_type = protein
                       organism = synthetic construct
SEQUENCE: 190
GFSLTNYAIH                                                          10

SEQ ID NO: 191         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 191
GVIWAGGNTK YNSALMS                                                  17

SEQ ID NO: 192         moltype = AA  length = 28
FEATURE                Location/Qualifiers
REGION                 1..28
                       note = an artificial synthesized sequence
source                 1..28
                       mol_type = protein
                       organism = synthetic construct
SEQUENCE: 192
QMNSLRAEDT AVYYCAREDS SGYVALDY                                      28

SEQ ID NO: 193         moltype = AA  length = 17
FEATURE                Location/Qualifiers
REGION                 1..17
```

```
                        note = an artificial synthesized sequence
source                  1..17
                        mol_type = protein
                        organism = synthetic construct
SEQUENCE: 193
KSSQSLLSGR TRKNYLA                                                   17

SEQ ID NO: 194          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 194
WASTRES                                                              7

SEQ ID NO: 195          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 195
KQSYYLLT                                                             8

SEQ ID NO: 196          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 196
GSAMH                                                                5

SEQ ID NO: 197          moltype = AA  length = 19
FEATURE                 Location/Qualifiers
REGION                  1..19
                        note = an artificial synthesized sequence
source                  1..19
                        mol_type = protein
                        organism = synthetic construct
SEQUENCE: 197
RIRSRANSYA TAYAASVKD                                                 19

SEQ ID NO: 198          moltype = AA  length = 9
FEATURE                 Location/Qualifiers
REGION                  1..9
                        note = an artificial synthesized sequence
source                  1..9
                        mol_type = protein
                        organism = synthetic construct
SEQUENCE: 198
DTMVRGIDY                                                            9

SEQ ID NO: 199          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 199
KSSQSVLYSS NNKNYLV                                                   17

SEQ ID NO: 200          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 200
RASTRES                                                              7

SEQ ID NO: 201          moltype = AA  length = 9
FEATURE                 Location/Qualifiers
```

```
REGION                  1..9
                        note = an artificial synthesized sequence
source                  1..9
                        mol_type = protein
                        organism = synthetic construct
SEQUENCE: 201
QQYYSVPWT                                                    9

SEQ ID NO: 202          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 202
SDYIH                                                        5

SEQ ID NO: 203          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 203
WIYFGNVNTK YNEKFKG                                           17

SEQ ID NO: 204          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 204
DGGYYFDY                                                     8

SEQ ID NO: 205          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 205
KSSQSLLNSR TRKNYLA                                           17

SEQ ID NO: 206          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 206
WASTRES                                                      7

SEQ ID NO: 207          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 207
KQSFTLRT                                                     8

SEQ ID NO: 208          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 208
SHYLH                                                        5

SEQ ID NO: 209          moltype = AA  length = 17
```

```
FEATURE              Location/Qualifiers
REGION               1..17
                     note = an artificial synthesized sequence
source               1..17
                     mol_type = protein
                     organism = synthetic construct
SEQUENCE: 209
WINPGDGNVK YNEKFKD                                             17

SEQ ID NO: 210       moltype = AA  length = 8
FEATURE              Location/Qualifiers
REGION               1..8
                     note = an artificial synthesized sequence
source               1..8
                     mol_type = protein
                     organism = synthetic construct
SEQUENCE: 210
DGAYYFDY                                                       8

SEQ ID NO: 211       moltype = AA  length = 17
FEATURE              Location/Qualifiers
REGION               1..17
                     note = an artificial synthesized sequence
source               1..17
                     mol_type = protein
                     organism = synthetic construct
SEQUENCE: 211
KSSQSLLNSR TRKNYLA                                             17

SEQ ID NO: 212       moltype = AA  length = 7
FEATURE              Location/Qualifiers
REGION               1..7
                     note = an artificial synthesized sequence
source               1..7
                     mol_type = protein
                     organism = synthetic construct
SEQUENCE: 212
WASTRES                                                        7

SEQ ID NO: 213       moltype = AA  length = 8
FEATURE              Location/Qualifiers
REGION               1..8
                     note = an artificial synthesized sequence
source               1..8
                     mol_type = protein
                     organism = synthetic construct
SEQUENCE: 213
KQSYTLRT                                                       8

SEQ ID NO: 214       moltype = AA  length = 5
FEATURE              Location/Qualifiers
REGION               1..5
                     note = an artificial synthesized sequence
source               1..5
                     mol_type = protein
                     organism = synthetic construct
SEQUENCE: 214
SYYIH                                                          5

SEQ ID NO: 215       moltype = AA  length = 17
FEATURE              Location/Qualifiers
REGION               1..17
                     note = an artificial synthesized sequence
source               1..17
                     mol_type = protein
                     organism = synthetic construct
SEQUENCE: 215
WIFPGSDNTK YNEKFKG                                             17

SEQ ID NO: 216       moltype = AA  length = 8
FEATURE              Location/Qualifiers
REGION               1..8
                     note = an artificial synthesized sequence
source               1..8
                     mol_type = protein
                     organism = synthetic construct
SEQUENCE: 216
NGNYAMDY                                                       8
```

```
SEQ ID NO: 217          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 217
KSSQSLLNSR TRKNYLA                                                 17

SEQ ID NO: 218          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 218
WASTRES                                                            7

SEQ ID NO: 219          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 219
KQSYTLRT                                                           8

SEQ ID NO: 220          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 220
SYYIH                                                              5

SEQ ID NO: 221          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 221
WIYPGNVNTK YNEKFKG                                                 17

SEQ ID NO: 222          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 222
NHDYYFDY                                                           8

SEQ ID NO: 223          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 223
KSSQSLLNSR TRKNYLA                                                 17

SEQ ID NO: 224          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 224
WASTRES                                                            7
```

```
SEQ ID NO: 225          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 225
KQSYILRT                                                                   8

SEQ ID NO: 226          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 226
NYGMN                                                                      5

SEQ ID NO: 227          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 227
WINTNTGKPT YAEDFKG                                                         17

SEQ ID NO: 228          moltype = AA  length = 11
FEATURE                 Location/Qualifiers
REGION                  1..11
                        note = an artificial synthesized sequence
source                  1..11
                        mol_type = protein
                        organism = synthetic construct
SEQUENCE: 228
RGDYRYAWFT Y                                                               11

SEQ ID NO: 229          moltype = AA  length = 14
FEATURE                 Location/Qualifiers
REGION                  1..14
                        note = an artificial synthesized sequence
source                  1..14
                        mol_type = protein
                        organism = synthetic construct
SEQUENCE: 229
RSSTGAVTTS NYAN                                                            14

SEQ ID NO: 230          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 230
GTSNRAP                                                                    7

SEQ ID NO: 231          moltype = AA  length = 9
FEATURE                 Location/Qualifiers
REGION                  1..9
                        note = an artificial synthesized sequence
source                  1..9
                        mol_type = protein
                        organism = synthetic construct
SEQUENCE: 231
ALWYSTHFV                                                                  9

SEQ ID NO: 232          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 232
```

```
NYYIH                                                           5

SEQ ID NO: 233          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 233
WIYPGSDNTK FNDKFKG                                              17

SEQ ID NO: 234          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 234
DSITNYYFDY                                                      10

SEQ ID NO: 235          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 235
KSSQSLLNIR TRKNCLA                                              17

SEQ ID NO: 236          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 236
WASTRYS                                                         7

SEQ ID NO: 237          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 237
TQSYTLRT                                                        8

SEQ ID NO: 238          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 238
SYWMH                                                           5

SEQ ID NO: 239          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 239
NFYPGDLTVN YDEKFKN                                              17

SEQ ID NO: 240          moltype = AA  length = 10
FEATURE                 Location/Qualifiers
REGION                  1..10
                        note = an artificial synthesized sequence
source                  1..10
                        mol_type = protein
                        organism = synthetic construct
```

```
SEQUENCE: 240
DAYSRYFFDY                                                        10

SEQ ID NO: 241          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 241
KSSQSLLNSR TRKNYLA                                                17

SEQ ID NO: 242          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 242
WASTRES                                                           7

SEQ ID NO: 243          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 243
CQSFILRT                                                          8

SEQ ID NO: 244          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 244
NYYMH                                                             5

SEQ ID NO: 245          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 245
WISPGSGSIK YNEKFKG                                                17

SEQ ID NO: 246          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 246
DGYSLYFFDF                                                        10

SEQ ID NO: 247          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 247
KSSQSLLNSR TRKNYLA                                                17

SEQ ID NO: 248          moltype = AA  length = 7
FEATURE                 Location/Qualifiers
REGION                  1..7
                        note = an artificial synthesized sequence
source                  1..7
                        mol_type = protein
```

```
                       organism = synthetic construct
SEQUENCE: 248
WASTRES                                                                  7

SEQ ID NO: 249         moltype = AA  length = 8
FEATURE                Location/Qualifiers
REGION                 1..8
                       note = an artificial synthesized sequence
source                 1..8
                       mol_type = protein
                       organism = synthetic construct
SEQUENCE: 249
KQSFILRT                                                                 8

SEQ ID NO: 250         moltype = AA  length = 5
FEATURE                Location/Qualifiers
REGION                 1..5
                       note = an artificial synthesized sequence
source                 1..5
                       mol_type = protein
                       organism = synthetic construct
SEQUENCE: 250
NYYTH                                                                    5

SEQ ID NO: 251         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 251
WIYPGNGNIK YNEKFMG                                                       17

SEQ ID NO: 252         moltype = AA  length = 10
FEATURE                Location/Qualifiers
REGION                 1..10
                       note = an artificial synthesized sequence
source                 1..10
                       mol_type = protein
                       organism = synthetic construct
SEQUENCE: 252
DSYGSYYFDY                                                               10

SEQ ID NO: 253         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 253
KSSQSLLNSR TRKNYLA                                                       17

SEQ ID NO: 254         moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 254
WASTRES                                                                  7

SEQ ID NO: 255         moltype = AA  length = 8
FEATURE                Location/Qualifiers
REGION                 1..8
                       note = an artificial synthesized sequence
source                 1..8
                       mol_type = protein
                       organism = synthetic construct
SEQUENCE: 255
TQSFILRT                                                                 8

SEQ ID NO: 256         moltype = AA  length = 5
FEATURE                Location/Qualifiers
REGION                 1..5
                       note = an artificial synthesized sequence
source                 1..5
```

```
                        mol_type = protein
                        organism = synthetic construct
SEQUENCE: 256
NYYTH                                                                5

SEQ ID NO: 257          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 257
WIYPGNGNIK YNEKFMG                                                   17

SEQ ID NO: 258          moltype = AA  length = 10
FEATURE                 Location/Qualifiers
REGION                  1..10
                        note = an artificial synthesized sequence
source                  1..10
                        mol_type = protein
                        organism = synthetic construct
SEQUENCE: 258
DSYGSYYFDY                                                           10

SEQ ID NO: 259          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 259
KSSQSLLNSR TRKNYLA                                                   17

SEQ ID NO: 260          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 260
WASTRES                                                              7

SEQ ID NO: 261          moltype = AA  length = 8
FEATURE                 Location/Qualifiers
REGION                  1..8
                        note = an artificial synthesized sequence
source                  1..8
                        mol_type = protein
                        organism = synthetic construct
SEQUENCE: 261
KQSFILRT                                                             8

SEQ ID NO: 262          moltype = AA  length = 5
FEATURE                 Location/Qualifiers
REGION                  1..5
                        note = an artificial synthesized sequence
source                  1..5
                        mol_type = protein
                        organism = synthetic construct
SEQUENCE: 262
NYYTH                                                                5

SEQ ID NO: 263          moltype = AA  length = 17
FEATURE                 Location/Qualifiers
REGION                  1..17
                        note = an artificial synthesized sequence
source                  1..17
                        mol_type = protein
                        organism = synthetic construct
SEQUENCE: 263
WLYPGNGDTR YNEKFKD                                                   17

SEQ ID NO: 264          moltype = AA  length = 10
FEATURE                 Location/Qualifiers
REGION                  1..10
                        note = an artificial synthesized sequence
```

```
source                1..10
                      mol_type = protein
                      organism = synthetic construct
SEQUENCE: 264
DSYGNYFFDY                                                    10

SEQ ID NO: 265        moltype = AA  length = 17
FEATURE               Location/Qualifiers
REGION                1..17
                      note = an artificial synthesized sequence
source                1..17
                      mol_type = protein
                      organism = synthetic construct
SEQUENCE: 265
KSSQSLLNSR TRKNYLA                                            17

SEQ ID NO: 266        moltype = AA  length = 7
FEATURE               Location/Qualifiers
REGION                1..7
                      note = an artificial synthesized sequence
source                1..7
                      mol_type = protein
                      organism = synthetic construct
SEQUENCE: 266
WASTRES                                                       7

SEQ ID NO: 267        moltype = AA  length = 8
FEATURE               Location/Qualifiers
REGION                1..8
                      note = an artificial synthesized sequence
source                1..8
                      mol_type = protein
                      organism = synthetic construct
SEQUENCE: 267
KQSFILRT                                                      8

SEQ ID NO: 268        moltype = AA  length = 5
FEATURE               Location/Qualifiers
REGION                1..5
                      note = an artificial synthesized sequence
source                1..5
                      mol_type = protein
                      organism = synthetic construct
SEQUENCE: 268
SYWMH                                                         5

SEQ ID NO: 269        moltype = AA  length = 17
FEATURE               Location/Qualifiers
REGION                1..17
                      note = an artificial synthesized sequence
source                1..17
                      mol_type = protein
                      organism = synthetic construct
SEQUENCE: 269
NSYPGDLNVN YDEKFKN                                            17

SEQ ID NO: 270        moltype = AA  length = 10
FEATURE               Location/Qualifiers
REGION                1..10
                      note = an artificial synthesized sequence
source                1..10
                      mol_type = protein
                      organism = synthetic construct
SEQUENCE: 270
DAYSRYFFDY                                                    10

SEQ ID NO: 271        moltype = AA  length = 17
FEATURE               Location/Qualifiers
REGION                1..17
                      note = an artificial synthesized sequence
source                1..17
                      mol_type = protein
                      organism = synthetic construct
SEQUENCE: 271
KSSQSLLNSR TRKNYLA                                            17

SEQ ID NO: 272        moltype = AA  length = 7
FEATURE               Location/Qualifiers
REGION                1..7
```

```
                          note = an artificial synthesized sequence
source                    1..7
                          mol_type = protein
                          organism = synthetic construct
SEQUENCE: 272
WASTRES                                                          7

SEQ ID NO: 273            moltype = AA  length = 8
FEATURE                   Location/Qualifiers
REGION                    1..8
                          note = an artificial synthesized sequence
source                    1..8
                          mol_type = protein
                          organism = synthetic construct
SEQUENCE: 273
CQSFILRT                                                         8

SEQ ID NO: 274            moltype = AA  length = 5
FEATURE                   Location/Qualifiers
REGION                    1..5
                          note = an artificial synthesized sequence
source                    1..5
                          mol_type = protein
                          organism = synthetic construct
SEQUENCE: 274
SYYIH                                                            5

SEQ ID NO: 275            moltype = AA  length = 17
FEATURE                   Location/Qualifiers
REGION                    1..17
                          note = an artificial synthesized sequence
source                    1..17
                          mol_type = protein
                          organism = synthetic construct
SEQUENCE: 275
WLYPGDVSTR YNEKFRD                                               17

SEQ ID NO: 276            moltype = AA  length = 10
FEATURE                   Location/Qualifiers
REGION                    1..10
                          note = an artificial synthesized sequence
source                    1..10
                          mol_type = protein
                          organism = synthetic construct
SEQUENCE: 276
DSSASYYFDF                                                       10

SEQ ID NO: 277            moltype = AA  length = 17
FEATURE                   Location/Qualifiers
REGION                    1..17
                          note = an artificial synthesized sequence
source                    1..17
                          mol_type = protein
                          organism = synthetic construct
SEQUENCE: 277
KSSQSLLNIR TRKNYLA                                               17

SEQ ID NO: 278            moltype = AA  length = 7
FEATURE                   Location/Qualifiers
REGION                    1..7
                          note = an artificial synthesized sequence
source                    1..7
                          mol_type = protein
                          organism = synthetic construct
SEQUENCE: 278
WASTRAS                                                          7

SEQ ID NO: 279            moltype = AA  length = 8
FEATURE                   Location/Qualifiers
REGION                    1..8
                          note = an artificial synthesized sequence
source                    1..8
                          mol_type = protein
                          organism = synthetic construct
SEQUENCE: 279
TQSFILRT                                                         8

SEQ ID NO: 280            moltype = AA  length = 5
FEATURE                   Location/Qualifiers
```

```
REGION                 1..5
                       note = an artificial synthesized sequence
source                 1..5
                       mol_type = protein
                       organism = synthetic construct
SEQUENCE: 280
SYWMH                                                                5

SEQ ID NO: 281         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 281
NIYPGGEIIN YAEKFKT                                                   17

SEQ ID NO: 282         moltype = AA  length = 10
FEATURE                Location/Qualifiers
REGION                 1..10
                       note = an artificial synthesized sequence
source                 1..10
                       mol_type = protein
                       organism = synthetic construct
SEQUENCE: 282
DTTGNYFFDY                                                           10

SEQ ID NO: 283         moltype = AA  length = 17
FEATURE                Location/Qualifiers
REGION                 1..17
                       note = an artificial synthesized sequence
source                 1..17
                       mol_type = protein
                       organism = synthetic construct
SEQUENCE: 283
KSSQSLLNSR TRKNYLA                                                   17

SEQ ID NO: 284         moltype = AA  length = 7
FEATURE                Location/Qualifiers
REGION                 1..7
                       note = an artificial synthesized sequence
source                 1..7
                       mol_type = protein
                       organism = synthetic construct
SEQUENCE: 284
WASTRES                                                              7

SEQ ID NO: 285         moltype = AA  length = 8
FEATURE                Location/Qualifiers
REGION                 1..8
                       note = an artificial synthesized sequence
source                 1..8
                       mol_type = protein
                       organism = synthetic construct
SEQUENCE: 285
TQSFILRT                                                             8

SEQ ID NO: 286         moltype = AA  length = 5
FEATURE                Location/Qualifiers
REGION                 1..5
                       note = an artificial synthesized sequence
source                 1..5
                       mol_type = protein
                       organism = synthetic construct
SEQUENCE: 286
SCAIS                                                                5

SEQ ID NO: 287         moltype = AA  length = 16
FEATURE                Location/Qualifiers
REGION                 1..16
                       note = an artificial synthesized sequence
source                 1..16
                       mol_type = protein
                       organism = synthetic construct
SEQUENCE: 287
FMSVTGSAYY ANWAKS                                                    16

SEQ ID NO: 288         moltype = AA  length = 9
```

```
FEATURE              Location/Qualifiers
REGION               1..9
                     note = an artificial synthesized sequence
source               1..9
                     mol_type = protein
                     organism = synthetic construct
SEQUENCE: 288
VGIGSGLNI                                                    9

SEQ ID NO: 289       moltype = AA  length = 13
FEATURE              Location/Qualifiers
REGION               1..13
                     note = an artificial synthesized sequence
source               1..13
                     mol_type = protein
                     organism = synthetic construct
SEQUENCE: 289
QASETVYSNN YLA                                               13

SEQ ID NO: 290       moltype = AA  length = 7
FEATURE              Location/Qualifiers
REGION               1..7
                     note = an artificial synthesized sequence
source               1..7
                     mol_type = protein
                     organism = synthetic construct
SEQUENCE: 290
GVSTLDS                                                      7

SEQ ID NO: 291       moltype = AA  length = 12
FEATURE              Location/Qualifiers
REGION               1..12
                     note = an artificial synthesized sequence
source               1..12
                     mol_type = protein
                     organism = synthetic construct
SEQUENCE: 291
AGYKTSSSYA IA                                                12

SEQ ID NO: 292       moltype = AA  length = 5
FEATURE              Location/Qualifiers
REGION               1..5
                     note = an artificial synthesized sequence
source               1..5
                     mol_type = protein
                     organism = synthetic construct
SEQUENCE: 292
DYYIH                                                        5

SEQ ID NO: 293       moltype = AA  length = 17
FEATURE              Location/Qualifiers
REGION               1..17
                     note = an artificial synthesized sequence
source               1..17
                     mol_type = protein
                     organism = synthetic construct
SEQUENCE: 293
WIYPGDVSTR FNEKFKG                                           17

SEQ ID NO: 294       moltype = AA  length = 10
FEATURE              Location/Qualifiers
REGION               1..10
                     note = an artificial synthesized sequence
source               1..10
                     mol_type = protein
                     organism = synthetic construct
SEQUENCE: 294
DSYGNYFFDY                                                   10

SEQ ID NO: 295       moltype = AA  length = 17
FEATURE              Location/Qualifiers
REGION               1..17
                     note = an artificial synthesized sequence
source               1..17
                     mol_type = protein
                     organism = synthetic construct
SEQUENCE: 295
KSSQSLLNSR TRKNYLA                                           17
```

```
SEQ ID NO: 296          moltype = AA  length = 7
FEATURE                 Location/Qualifiers
REGION                  1..7
                        note = an artificial synthesized sequence
source                  1..7
                        mol_type = protein
                        organism = synthetic construct
SEQUENCE: 296
WASTRES                                                       7

SEQ ID NO: 297          moltype = AA  length = 9
FEATURE                 Location/Qualifiers
REGION                  1..9
                        note = an artificial synthesized sequence
source                  1..9
                        mol_type = protein
                        organism = synthetic construct
SEQUENCE: 297
CTQSFILRT                                                     9

SEQ ID NO: 298          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 298
EVQLVQSGAE VKKPGASVKV SCKASGYTFT NYYIHWVRQA PGQGLEWIGW IYPGDGNTKY  60
NEKFKGRATL TADTSTSTAY LELSSLRSED TAVYYCARDS YSNYYFDYWG QGTLVTVSS   119

SEQ ID NO: 299          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 299
DIVMTQSPDS LAVSLGERAT INCKSSQSLL NSRTRKNYLA WYQQKPGQPP KLLIYWASTR  60
ESGVPDRFSG SGSGTDFTLT ISSLQAEDVA VYYCTQSFIL RTFGQGTKVE IK          112

SEQ ID NO: 300          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 300
QVQLQQSGPE LVKPGASVKI SCKASGYTFT NYYIHWVKQR PGQGLEWIGW IYPGDGNTKY  60
NEKFKGKATL TADTSSSTAY MQLSSLTSED SAVYYCARDS YSNYYFDYWG QGTTLTVSS   119

SEQ ID NO: 301          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 301
DIVMTQSPSS LAVSAGEKVT MSCKSSQSLL NSRTRKNYLA WYQQKPGQSP KLLIYWASTR  60
ESGVPDRFTG SGSGTDFTLT ISSVQAEDLA VYYCTQSFIL RTFGGGTKLE IK          112

SEQ ID NO: 302          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 302
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRYYFDYWG QGTLVTVSS   119

SEQ ID NO: 303          moltype = AA  length = 112
FEATURE                 Location/Qualifiers
REGION                  1..112
                        note = an artificial synthesized sequence
```

```
source                  1..112
                        mol_type = protein
                        organism = synthetic construct
SEQUENCE: 303
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 304          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 304
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDA YSRYYFDYWG QGTLVTVSS   119

SEQ ID NO: 305          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 305
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 306          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 306
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRYYFDYWG QGTLVTVSS   119

SEQ ID NO: 307          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 307
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFAL RTFGQGTKVE IK          112

SEQ ID NO: 308          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 308
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRYYFDYWG QGTLVTVSS   119

SEQ ID NO: 309          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 309
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKASFIL RTFGQGTKVE IK          112

SEQ ID NO: 310          moltype = AA  length = 119
FEATURE                 Location/Qualifiers
REGION                  1..119
                        note = an artificial synthesized sequence
source                  1..119
                        mol_type = protein
```

```
                        organism = synthetic construct
SEQUENCE: 310
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRYYFDYWG QGTLVTVSS   119

SEQ ID NO: 311          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 311
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSAIL RTFGQGTKVE IK          112

SEQ ID NO: 312          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 312
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARTG YSRYYFDYWG QGTLVTVSS   119

SEQ ID NO: 313          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 313
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 314          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 314
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRYAFDYWG QGTLVTVSS   119

SEQ ID NO: 315          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 315
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 316          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 316
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARSG YSRYYFDYWG QGTLVTVSS   119

SEQ ID NO: 317          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 317
```

```
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 318          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 318
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDG YSRAYFDYWG QGTLVTVSS   119

SEQ ID NO: 319          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 319
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 320          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 320
EVQLVQSGAE VKKPGASVKV SCKASGFTFT SYYIHWVRQA PGQGLEWIGW IYPENDNTKY  60
NEKFKDRVTI TADTSTSTAY LELSSLRSED TAVYYCARDS YSNYYFDYWG QGTLVTVSS   119

SEQ ID NO: 321          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 321
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCTQSFIL RTFGQGTKVE IK          112

SEQ ID NO: 322          moltype = AA  length = 122
FEATURE                 Location/Qualifiers
REGION                  1..122
                        note = an artificial synthesized sequence
source                  1..122
                        mol_type = protein
                        organism = synthetic construct
SEQUENCE: 322
EVQLVESGGG LVQPGGSLRL SCAASGYSFT GYTMNWVRQA PGKDLEWVAL INPYKGVSTY  60
NQKFKDRFTI SVDKSKNTAY LQMNSLRAED TAVYYCARSG YYGDSDWYFD VWGQGTLVTV  120
SS                                                                 122

SEQ ID NO: 323          moltype = AA  length = 107
FEATURE                 Location/Qualifiers
REGION                  1..107
                        note = an artificial synthesized sequence
source                  1..107
                        mol_type = protein
                        organism = synthetic construct
SEQUENCE: 323
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKLELK                107

SEQ ID NO: 324          moltype = AA  length = 122
FEATURE                 Location/Qualifiers
REGION                  1..122
                        note = an artificial synthesized sequence
source                  1..122
                        mol_type = protein
                        organism = synthetic construct
SEQUENCE: 324
EVQLVESGGG LVQPGGSLRL SCAASGYSFT GYTMNWVRQA PGKGLEWVAL INPYKGVTTY  60
```

```
ADSVKGRFTI SVDKSKNTAY LQMNSLRAED TAVYYCARSG YYGDSDWYFD VWGQGTLVTV  120
SS                                                                122

SEQ ID NO: 325          moltype = AA  length = 107
FEATURE                 Location/Qualifiers
REGION                  1..107
                        note = an artificial synthesized sequence
source                  1..107
                        mol_type = protein
                        organism = synthetic construct
SEQUENCE: 325
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIK               107

SEQ ID NO: 326          moltype = AA  length = 122
FEATURE                 Location/Qualifiers
REGION                  1..122
                        note = an artificial synthesized sequence
source                  1..122
                        mol_type = protein
                        organism = synthetic construct
SEQUENCE: 326
EVQLVESGGG LVQPGGSLRL SCAASGYSFT GYTMNWVRQA PGKGLEWVAL INPYKGVSTY  60
ADSVKGRFTI SVDKSKNTAY LQMNSLRAED TAVYYCARSG YYGDSDWYFD VWGQGTLVTV  120
SS                                                                122

SEQ ID NO: 327          moltype = AA  length = 107
FEATURE                 Location/Qualifiers
REGION                  1..107
                        note = an artificial synthesized sequence
source                  1..107
                        mol_type = protein
                        organism = synthetic construct
SEQUENCE: 327
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIK               107

SEQ ID NO: 328          moltype = AA  length = 125
FEATURE                 Location/Qualifiers
REGION                  1..125
                        note = an artificial synthesized sequence
source                  1..125
                        mol_type = protein
                        organism = synthetic construct
SEQUENCE: 328
EVQLVESGGG LVQPGGSLRL SCAASGFTFN TYAMNWVRQA PGKGLEWVAR IRSKYNNYAT  60
YYADSVKDRF TISRDDSKNT LYLQMNSLRA EDTAVYYCVR HGNFGNSYVS WFAYWGQGTL  120
VTVSS                                                             125

SEQ ID NO: 329          moltype = AA  length = 109
FEATURE                 Location/Qualifiers
REGION                  1..109
                        note = an artificial synthesized sequence
source                  1..109
                        mol_type = protein
                        organism = synthetic construct
SEQUENCE: 329
EAVVTQEPSL TVSPGGTVTL TCRSSTGAVT TSNYANWVQQ KPGQAPRGLI GGTNKRAPWT  60
PARFSGSLLG GKAALTLSGA QPEDEAEYYC ALWYSNLWVF GGGTKLTVL             109

SEQ ID NO: 330          moltype = AA  length = 125
FEATURE                 Location/Qualifiers
source                  1..125
                        mol_type = protein
                        organism = Mus musculus
SEQUENCE: 330
EVQLVESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL  120
VTVSS                                                             125

SEQ ID NO: 331          moltype = AA  length = 109
FEATURE                 Location/Qualifiers
source                  1..109
                        mol_type = protein
                        organism = Mus musculus
SEQUENCE: 331
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNLWVF GGGTKLTVL             109
```

```
SEQ ID NO: 332          moltype = AA  length = 120
FEATURE                 Location/Qualifiers
REGION                  1..120
                        note = an artificial synthesized sequence
source                  1..120
                        mol_type = protein
                        organism = synthetic construct
SEQUENCE: 332
QVQLVQSGSE LKKPGASVKV SCKASGYTFT NYGMNWVRQA PGQGLEWMGW INTNTGKPTY  60
AEEFKGRFVF SLDTSVSTAY LQICSLKAED TAVYYCARRG DYRYAWFLYW GQGTLVTVSS  120

SEQ ID NO: 333          moltype = AA  length = 109
FEATURE                 Location/Qualifiers
REGION                  1..109
                        note = an artificial synthesized sequence
source                  1..109
                        mol_type = protein
                        organism = synthetic construct
SEQUENCE: 333
QAVVTQEPSL TVSPGGTVTL TCRSSTGAVT TSNYANWFQQ KPGQAPRTLI YGTSNRAPWT  60
PARFSGSLLG GKAALTLSGA QPEDEAEYFC ALWYSTHFVF GTGTKVTVL             109

SEQ ID NO: 334          moltype = AA  length = 120
FEATURE                 Location/Qualifiers
REGION                  1..120
                        note = an artificial synthesized sequence
source                  1..120
                        mol_type = protein
                        organism = synthetic construct
SEQUENCE: 334
QIQLVQSGPE LKKPGETVKI SCKASGYTFT NYGMNWVKQA PGKGLKWMGW INTNTGKPTY  60
AEEFKGRFVF SLETSASTTY LQINNLKNED TATYFCARRG DYRYAWFLYW GQGTLVTVSA  120

SEQ ID NO: 335          moltype = AA  length = 108
FEATURE                 Location/Qualifiers
REGION                  1..108
                        note = an artificial synthesized sequence
source                  1..108
                        mol_type = protein
                        organism = synthetic construct
SEQUENCE: 335
QAVVTQESAL TTSPGGTVIL TCRSSTGAVT TSNYANWVQE KPDHLFTGLI GGTSNRAPGV  60
PVRFSGSLIG DKAALTITGA QTEDDAMYFC ALWYSTHFVF GGGTKVTV              108

SEQ ID NO: 336          moltype = AA  length = 117
FEATURE                 Location/Qualifiers
REGION                  1..117
                        note = an artificial synthesized sequence
source                  1..117
                        mol_type = protein
                        organism = synthetic construct
SEQUENCE: 336
EVQLVQSGAE VKKPGASVKV SCKASGYTFT SYYIHWVRQA PGQGLEWIGW IYPGNVNTKY  60
NEKFKGRVTI TRDTSTSTAY LELSSLRSED TAVYYCARNH DYYFDYWGQG TLVTVSS     117

SEQ ID NO: 337          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 337
DIVMTQSPDS LAVSLGERAT INCKSSQSLL NSRTRKNYLA WYQQKPGQPP KLLIYWASTR  60
ESGVPDRFSG SGSGTDFTLT ISSLQAEDVA VYYCKQSYIL RTFGQGTKVE IK          112

SEQ ID NO: 338          moltype = AA  length = 117
FEATURE                 Location/Qualifiers
REGION                  1..117
                        note = an artificial synthesized sequence
source                  1..117
                        mol_type = protein
                        organism = synthetic construct
SEQUENCE: 338
QVQLVQSGAE VKKPGASVKV SCKASGYTFT SYYIHWVRQA PGQRLEWMGW IYPGNVNTKY  60
NEKFKGRVTI TADTSASTAY MELSSLRSED TAVYYCARNH DYYFDYWGQG TLVTVSS     117

SEQ ID NO: 339          moltype = AA  length = 112
FEATURE                 Location/Qualifiers
```

```
REGION                  1..112
                        note = an artificial synthesized sequence
source                  1..112
                        mol_type = protein
                        organism = synthetic construct
SEQUENCE: 339
DIVMTQSPDS LAVSLGERAT INCKSSQSLL NSRTRKNYLA WYQQKPGQPP KLLIYWASTR  60
ESGVPDRFSG SGSGTDFTLT ISSLQAEDVA VYYCKQSYIL RTFGQGTKVE IK          112

SEQ ID NO: 340          moltype = AA  length = 117
FEATURE                 Location/Qualifiers
source                  1..117
                        mol_type = protein
                        organism = Mus musculus
SEQUENCE: 340
EVQLQQSGPE LVKPGASVRI SCKASGYTFT SYYIHWMKQR PGQGLEWIGW IYPGNVNTKY  60
NEKFKGKATL TADNSSSTAN MQLSSLTSED SAVYFCARNH DYYFDYWGQG TTLTVSS     117

SEQ ID NO: 341          moltype = AA  length = 112
FEATURE                 Location/Qualifiers
source                  1..112
                        mol_type = protein
                        organism = Mus musculus
SEQUENCE: 341
DIVLTQSPSS LAVSAGEKVT MSCKSSQSLL NSRTRKNYLA WYQQKPGQSP KLLIYWASTR  60
ESGVPDRFTG SGSGTDFTLT ISSVQAEDLA VYYCKQSYIL RTFGGGTKLE IK          112

SEQ ID NO: 342          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 342
EVQLVESGPG LVKPSETLSL TCTVSGFSLT NYAIHWIRQP PGKGLEWIGV IWAGGNTKYN  60
SALMSRVTIS VDTSKNQFSL KLSSVTAADT AVYYCAREDS SGYVALDYWG QGTLVTVSS   119

SEQ ID NO: 343          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 343
DIVMTQSPDS LAVSLGERAT INCKSSQSLL SGRTRKNYLA WYQQKPGQPP KLLIYWASTR  60
ESGVPDRFSG SGSGTDFTLT ISSLQAEDVA VYYCKQSYYL LTFGQGTKVE IK          112

SEQ ID NO: 344          moltype = AA  length = 119
FEATURE                 Location/Qualifiers
source                  1..119
                        mol_type = protein
                        organism = Mus musculus
SEQUENCE: 344
QVQLKESGPG LVAPSQSLSI TCTVSGFSLT NYAIHWVRQP PGKGLDWLGV IWAGGNTKYN  60
SALMSRLSFS KDNSKSQVFL EINSLQTDDT AMYYCAREDS SGYVALDYWG QGTSVTVSS   119

SEQ ID NO: 345          moltype = AA  length = 112
FEATURE                 Location/Qualifiers
source                  1..112
                        mol_type = protein
                        organism = Mus musculus
SEQUENCE: 345
NIVMTQSPSS LAVSAGEKVT MSCKSSQSLL SGRTRKNYLA WYQQKPGQSP KLLIYWASTR  60
ESGVPDRFTG SGSGTDFTLT ISSVQAEDLA VYYCKQSYYL LTFGAGTKLE LK          112

SEQ ID NO: 346          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 346
EVQLVESGGG LVQPGGSLRL SCAVSGFSLT NYAIHWVRQA PGKGLEWVGV IWAGGNTKYN  60
SALMSRFTIS RDNSKNTLYL QMNSLRAEDT AVYYCAREDS SGYVALDYWG QGTLVTVSS   119

SEQ ID NO: 347          moltype = AA  length = 112
```

```
FEATURE                 Location/Qualifiers
REGION                  1..112
                        note = an artificial synthesized sequence
source                  1..112
                        mol_type = protein
                        organism = synthetic construct
SEQUENCE: 347
DIVMTQSPDS LAVSLGERAT INCKSSQSLL SGRTRKNYLA WYQQKPGQPP KLLIYWASTR  60
ESGVPDRFSG SGSGTDFTLT ISSLQAEDVA VYYCKQSYYL LTFGQGTKVE IK          112

SEQ ID NO: 348          moltype = AA  length = 120
FEATURE                 Location/Qualifiers
REGION                  1..120
                        note = an artificial synthesized sequence
source                  1..120
                        mol_type = protein
                        organism = synthetic construct
SEQUENCE: 348
EVQLVESGGG VVQPGGSLKL SCAASGFTFS GSAMHWVRQA SEKGLEWVGR IRSRANSYAT  60
AYAASVKDRF TISRDNSKNT AYLQMNSLKT EDTAVYYCIR DTMVRGIDYW GQGTLVTVSS  120

SEQ ID NO: 349          moltype = AA  length = 113
FEATURE                 Location/Qualifiers
REGION                  1..113
                        note = an artificial synthesized sequence
source                  1..113
                        mol_type = protein
                        organism = synthetic construct
SEQUENCE: 349
DIQMTQSPSS LAVSLGERAT INCKSSQSVL YSSNNKNYLV WYQQKLGQPP KLLIYRASTR  60
ESGVPDRFSG SGSGTDFTLT ISSLQAEDVA VYYCQQYYSV PWTFGQGTKV EIK         113

SEQ ID NO: 350          moltype = AA  length = 117
FEATURE                 Location/Qualifiers
REGION                  1..117
                        note = an artificial synthesized sequence
source                  1..117
                        mol_type = protein
                        organism = synthetic construct
SEQUENCE: 350
QVQLQQSGPE LVKPGASVRI SCKASGYTFT SDYIHWMRQR PGQGLEWIGW IYFGNVNTKY  60
NEKFKGKAIL TADKFSSTAY MQLSSLTSED SAVYFCARDG GYYFDYWGQG TTLTVSS     117

SEQ ID NO: 351          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 351
DIVMTQSPSS LAVSAGEKVT MSCKSSQSLL NSRTRKNYLA WYQQKPGQSP KLLIYWASTR  60
ESGVPDRFTG SGSGTDFTLT ISSVQAEDLA VYYCKQSFTL RTFGQGTKVE IK          112

SEQ ID NO: 352          moltype = AA  length = 117
FEATURE                 Location/Qualifiers
REGION                  1..117
                        note = an artificial synthesized sequence
source                  1..117
                        mol_type = protein
                        organism = synthetic construct
SEQUENCE: 352
QVQLQQSGPE LVKPGASVKM SCKASGYTFT SHYLHWVKQS PGQGLEWIVW INPGDGNVKY  60
NEKFKDKTTV TADRSSTTVH MFLSSLTSED SAIYFCARDG AYYFDYWGQG TTLTVSS     117

SEQ ID NO: 353          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 353
DIVMTQSPSS LAVSAGETVT MNCKSSQSLL NSRTRKNYLA WYQQKPGQSP KLLIYWASTR  60
ESGVPDRFTG SGSGTDFTLT ISTVQAEDLA VYYCKQSYTL RTFGQGTKVE IK          112

SEQ ID NO: 354          moltype = AA  length = 117
FEATURE                 Location/Qualifiers
REGION                  1..117
```

```
                       note = an artificial synthesized sequence
source                 1..117
                       mol_type = protein
                       organism = synthetic construct
SEQUENCE: 354
EVQLQQSGPE LVKPGASVKI SCKASGYSFT SYYIHWVKQR PGQGLEWIGW IFPGSDNTKY  60
NEKFKGKATL TADTSSSTAY MQLSSLTSED SAVYFCARNG NYAMDYWGQG TSVTVSS     117

SEQ ID NO: 355         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 355
EIVLSQSPSS LAVSAGEKVT MSCKSSQSLL NSRTRKNYLA WYQQKPGQSP KLLIYWASTR  60
ESGVPDRFTG SGSGTDFTLT ISSVQAEDLA VYYCKQSYTL RTFGGGTKLE IK          112

SEQ ID NO: 356         moltype = AA  length = 117
FEATURE                Location/Qualifiers
REGION                 1..117
                       note = an artificial synthesized sequence
source                 1..117
                       mol_type = protein
                       organism = synthetic construct
SEQUENCE: 356
EVQLQQSGPE LVKPGASVRI SCKASGYTFT SYYIHWMKQR PGQGLEWIGW IYPGNVNTKY  60
NEKFKGKATL TADNSSSTAN MQLSSLTSED SAVYFCARNH DYYFDYWGQG TTLTVSS     117

SEQ ID NO: 357         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 357
GIVMTQSPSS LAVSAGEKVT MSCKSSQSLL NSRTRKNYLA WYQQKPGQSP KLLIYWASTR  60
ESGVPDRFTG SGSGTDFTLT ISSVQAEDLA VYYCKQSYIL RTFGGGTKLE IK          112

SEQ ID NO: 358         moltype = AA  length = 120
FEATURE                Location/Qualifiers
REGION                 1..120
                       note = an artificial synthesized sequence
source                 1..120
                       mol_type = protein
                       organism = synthetic construct
SEQUENCE: 358
QIQLVQSGPE LKKPGETVKI SCKASGYTFT NYGMNWVKQA PGKGLKWMGW INTNTGKPTY  60
AEDFKGRFAF SLETSASTAY LQINNLKNED TATYFCARRG DYRYAWFTYW GQGTLVTVSA  120

SEQ ID NO: 359         moltype = AA  length = 108
FEATURE                Location/Qualifiers
REGION                 1..108
                       note = an artificial synthesized sequence
source                 1..108
                       mol_type = protein
                       organism = synthetic construct
SEQUENCE: 359
QAVVTQESAL TTSPGGTVIL TCRSSTGAVT TSNYANWVQE KPDHLFTGLI GGTSNRAPGV  60
PVRFSGSLIG DKAALTITGA QTEDDAMYFC ALWYSTHFVF GGGTKVTV              108

SEQ ID NO: 360         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 360
EVQLQQSGPE LVKPGTSVKI SCKASGFSFT NYYIHWMKQR PGQGLEWIGW IYPGSDNTKF  60
NDKFKGKATL TADTSSTTAY MQLSSLTSED SAVYYCARDS ITNYYFDYWG QGTTLTVSS   119

SEQ ID NO: 361         moltype = AA  length = 112
FEATURE                Location/Qualifiers
REGION                 1..112
                       note = an artificial synthesized sequence
source                 1..112
```

```
                         mol_type = protein
                         organism = synthetic construct
SEQUENCE: 361
DVVMTQTPSS LAVSTGEKVT MTCKSSQSLL NIRTRKNCLA WYQQKPGQSP KLLIFWASTR  60
YSGVPDRFTG SGSGTDFTLT IRSVQPEDLA VYYCTQSYTL RTFGGGTKLE IK          112

SEQ ID NO: 362           moltype = AA  length = 119
FEATURE                  Location/Qualifiers
REGION                   1..119
                         note = an artificial synthesized sequence
source                   1..119
                         mol_type = protein
                         organism = synthetic construct
SEQUENCE: 362
QVQLQQSGSE LVRPGASLKL SCKASGYTFT SYWMHWVRQR PGQGLEWIGN FYPGDLTVNY  60
DEKFKNKVTL AVDTSSSTAF LQLSSLTSED SAVYYCTRDA YSRYFFDYWG QGTTLTVSS   119

SEQ ID NO: 363           moltype = AA  length = 112
FEATURE                  Location/Qualifiers
REGION                   1..112
                         note = an artificial synthesized sequence
source                   1..112
                         mol_type = protein
                         organism = synthetic construct
SEQUENCE: 363
DIVMTQSPSS LAVSAGEKVT MSCKSSQSLL NSRTRKNYLA WYQQKPGQSP KLLIYWASTR  60
ESGVPDRFTG SGSGTDFTLT ISSVQTEDLA VYYCCQSFIL RTFGGGTKLE IK          112

SEQ ID NO: 364           moltype = AA  length = 119
FEATURE                  Location/Qualifiers
REGION                   1..119
                         note = an artificial synthesized sequence
source                   1..119
                         mol_type = protein
                         organism = synthetic construct
SEQUENCE: 364
QVQLQQSGPE LVKPGASVKI SCKASGYSFT NYYMHWVKQR PGQGLEWIGW ISPGSGSIKY  60
NEKFKGKATL TADTSSSTAY MQLSSLTSED SAVYYCARDG YSLYFFDFWG QGTTLTVSS   119

SEQ ID NO: 365           moltype = AA  length = 112
FEATURE                  Location/Qualifiers
REGION                   1..112
                         note = an artificial synthesized sequence
source                   1..112
                         mol_type = protein
                         organism = synthetic construct
SEQUENCE: 365
DIVMTQSPSS LAVSAGEKVT MTCKSSQSLL NSRTRKNYLA WYQQKPGQSP KLLIYWASTR  60
ESGVPDRFTG SGSGTDFTLT ISSVQAEDLA VYYCKQSFIL RTFGGGTKLE LK          112

SEQ ID NO: 366           moltype = AA  length = 119
FEATURE                  Location/Qualifiers
REGION                   1..119
                         note = an artificial synthesized sequence
source                   1..119
                         mol_type = protein
                         organism = synthetic construct
SEQUENCE: 366
QVQLQQSGPE LVKPGTSVKI SCKTSGYSFI NYYTHWVKQR PGQGLEWIGW IYPGNGNIKY  60
NEKFMGKATL TADTSSTTAH MHLSSLVSED SAVYYCARDS YGSYYFDYWG QGTTLTVSS   119

SEQ ID NO: 367           moltype = AA  length = 112
FEATURE                  Location/Qualifiers
REGION                   1..112
                         note = an artificial synthesized sequence
source                   1..112
                         mol_type = protein
                         organism = synthetic construct
SEQUENCE: 367
DIVMTQSPSS LAVSVGEKVT MSCKSSQSLL NSRTRKNYLA WYQQKPGQSP KLLIYWASTR  60
ESGVPVRFTG SGSGTDFTLT ISSVQAEDLA VYYCTQSFIL RTFGGGTKLE IK          112

SEQ ID NO: 368           moltype = AA  length = 119
FEATURE                  Location/Qualifiers
REGION                   1..119
                         note = an artificial synthesized sequence
source                   1..119
                         mol_type = protein
                         organism = synthetic construct
```

```
SEQUENCE: 368
QVQLQQSGPE LVKPGTSVKI SCKTSGYNFI NYYTHWVKQR PGQGLEWIGW IYPGNGNIKY  60
NEKFMGKATL TADTSSTTAH MHLSSLVSED SAVYYCARDS YGSYYFDYWG QGTTLTVSS   119

SEQ ID NO: 369          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 369
DIVMTQSPSS LAVSAGEKVT MTCKSSQSLL NSRTRKNYLA WYQQKPGQSP KLLIYWASTR  60
ESGVPDRFTG SGSGTDFTLT ISSVQAEDLA VYYCKQSFIL RTFGGGTKLE IK          112

SEQ ID NO: 370          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 370
QVQLQQSGPE LVKPGASLKI SCKASGYSFA NYYTHWVRQR PGQGLEWIGW LYPGNGDTRY  60
NEKFKDKATL TADTSSNTAS MQLNSLTSED SAVYYCTRDS YGNYFFDYWG QGTTLIVSS   119

SEQ ID NO: 371          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 371
DIVMTQSPSS LAVSAGEKVT MSCKSSQSLL NSRTRKNYLA WYQQKPGQSP KLLIFWASTR  60
ESGVPDRFTG SGSGTDFTLT ISSVQAEDLA VYYCKQSFIL RTFGGGTKLE LK          112

SEQ ID NO: 372          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 372
QVQLQQSGSE LVRPGASLKL SCKASGYTFT SYWMHWVRQR PGQGLEWIGN SYPGDLNVNY  60
DEKFKNKVTL AVDTSSSTAF LQLSSLTSED SAVYYCTRDA YSRYFFDYWG QGTTLTVSS   119

SEQ ID NO: 373          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 373
DIVMTQSPSS LAVSAGEKVT MSCKSSQSLL NSRTRKNYLA WYQQKPGQSP KLLIYWASTR  60
ESGVPDRFTG SGSGTDFTLT ISSVQTEDLA VYYCCQSFIL RTFGGGTKLE IK          112

SEQ ID NO: 374          moltype = AA  length = 119
FEATURE                 Location/Qualifiers
REGION                  1..119
                        note = an artificial synthesized sequence
source                  1..119
                        mol_type = protein
                        organism = synthetic construct
SEQUENCE: 374
QVQLQQSGPE MVKPGASVTI SCKTSGFTFT SYYIHWMMQR PGQGLEWIGW LYPGDVSTRY  60
NEKFRDKATL TADKSSTTAY LYLSSLTSED SAVYFCARDS SASYYFDFWG QGTTLTVSS   119

SEQ ID NO: 375          moltype = AA  length = 112
FEATURE                 Location/Qualifiers
REGION                  1..112
                        note = an artificial synthesized sequence
source                  1..112
                        mol_type = protein
                        organism = synthetic construct
SEQUENCE: 375
DIVMTQSPSS LAVSAGEMVT LHCKSSQSLL NIRTRKNYLA WYLQKPGQSP RLLIYWASTR  60
```

```
ASGVPDRFTG SGSGTDFTLT ISSVQPEDLA VYYCTQSFIL RTFGGGTKLE LK         112

SEQ ID NO: 376         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 376
QVQLQQPGSE LVRPGASVTL SCTASGYSFT SYWMHWVKQR PGQGLEWVGN IYPGGEIINY  60
AEKFKTKGTL TVDISSSTAY MHLSSLTSDD SAVYYCTRDT TGNYFFDYWG QGTTLTVSS   119

SEQ ID NO: 377         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 377
DIVMTQSPSS LAVSAGEKVT MSCKSSQSLL NSRTRKNYLA WYQQKPGLSP KLLIYWASTR  60
ESGVPERFTG SGSGTDFTLT ISSVQTEDLA VYYCTQSFIL RTFGGGTRLE IK         112

SEQ ID NO: 378         moltype = AA  length = 116
FEATURE                Location/Qualifiers
REGION                 1..116
                       note = an artificial synthesized sequence
source                 1..116
                       mol_type = protein
                       organism = synthetic construct
SEQUENCE: 378
QSVKESEGGL FKPTDTLTLT CTVSGCSLSS CAISWVRQAP GKGLEWIGFM SVTGSAYYAN  60
WAKSRSTITR NTNENTVTLK MTRLTAADTA IYFCARVGIG SGLNIWGQGT LVTVSS      116

SEQ ID NO: 379         moltype = AA  length = 110
FEATURE                Location/Qualifiers
REGION                 1..110
                       note = an artificial synthesized sequence
source                 1..110
                       mol_type = protein
                       organism = synthetic construct
SEQUENCE: 379
DMTQTPSSKS VPVGDTVTIN CQASETVYSN NYLAWFQQKP GQPPKRLIYG VSTLDSGVPP  60
RFSGSGSGTQ FTLTISDVVC DDAATYYCAG YKTSSSYAIA FGGGTELEIL            110

SEQ ID NO: 380         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 380
QVQLQQSGPE LVKPGASVTI SCTASGFTFT SYYIHWVRQR PGQGLEWIGW IYPENDNTKY  60
NEKFKDKATL TADTSSSTAY MQLSSLTSED SAVYYCARDG YSRYYFDYWG QGTTLTVSS   119

SEQ ID NO: 381         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 381
DIVMTQSPSF LAVSAGEKVT MSCKSSQSLL NSRTRKNYLA WYQQRPGQSP KLLIYWTSTR  60
KSGVPDRFTG SGSGTDFTLT ISSVQAEDLA IYYCKQSFIL RTFGGGTKLE IK         112

SEQ ID NO: 382         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 382
EVQLVQSGAE VKKPGASVIV SCKASGFTFT SYYIHWVRQA PGQGLEWIGW IYPENDNRKY  60
NEKFKDRVTI SADTSESFAY LQLHSLRSED TAVYYCARDG YSRYYFDYWG QGTLVTVSS   119
```

```
SEQ ID NO: 383         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 383
DIVMTQSPDS LAVSLGERAT INCKSSQSLL NSRTRKNYLA WYQQKPGQSP KLLIYWTSTR  60
KSGVPDRFSG SGSGTDFTLT ISSLQAEDVA VYYCKQSFIL RTFGQGTKVE IK          112

SEQ ID NO: 384         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 384
EVQLVQSGAE VKKPGASVKV SCKASGFTFT SYYIHWVRQA PGQGLEWIGW IYPENDNRKY  60
NEKFKDRVTI TRDTSTSTAY LELSSLRSED TAVYYCARDG YSRYYFDYWG QGTLVTVSS   119

SEQ ID NO: 385         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 385
DIVMTQSPDS LAVSLGERAT INCKSSQSLL NSRTRKNYLA WYQQKPGQPP KLLIYWTSTR  60
KSGVPDRFSG SGSGTDFTLT ISSLQAEDVA VYYCKQSFIL RTFGQGTKVE IK          112

SEQ ID NO: 386         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 386
QVQLQQSGPE LVKPGTSVKM SCKASGYTFT NYYIHWVRQR PGQGLEWIGW IYPGDVSTKY  60
NEKFKGKTTL TADKSSSTAY MLLSGLTSED SAIYFCARDG YSFYYFDYWG QGTTLTVSS   119

SEQ ID NO: 387         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 387
DIVLTQSPSS LAVSAGEKVT MSCKSSQSLL NSRTRKNYLT WYQQKPGQSP KLLIYWASTR  60
DSGVPDRFSG SGSGTDFTLT ISSVQAEDLA VYYCTQSYTL RTFGGGTKLE IK          112

SEQ ID NO: 388         moltype = AA  length = 119
FEATURE                Location/Qualifiers
REGION                 1..119
                       note = an artificial synthesized sequence
source                 1..119
                       mol_type = protein
                       organism = synthetic construct
SEQUENCE: 388
EVQLVQSGAE VKKPGASVKV SCKASGYTFT NYYIHWVRQA PGQGLEWIGW IYPGDVSTKY  60
NEKFKGRVTI TRDTSTSTAY LELSSLRSED TAVYYCARDG YSFYYFDYWG QGTLVTVSS   119

SEQ ID NO: 389         moltype = AA  length = 112
FEATURE                Location/Qualifiers
REGION                 1..112
                       note = an artificial synthesized sequence
source                 1..112
                       mol_type = protein
                       organism = synthetic construct
SEQUENCE: 389
DIVMTQSPDS LAVSLGERAT INCKSSQSLL NSRTRKNYLT WYQQKPGQPP KLLIYWASTR  60
DSGVPDRFSG SGSGTDFTLT ISSLQAEDVA VYYCTQSYTL RTFGQGTKVE IK          112

SEQ ID NO: 390         moltype = AA  length = 125
FEATURE                Location/Qualifiers
```

-continued

```
REGION                 1..125
                       note = an artificial synthesized sequence
source                 1..125
                       mol_type = protein
                       organism = synthetic construct
SEQUENCE: 390
EVQLVESGGG LVQPGGSLRL SCAASGFTFN TYAMNWVRQA PGKGLEWVGR IRSKYNNYAT  60
YYADSVKDRF TISRDNSKNT LYLQMNSLRA EDTAVYYCVR HGNFGNSYVS WFAYWGQGTL  120
VTVSS                                                              125

SEQ ID NO: 391         moltype = AA  length = 109
FEATURE                Location/Qualifiers
REGION                 1..109
                       note = an artificial synthesized sequence
source                 1..109
                       mol_type = protein
                       organism = synthetic construct
SEQUENCE: 391
EAVVTQEPSL TVSPGGTVTL TCRSSTGAVT TSNYANWFQQ KPGQAPRTLI YGTNKRAPWT  60
PARFSGSLLG GKAALTLSGA QPEDEAEYYC ALWYSNLWVF GGGTKLTVL             109
```